US011326141B2

(12) United States Patent
Hoffmann-Petersen et al.

(10) Patent No.: US 11,326,141 B2
(45) Date of Patent: May 10, 2022

(54) METHOD FOR ONLINE MONITORING OF MASHING PROCESSES USING INFRARED SPECTROSCOPY

(71) Applicant: Specshell ApS, Charlottenlund (DK)

(72) Inventors: Erik Hoffmann-Petersen, Charlottenlund (DK); Andreas Jonas Kunov-Kruse, Charlottenlund (DK)

(73) Assignee: SPECSHELL, ApS, Charlottenlund (DK)

( * ) Notice: Subject to any disclaimer, the term of this patent is extended or adjusted under 35 U.S.C. 154(b) by 448 days.

(21) Appl. No.: 15/303,166

(22) PCT Filed: Apr. 10, 2015

(86) PCT No.: PCT/EP2015/057887
§ 371 (c)(1),
(2) Date: Oct. 10, 2016

(87) PCT Pub. No.: WO2015/155353
PCT Pub. Date: Oct. 15, 2015

(65) Prior Publication Data
US 2017/0029761 A1    Feb. 2, 2017

(30) Foreign Application Priority Data

Apr. 11, 2014 (DK) .............................. PA201470208
Mar. 6, 2015 (DK) .............................. PA201570129

(51) Int. Cl.
*C12M 1/34* (2006.01)
*C12M 1/36* (2006.01)
(Continued)

(52) U.S. Cl.
CPC ............ *C12M 41/32* (2013.01); *C12M 41/48* (2013.01); *C12M 45/09* (2013.01); *G01N 21/272* (2013.01);
(Continued)

(58) Field of Classification Search
CPC ...... C12M 41/32; C12M 41/48; C12M 45/09; C12M 1/3469
See application file for complete search history.

(56) References Cited

U.S. PATENT DOCUMENTS

| 4,913,914 A | 4/1990 | Hashimoto et al. |
| 4,926,747 A | 5/1990 | Hashimoto et al. |
| (Continued) | | |

FOREIGN PATENT DOCUMENTS

| BR | PI 1103305-3 A2 | 3/2014 |
| DE | 40 02 108 A1 | 8/1991 |
| (Continued) | | |

OTHER PUBLICATIONS

Sivakesava ("Determination of Sugars in Aqueous Mixtures Using Mid-Ingrared Spectroscopy" Applied Engineering in Agriculture, 2000, 16(5), 543-550) (Year: 2000).*
(Continued)

*Primary Examiner* — Robert J Yamasaki
*Assistant Examiner* — Charles Zoltan Constantine
(74) *Attorney, Agent, or Firm* — Crowell & Moring LLP

(57) ABSTRACT

The invention relates to a method for controlling an enzymatic pre-treatment process, e.g. a mashing process. The method allows for accurate determination of specific sugar molecules as well as the average length of the sugar chains in real-time during e.g. a mashing process. Further information on e.g. the concentration of dissolved protein and free amino acids can also be obtained simultaneously. The method comprises the use of an infrared (IR) spectrometer for continuously measuring attenuated total reflectance (ATR) IR spectra of samples obtained during pre-treatment of biomass.

15 Claims, 43 Drawing Sheets

(51) Int. Cl.
    *C12M 1/00*        (2006.01)
    *G01N 21/552*     (2014.01)
    *G01N 21/84*      (2006.01)
    *G01N 21/3577*    (2014.01)
    *G01N 21/27*      (2006.01)
    *G01N 21/85*      (2006.01)

(52) U.S. Cl.
    CPC ....... *G01N 21/3577* (2013.01); *G01N 21/552* (2013.01); *G01N 21/84* (2013.01); *G01N 21/8507* (2013.01); *G01N 2021/8416* (2013.01)

(56) References Cited

U.S. PATENT DOCUMENTS

| | | | |
|---|---|---|---|
| 2011/0081672 A1* | 4/2011 | Andersen | C12M 21/12 435/22 |
| 2011/0278457 A1* | 11/2011 | Lendl | G01N 21/8507 250/338.1 |
| 2014/0073820 A1* | 3/2014 | Bazzana | C12M 21/12 568/913 |

FOREIGN PATENT DOCUMENTS

| | | |
|---|---|---|
| DE | 198 28 688 A1 | 7/1999 |
| DE | 100 23 704 A1 | 11/2001 |
| EP | 0 851 027 A1 | 7/1996 |
| WO | WO 2009/074650 A2 | 6/2009 |
| WO | WO 2009/121423 A1 | 10/2009 |
| WO | WO 2009/149766 A1 | 12/2009 |

OTHER PUBLICATIONS

Cozzolino ("An Attenuated Total Reflectance mid infrared (ATR-MIR) spectroscopy study of gelatinization in barley" Carbohydrate Polymers, 2014, 108, 266-271, published Feb. 28, 2014) (Year: 2014).*
Bureau ("Applicant of ATR-FTIR for a rapid and simultaneous determination of sugars and organic acids in apricot fruit" Food Chemistry, 115, 2009, 1133-1140) (Year: 2009).*
Grassi ("Assessment of the sugars and ethanol development in beer fermentation with FT-IR and multivatiate curve resolution models", Food Research International, 2014, 62, 602-608, published on Apr. 8, 2014) (Year: 2009).*
Haberkorn, M. et al.; "A mid-IR flow-through sensor for direct monitoring of enzyme catalyzed reactions. Case study: measurement of carbohydrates in beer"; The Analyst, RSC Publications, GB, vol. 127; Jan. 1, 2002; pp. 109-113.
Roychoudhury, P. et al.; "The potential of mid infrared spectroscopy (MIRS) for real time bioprocess monitoring"; Analytica Chimica Acta, Elsevier, Amsterdam, NL, vol. 571, No. 2; Jul. 7, 2006; pp. 159-166.
Tenhunen, J. et al.; "Determination of Fermentable Sugars and Nitrogenous Compounds in Wort by Near-and Mid-Infrared Spectroscopy"; J. Inst. Brew., vol. 100; Jan.-Feb. 1994.
Tucker, M.P. et al.; "Fourier Transform Infrared Quantification of Sugars in Pretreated Biomass Liquors"; Molecular Biotechnology, vol. 84-86, No. 1-9; Jan. 1, 2000; pp. 39-50.
Zhang, Y.-H. P. et al.; "Determination of the Number-Average Degree of Polymerization of Cellodextrins and Cellulose with Application to Enzymatic Hydrolysis"; Biomacromolecules, vol. 6; May 1, 2005; pp. 1510-1515.
International Search Report completed Jul. 6, 2015 for International Application No. PCT/EP2015/057887.
Written Opinion completed Jul. 6, 2015 for International Application No. PCT/EP2015/057887.

* cited by examiner

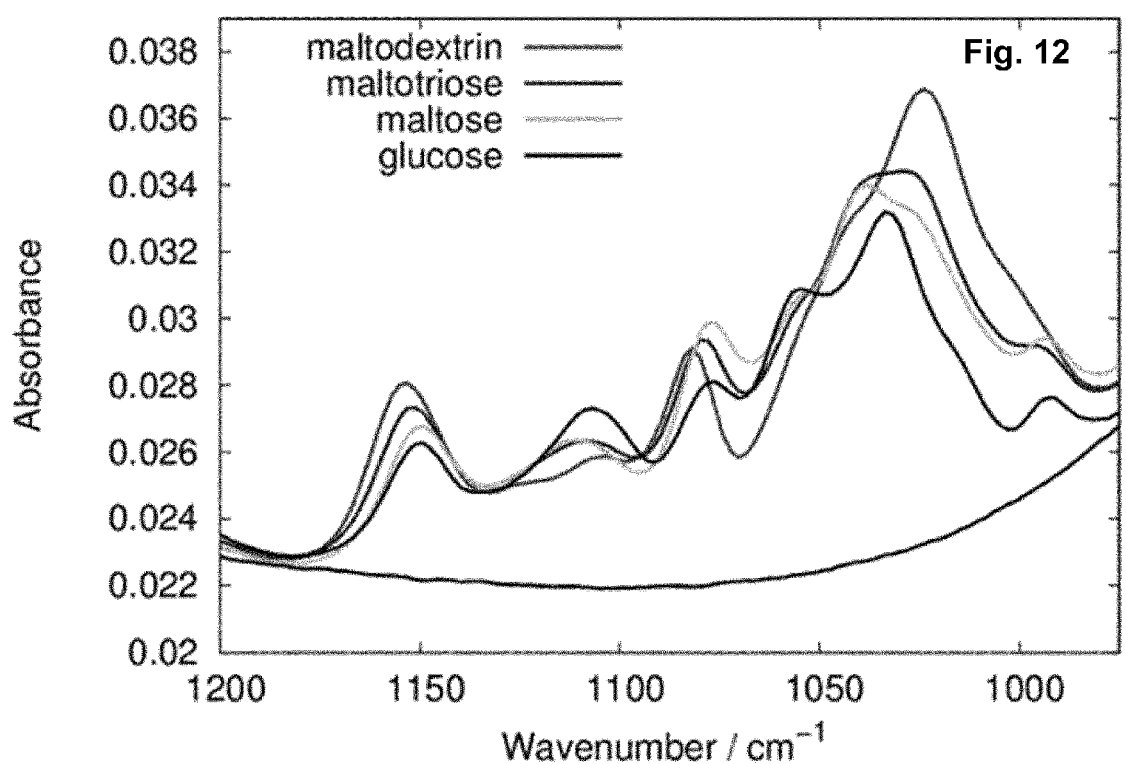

$R_1$, $R_2$ = Any chemical or biological fragment with the formula $C_aN_bO_cS_dH_e$

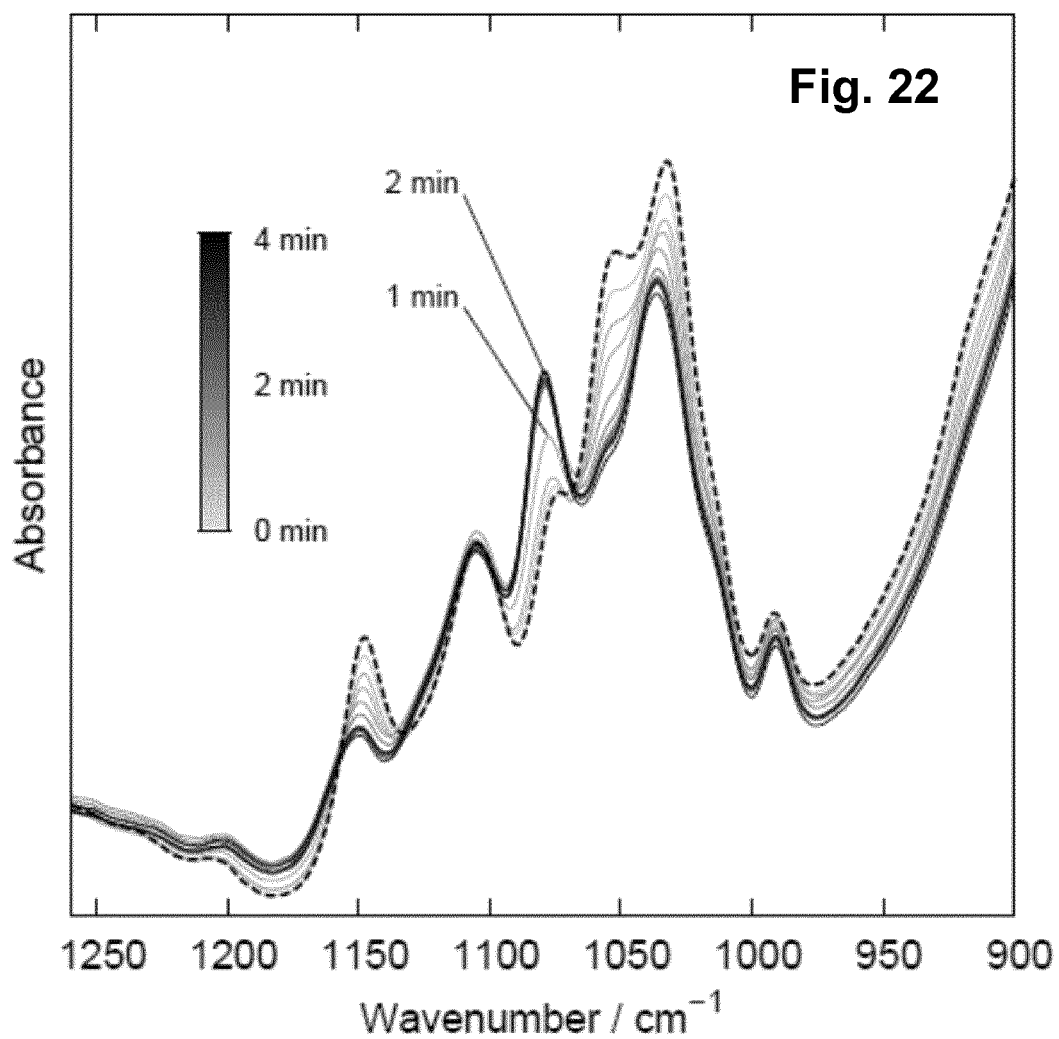

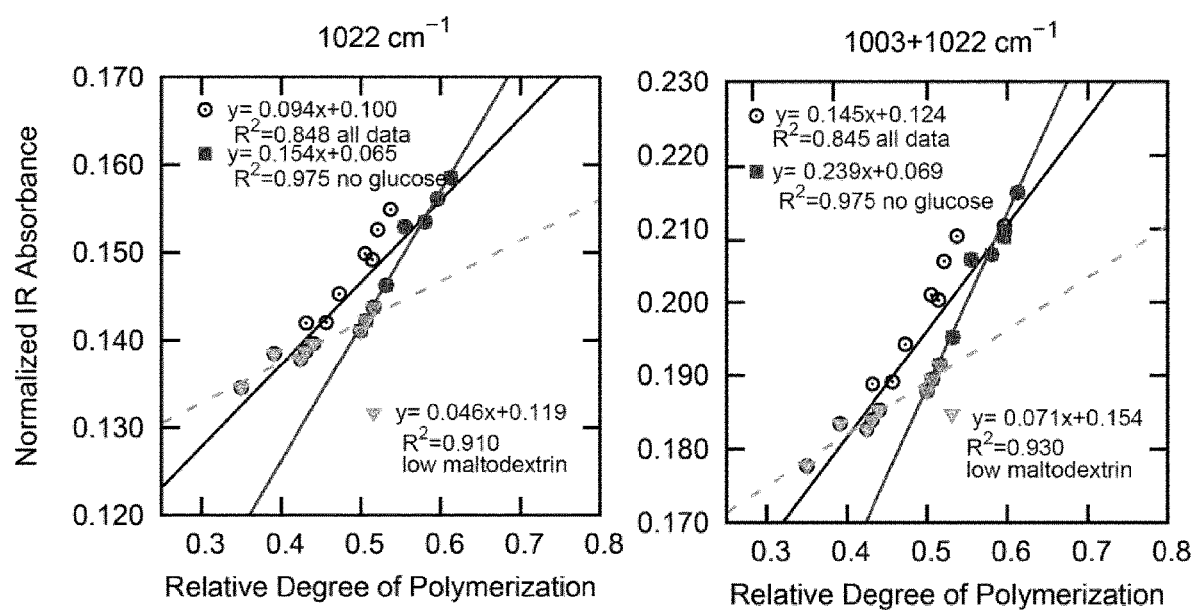
Fig. 27 (continued I)

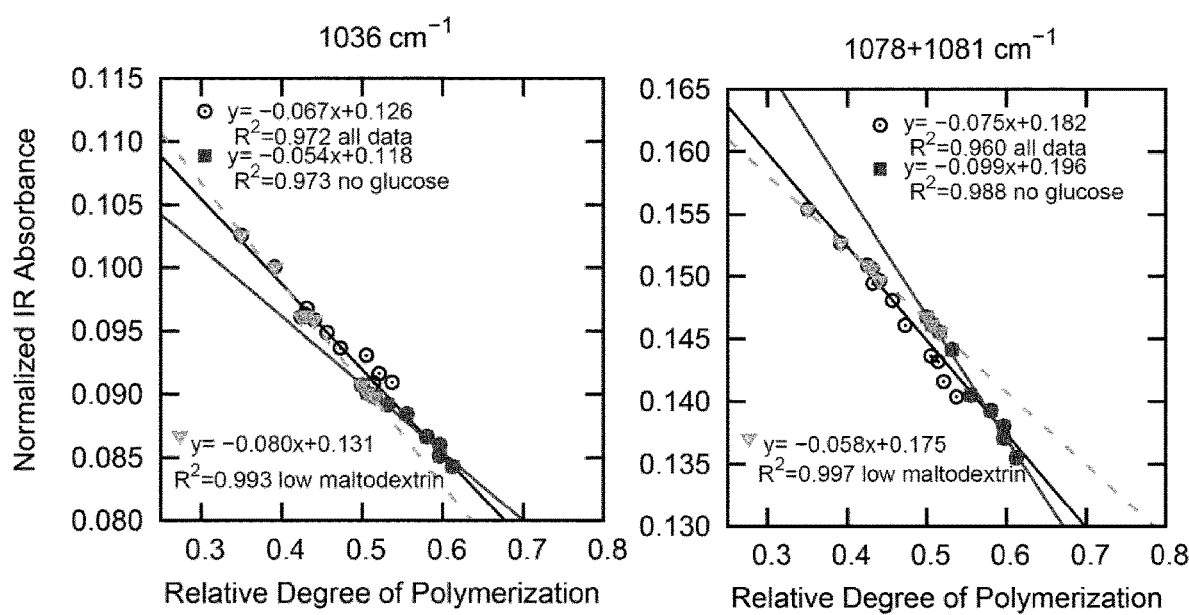
Fig. 27 (continued II)

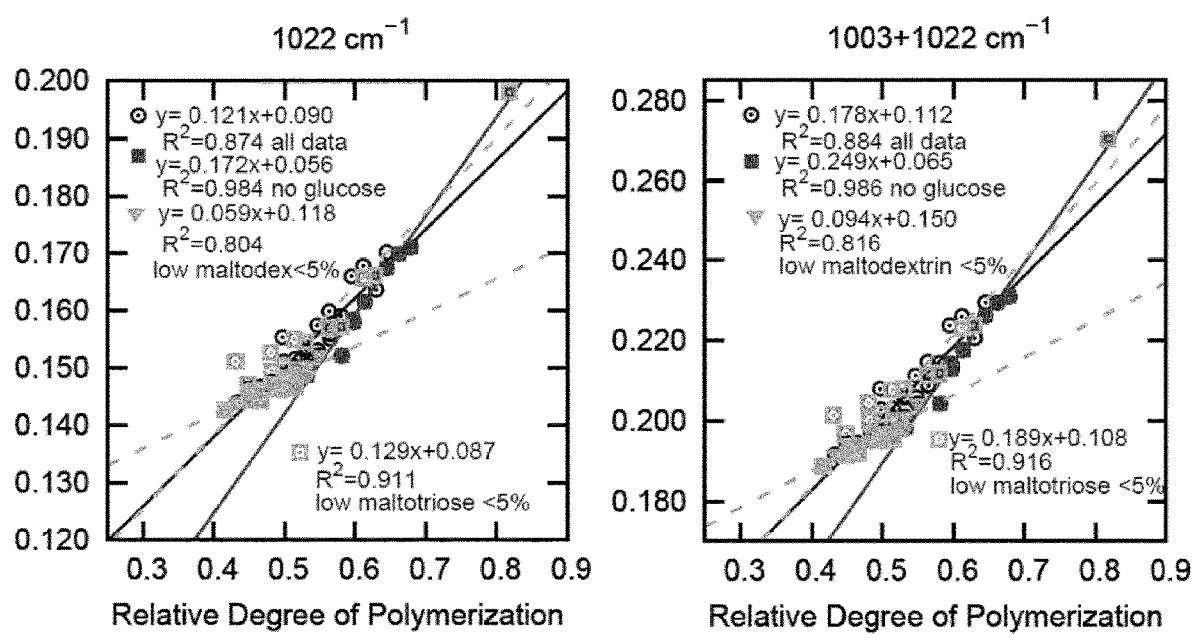
Fig. 30 (continued I)

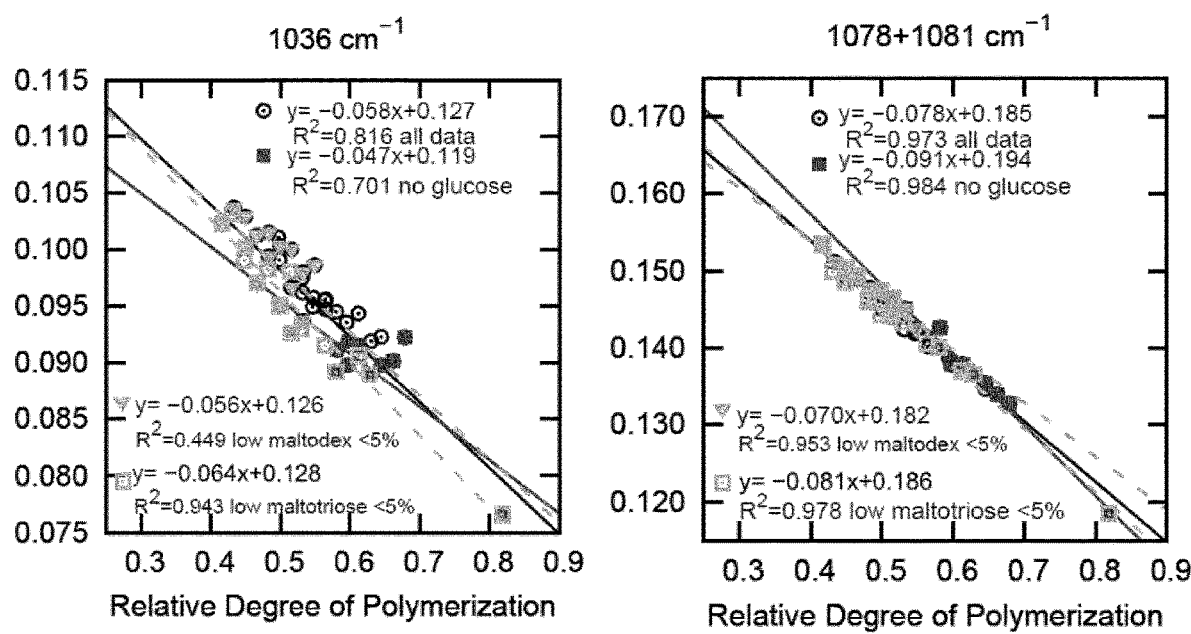
Fig. 30 (continued II)

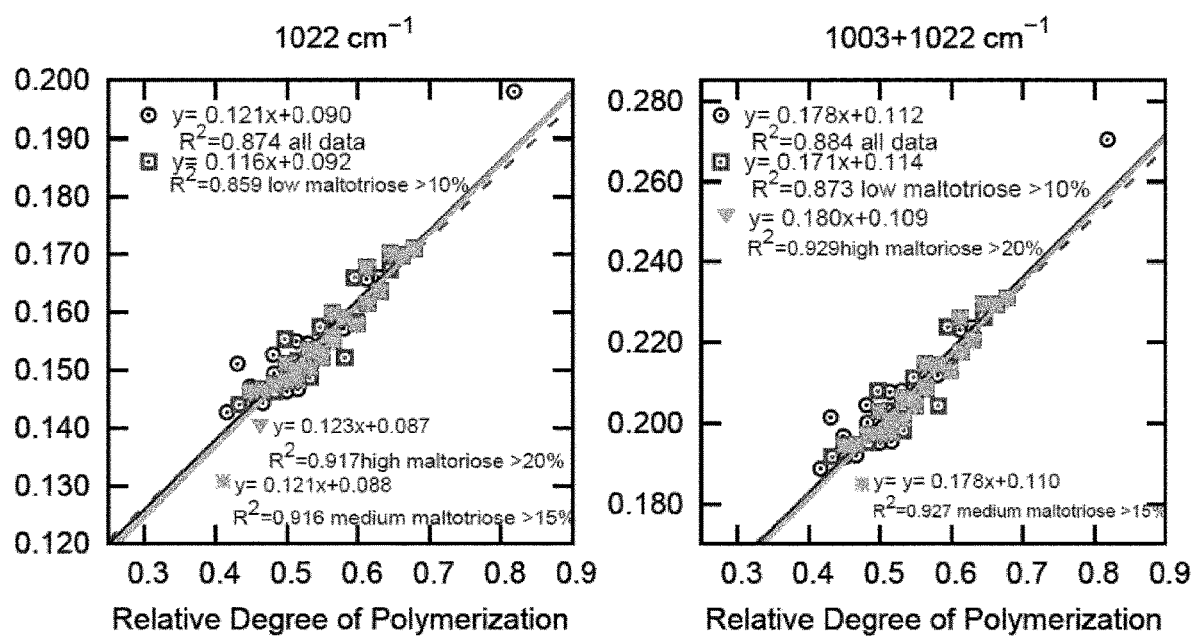
Fig. 32 (continued I)

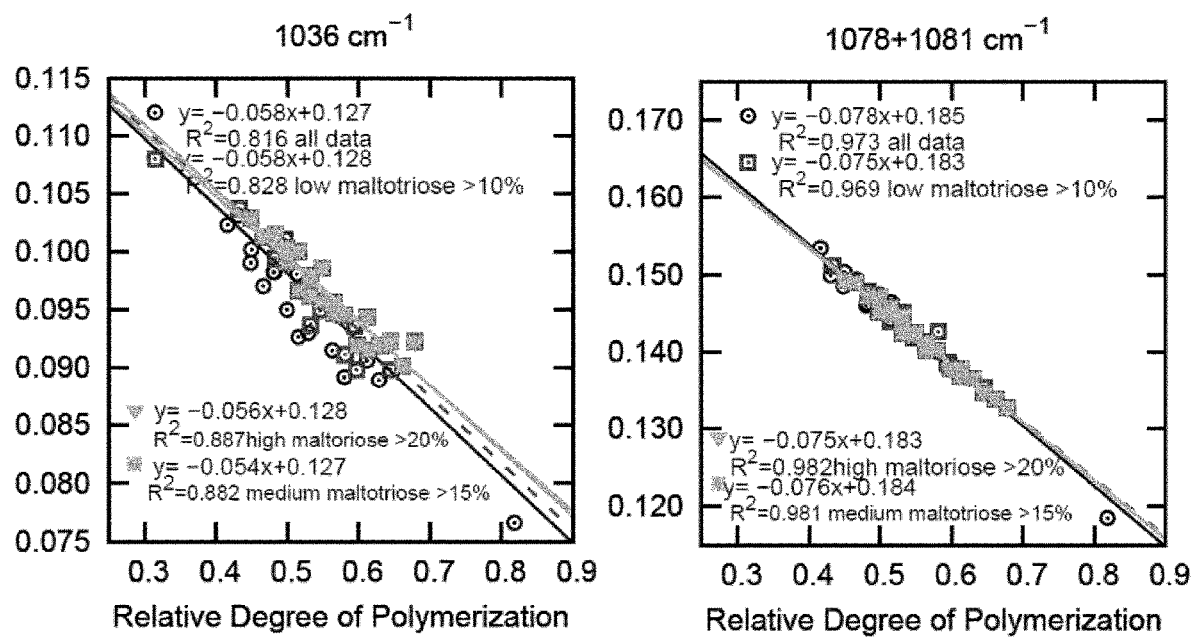
Fig. 32 (continued II)

METHOD FOR ONLINE MONITORING OF MASHING PROCESSES USING INFRARED SPECTROSCOPY

This application claims the benefit under 35 U.S.C. § 371 of International Application No. PCT/EP2015/057887, filed Apr. 10, 2015, which claims the benefit of Danish Patent Application No. PA 2014 70208, filed Apr. 11, 2014 and Danish Patent Application No. PA 2015 70129, filed Mar. 6, 2015 which are incorporated by reference herein in their entirety.

The invention relates to a method and a system for controlling an enzymatic pre-treatment process, e.g. a mashing process. This allows for accurate determination of the sugar molecules present in a solution and of the average length of the sugar chains in real-time during the enzymatic pre-treatment process, e.g. a mashing process. Furthermore, information on e.g. the concentration of dissolved carbohydrates, such as e.g. protein and free amino acids, may also be obtained simultaneously as information on the average length of the sugar chains.

BACKGROUND

When making e.g. a brew, before the microbiological fermentation of natural occurring carbohydrates in a wide range of cereals and other starch and di- and polysaccharide containing crops, the natural occurring carbohydrates often require an enzymatic pretreatment. This enzymatic pretreatment is known as mashing. Examples of cereals and other crops that may need to undergo this mashing procedure are barley, wheat, rye, oat, rice, corn, wood or potatoes.

In some cases the cereals are malted prior to the mashing. During the malting process, natural enzymes are developed within the crops. In other cases enzymes are added to the cereals or crops before the mashing starts. During the mashing process, water is added to the crop and the temperature is raised and maintained at certain temperatures where enzymes added or naturally occurring is most active. A mashing normally includes several temperature steps to stimulate the different enzymes.

During a mashing process, different types of mono-, di- and polymeric sugar compounds are developed due to the enzymatic transformation of the naturally occurring starch. Smaller sugar units (such as e.g. maltose) are converted to ethanol during the fermentation whereas the slightly longer chains (such as e.g. maltodextrines) are maintained throughout the fermentation and ads preferable sweet flavor tones to the final brew.

After the mashing process is completed, the ratio of the short chained sugars and long chained sugars must be within a very narrow interval to get the kind of brew wanted. "Over mashing", where all starch are fully converted into maltose, will yield a brew with a high alcohol content but with a flat and unpleasant or bitter flavor. On the other hand "under mashing", where only a minor portion of the starch is converted to maltose, will result in a very sweet brew with a low alcohol content. For the most types of brews a mashing process that takes the mash to somewhere in between these two extremes is preferred. However, the control of the mashing process is very challenging and no good online methods are available to measure the ratio between short chain and long chain sugar compounds.

Other important enzymatic processes include hydrolysis of peptide bonds in the proteins of the crop. The content of hydrolyzed protein also affects the characteristics of the final brew and is therefore an important factor to control in the mashing process. The degree of hydrolysis of protein is also challenging to control.

The overall brewing process is very well understood from a scientific point of view—especially the fermentation process is studied in details and is often operated as a sophisticated and highly engineered biochemical process.

In contrast, the mashing is one of the few "black boxes" left in the brewing industry and the mashing is still fundamentally performed by using "recipes" and trial-and-error approaches. This is however problematic in many senses. One concern is that since each batch of malt can have different compositions with regard to both sugar and protein substrates and active amylase and protease enzymes, the optimal mashing procedure is never exactly the same.

The reason for the lack of understanding and control of the mashing process is due to that no analytical technologies are available, which offers online monitoring of the mashing. HPLC (High performance Liquid Chromatography) or GPC (gel permeation chromatography) can be used to analyze the sugar compounds in the mash, but the time to run just one sample is longer than the time scale of each temperature step in the mashing itself, thus it is useless for online monitoring. Hence, new analytical technologies are needed to optimize and allow better understanding of this important biochemical process type.

DESCRIPTION OF THE INVENTION

Disclosed herein in a first aspect of the invention is a method for controlling an enzymatic pre-treatment process, e.g. a mashing process. The method comprises the actions of:
a) providing a sample to a system with a tank;
b) obtaining a sample mixture by:
   adding one or more enzymes to the sample if the sample does not contain one or more enzymes already, or
   possibly adding one or more enzymes to the sample already containing one or more enzymes;
c) continuously exposing a part of the sample mixture to an infrared (IR) spectrometer;
d) continuously measuring attenuated total reflectance (ATR) IR spectra of the sample mixture with the IR spectrometer in real time at wavelengths between 400-3500 $cm^{-1}$ during the enzymatic pre-treatment process, and
e) feeding the measured IR spectra to a calculating unit which:
   calculates information relating to specific species present in the sample mixture during the enzymatic pre-treatment process based on the IR spectra, wherein the information relating to the specific species present in the samples mixture is:
   the ratio between the different specific species, and/or
   the concentration of one or more of the specific species, and/or
   the degree of polymerization of one or more of the specific species; and
   feeds the information relating to the specific species in the sample mixture back to the user and/or to a tank control system connected to the tank.

Disclosed herein in a second aspect of the invention is a system for controlling an enzymatic pre-treatment process. The system comprises a tank adapted for containing a sample mixture comprising a sample to be enzymatically pre-treated and possibly one or more enzymes added to the sample during the enzymatic pre-treatment process.

The system further comprises an analyzing unit connected to an IR spectrometer, the analyzing unit being adapted for bringing the sample mixture in direct contact with the IR spectrometer for measuring attenuated total reflectance (ATR) IR spectra of the sample mixture during the enzymatic pre-treatment process.

The system also comprises a calculation unit connected with the IR spectrometer, the calculation unit being adapted for calculating:

the ratio between specific species in the sample mixture based on the IR spectra of the sample, and/or the concentration of one or more specific species based on the IR spectra of the sample, and/or the degree of polymerization of one or more of specific species based on the IR spectra of the sample.

By the first and second aspect of the invention is thereby obtained a method and a system that can accurately determine the specific sugar molecules present in the solution and the average length of the sugar chains in real-time during e.g. a mashing process. Further information on e.g. the concentration of dissolved protein and free amino acids can also be obtained simultaneously.

The pre-treatment of crops prior to their fermentation in the process of making commercial grade ethanol, e.g. for the use as fuel, solvents or additives, is a process virtually identical to the mashing process used in the production of beverages or distilled liquors for human consumption as described above.

The feedstock for the fermentation process for making ethanol may include the same starch-containing crops as mentioned above for the mashing process, but also non-eatable crops or agricultural waste. A few non-limiting examples could be, willow, wood, bagasse or corn stover. In these types of crops, cellulose is a significant part of the sugar compound. Cellulose is a compound with a chemical structure almost identical to starch, where the conformation of the 1,4-glycoside bonds, which binds the glucose together, is oriented slightly different, giving the dissolved cellulose, cellulose oligomers and the analogous dimer cellobiose almost equal chemical and spectroscopic properties. Hence, the term "mashing" is also to be understood as including the similar enzymatic pretreatment of a starch or lignocellulose containing feedstock for fermentation in the production of commercial grade ethanol.

BRIEF DESCRIPTION OF THE DRAWINGS

FIG. 8b is an exploded view.

FIG. 12 shows the IR spectra of glucose, maltose, maltotriose and maltodextrin.

FIG. 22 shows the IR spectra following the in situ conversion of α-Glycopyranose.

DESCRIPTION OF PREFERRED EMBODIMENTS

Figure 1:
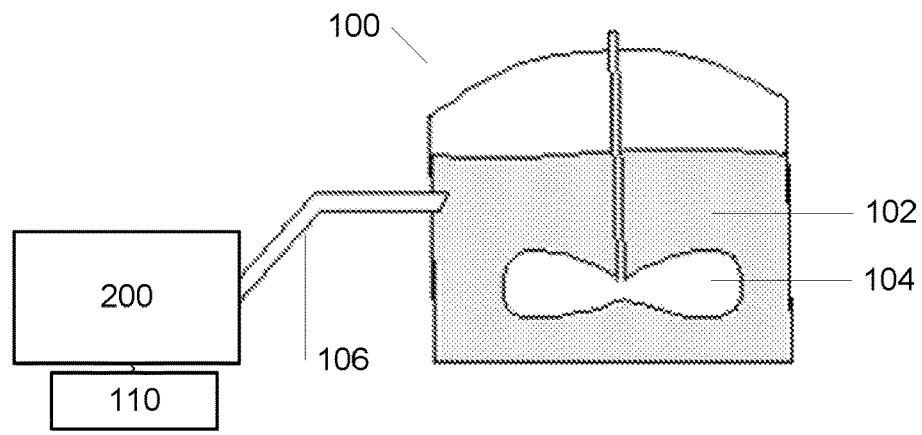
FIGS. 1, 2, 3a-b and 6a show embodiments of the mashing unit integrated with an IR spectrometer and a computer.

The present invention uses Mid infrared (MIR) spectrometers. These instruments operate in the Mid IR region, which is typically defined as being from 400 up to 4000 $cm^{-1}$. The absorptions of Mid-infrared brings the molecular bond in the irradiated sample to vibrate either through bending or stretching deformations. Each vibration type corresponds to the absorption of infrared light of one specific wavelength. The sum of all these vibrations and the corresponding absorptions of mid infrared photons at the respective wavelength results in a Mid-infrared spectra.

The position and intensity of each photon absorption and the corresponding vibration obey the rules of quantum mechanics, and can therefore be predicted and theorized using different approximations and models. Due to these mechanisms behind the mid infrared spectroscopy, no vibration in practice exceeds 4000 cm$^{-1}$. Also, for the purpose of this invention the interesting part of the spectra lies far below 3600 cm$^{-1}$.

The true infrared spectrometers used in this invention are often confused with Near infrared spectrometers, which despite the similar name are very different. Near infrared NIR spectrometers operates above the MIR wavenumbers, typically up to around 10000 cm$^{-1}$, or in some spectrometers all the way up to visible or UV wavelengths. None of the primary "true" vibrations are found in the Near infrared spectra, only overtones and combination bands of the actuals vibrations. The overtones are typically scrambled and much harder to use analytically and most often very different technologies are applied for the spectrometers themselves compared to MIR.

In the following description of the invention, the term IR will refer exclusively to Mid IR spectroscopy, and should not be confused with Near IR spectroscopy. It is very important for the present invention that it applies only to MIR and not to NIR, i.e. the two types of infrared spectroscopy are not to be confused.

The possibility to use infrared spectroscopy to analyze samples related to brewing has been evaluated in previous work for a laboratory environment for MIR as well as NIR (J. Tehnhunen et al., J. Inst Brew. volume 100 (1994) pages 11-15). The article measures samples of glucose, maltose and maltotriose and finds that especially ATR-FTIR is unsuitable to use in the real mashing/brewing analysis. Hence, the article focuses on NIR and transmission FTIR. The results of the works clearly shows that NIR is not useful in discriminating the components in their samples, and the errors are of significant larger magnitude than the factors the authors tries to identify in the samples. Transmission MIR is not technically relevant in the process as the highly toxic window materials that allows transmission in the fingerprint region, in the transmission cell will dissolve in the sample liquid. Further, the cell used has so narrow a pathlength that it would be technically impossible to use in a real brewing process.

In U.S. Pat. No. 4,913,914, a method to monitor the "maromi mashing" is proposed (for e.g. Soya Sauce production). "Maromi mashing" is a long fermentation process of soybean and rice that lasts from months to around a year, using koji-mold and lactic acid bacteria. Despite the linguistic similarity, the fermentation process of "maromi mashing" is very different from the mashing processes described in the present invention; as relatively fast enzymatic pretreatment. The patent describes the use of a near infrared spectrometer and an auto sampler system to monitor the mash fermentation process; not a true in-line analyzer. The defined NIR spectrometer works in an entirely different wavelength, where none of the molecular vibration described in the present invention can be found. As described in the background on MIR and NIR, it is essential to understand the difference between MIR and NIR spectroscopy. The discrimination of mono-, di- an poly-saccharides which is essential in the present invention is not mentioned.

DE4002108 (A1) discloses an automation of a well-known destructive method in starch analysis, where the starch helix structure can be identified by addition of iodine. The purple complex between amylase helix and iodine can then be quantified using a NIR-VIS spectrometer. The process consumes iodine and the sample cannot be returned to the mashing unit. It basically describes the automation of a well-known analysis, applying VIS-NIR spectroscopy in a another wavelength interval than the present invention.

WO2009/074650 discloses a method where unmalted cereals in combination with added enzymes, mainly amylases, is used as a substitution of malted barley and malted cereals in brewing. The invention describes mechanisms of the mashing or brewing that are well known to any person skilled in the art of brewing, but does not describe, in any terms, how to use infrared spectroscopy to monitor the process.

EP0851027A1 discloses a method using ATR-FTIR spectroscopy to control lactic acid bacteria in fermentation processes. The invention describes how to control lactic acid bacteria, through monitoring the two forms of lactic acid (protonated and deprotonated), and how they can be quantified using ATR, making the method useful at different pH values. The process also describes how to control lactic acid bacteria through the intensity of "alcoholic signals" from glucose. However, the discrimination of mono- and poly-saccharides is not mentioned. The quantification of glucose using ATR-FTIR alone is straight forward and not surprising in itself. The method does not describe an apparatus for the analysis in-line, or the use of ATR-FTIR to control an enzymatic pre-treatment.

The present invention comprises a methodology where attenuated total reflectance (ATR) infrared (IR) spectroscopy is applied in real-time to monitor enzymatic pre-treatment processes such as e.g. mashing processes. By ATR-IR spectroscopy is meant spectroscopy, where the IR spectra between 400-3500 cm$^{-1}$ is measured. Simultaneously with the measurements of the IR spectra, a computer calculates an accurate composition of the components in the solution, i.e. the mash, and returns biochemical key values to the operator or to a control system, which overall allows for a better control and optimization of the mashing procedure. Examples of such important key values are the ratio between mono, dimeric and polymeric sugar compounds, the total concentration of dissolved sugars, and the concentration of proteins or important flavoring compounds. Further parameters may also be monitored.

In one or more embodiments the method comprises the step of stopping the enzymatic pre-treatment process when a predetermined ratio between the specific species in the sample mixture is obtained, and/or the concentration of one or more of the specific species reached a predetermined level, and/or the degree of polymerization of one or more of the specific species reached a predetermined level. The enzymatic pre-treatment process may either stopped manually by the user or automatically by the system on basis of the information provided from the calculation unit.

In one or more embodiments, the sample mixture is stirred during at least part of the enzymatic pre-treatment process.

In one or more embodiments, water is added to the sample mixture during the enzymatic pre-treatment process, e.g. together with the possible addition of the one or more enzymes.

In one or more embodiments, the temperature in the sample and/or sample mixture is increased and/or is decreased either prior to starting the enzymatic pre-treatment process, during the enzymatic pre-treatment process, and/or in order to stop the enzymatic pre-treatment process.

In one or more embodiments, the enzymatic pre-treatment process is stopped by the system opening the tank automatically, or alternatively by removing the sample mixture from the tank. Also, the enzymatic pre-treatment may be stopped by increasing the temperature in the tank. The enzymatic pre-treatment process is normally stopped when the predetermined ratio between the specific species in the sample mixture is obtained, and/or when the concentration of one or more of the specific species reaches a predetermined level, and/or when the degree of polymerization of one or more of the specific species reaches a predetermined level.

In one or more embodiments, the sample is selected from natural occurring carbohydrates in e.g. cereals and other starch and di- and polysaccharide containing crops such as e.g. barley, wheat, rye, oat, corn, rice, potatoes, straw, wood, starch and corn stover.

In one or more embodiments, the enzymatic pre-treatment process is a mashing process conducted prior to a fermentation process such as brewing.

In one or more embodiments, multiple enzymes are added to the sample mixture either at the same time or at different times and wherein the temperature of the sample mixture is adjusted during the pre-treatment process to account for different temperature levels at which each of the multiple of enzymes are most active.

In one or more embodiments, the IR spectra are measured at wavelengths between 400-3000 $cm^{-1}$, between 400-2000 $cm^{-1}$, between 500-1500 $cm^{-1}$, between 700-1400 $cm^{-1}$, or between 800-1300 $cm^{-1}$.

In one or more embodiments, the analyzing unit is an ATR-IR cell adapted for containing a small part of the sample mixture during measurements of ATR-IR spectra of the sample mixture during the enzymatic pre-treatment process, wherein the ATR-IR cell is mounted tightly to an ATR-IR plate comprising a crystal, the ATR-IR plate being part of an ATR-IR spectrometer, where the tight mounting is obtained by means of a clamp on the ATR-IR spectrometer and an O-ring positioned between ATR-IR plate and the analyzing unit.

In one or more embodiments, the system further comprises a connection unit connecting the tank and the analyzing unit, the connection unit being adapted for guiding a small part of the sample mixture from the tank to the analyzing unit whereby ATR-IR spectra of the sample mixture is measured by the ATR-IR spectrometer.

In one or more embodiments, the system comprises an extraction probe which protrudes inside the tank for extracting a small sample part for the IR spectra measurement at a user-determined position inside the tank.

In one or more embodiments, the analyzing unit is a spectroscopic unit comprising an ATR-IR unit, a spectrophotometer for measuring IR spectra, and a computer, wherein the ART-IR unit comprises an ATR-IR plate with a crystal.

In one or more embodiments, the spectroscopic unit is attached directly to a wall of the tank.

In one or more embodiments, the spectroscopic unit is connected to the wall of the tank by connecting means e.g. in the form of a set of hoses.

In one or more embodiments, the ATR plate can be turned up to 90 degrees around its own axis.

FIG. 1 shows a setup comprising a mashing unit 100 with a solution 102 containing products to be mashed and possibly the enzymatic solution/compounds which are to be added into the feedstock products. In the embodiment shown in FIG. 1, an ATR-FTIR (Attenuated Total reflectance Fourier Transform Infrared) probe using a waveguide principle 106, is inserted directly into the mashing unit 100. The IR spectra are collected and sent to a computer unit 110, which deconvolutes each IR spectrum. The area of bands characteristic to the total sugar/starch content as well as the bands specific to the polymeric sugar compounds can be extracted from the spectra. The relevant band areas are then used to calculate the concentration of individual polymeric sugar compounds and a ratio between monomeric and polymeric sugar compounds using premade calibration curves. Further values like protein content, and free amino acid content may also be reported simultaneously.

The mashing unit 100 also comprises a stirring unit 104, which may be a propeller or similar as illustrated in FIG. 1. An infrared (IR) spectroscopy measurement apparatus 200, e.g. an Attenuated Total Reflectance (ATR) IR spectrometer, is coupled directly to the mashing unit 100 via an optical connection path 106, e.g. a setup comprising mirrors or similar optical components for guiding the IR light from the IR spectrometer 200 to the sample 102 and for guiding the back-reflected light from the sample 102 and to the IR spectrometer 200.

The IR spectrometer 200 is in turn connected to a computer 110 or similar data processing device, which calculates the individual sugar compounds and the ratio between monomeric and polymeric sugar compounds—possibly along with the protein and/or free amino acid content—in real time.

Figure 2:
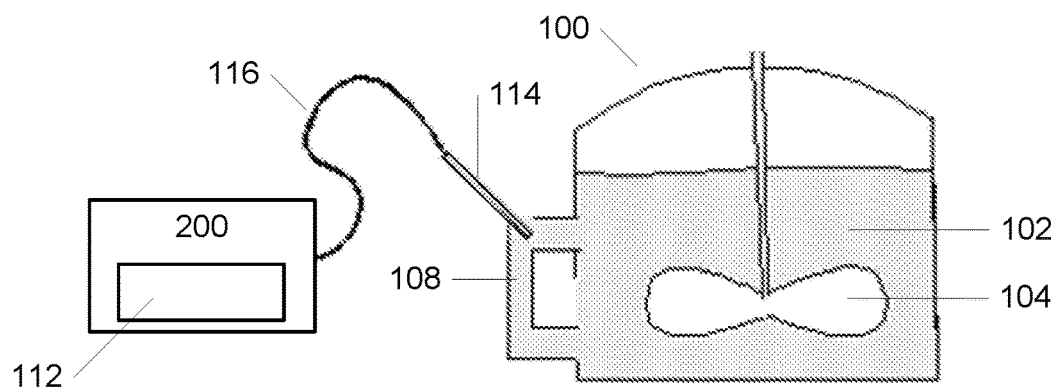

In another embodiment as shown in FIG. 2, a fiber 116 optical FTIR probe 114 is inserted into a side channel 108 of the mashing tank 100 where it collects IR spectra continuously. In a variation of this embodiment, the computer 110 is integrated into the cabinet of the spectrometer 200, which performs multivariate data analysis on each spectrum and shows the relevant values directly on a display 112 on the spectrometer 200.

Figures 3A, 3B:
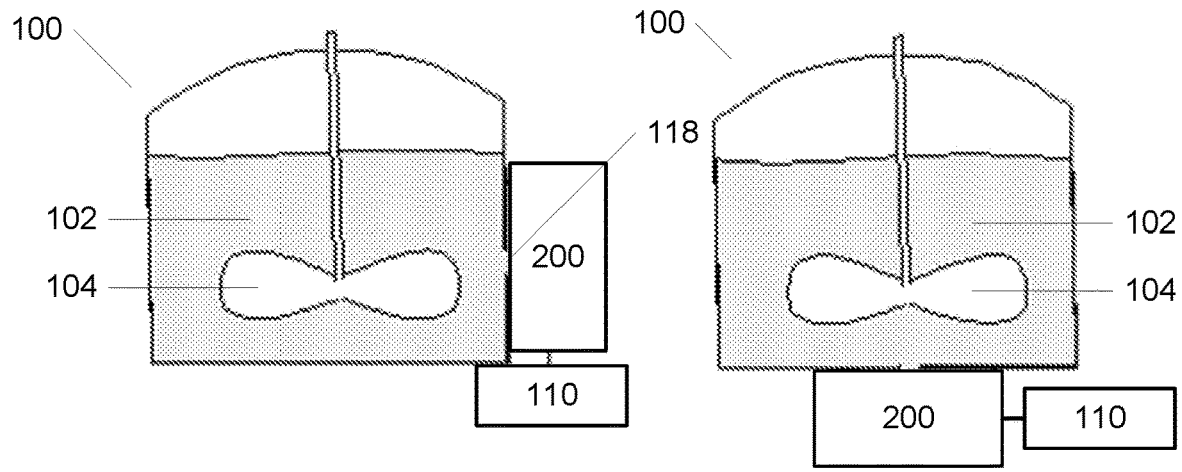

In an embodiment similar to the one shown in FIG. 1, an FTIR spectrometer 200 is equipped with an ATR-cell which is mounted directly on the mashing tank 100. In this way, the product 102 being mashed and an ATR crystal in the ATR-cell interact intimately through a hole 118 in the tank 100. The position of the IR spectrometer 200 on the tank 100 can be either on the side or at the bottom of the tank as shown in FIG. 3a and FIG. 3b, respectively.

A valve may be used for allowing the extraction of sample 102, i.e. the mash, from the mashing tank 100. By using either a pumping unit, the pressure in the inside the mashing unit 100 or gravity, a sample may be sent to the IR spectrometer 200, e.g. a Fourier Transform (FT) IR spectrometer, positioned adjacent to the mashing tank 100. The FTIR spectrometer equipped with a customized ATR-Unit can thereby measure and record IR spectra of the solution 102 being mashed. Such sample extraction may be operated either as a continuously flow, or sample aliquots may be extracted at preferred times during the mashing process. A specific embodiment of such a customized ATR unit utilizing an ATR-cell and a special add-on analyzing chamber is shown in FIGS. 4 and 5.

Figure 4:
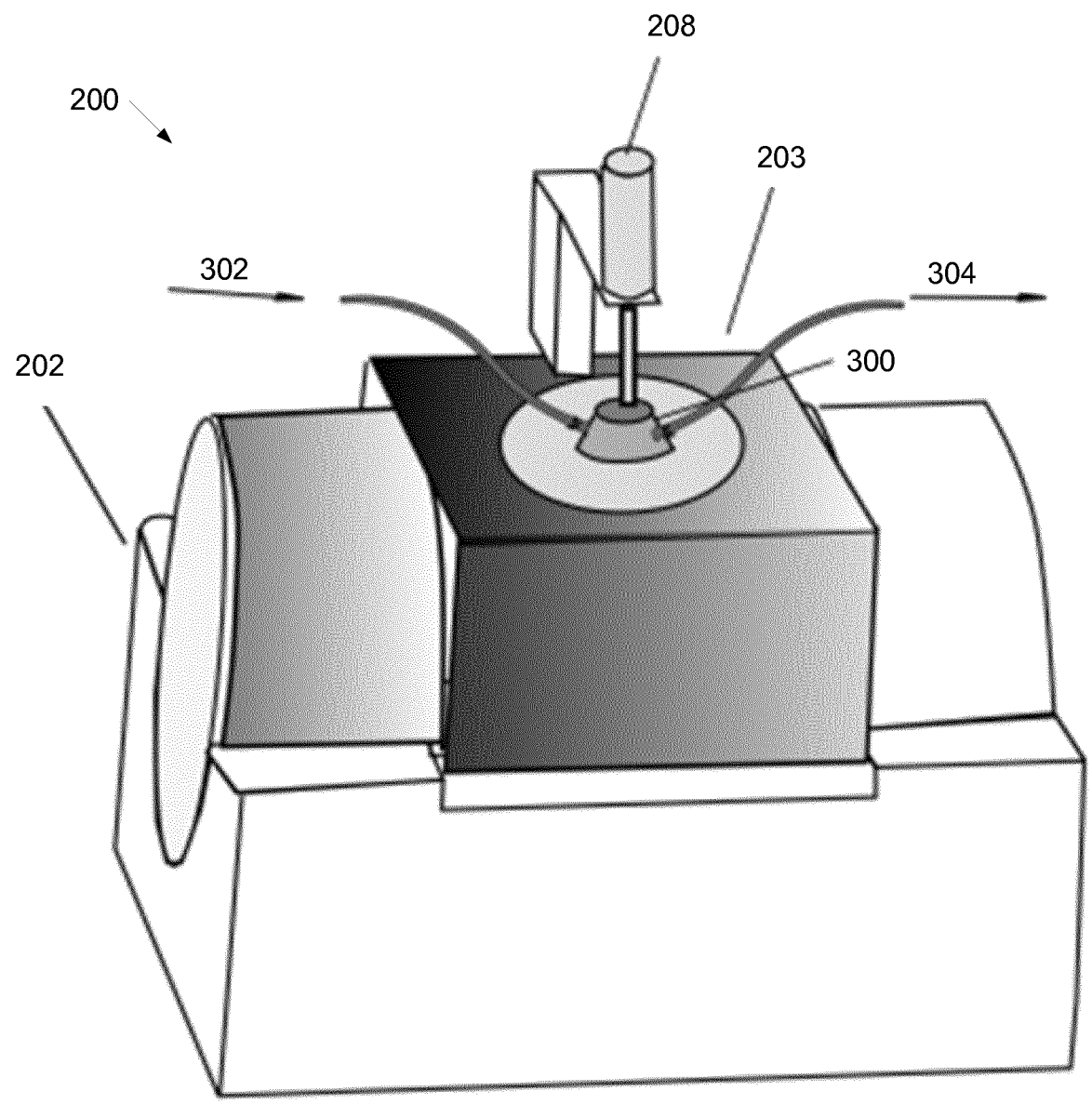
FIGS. 4 and 5 show an IR spectrometer from the outside and the inside (FIG. 4 and FIG. 5, respectively).
Figure 5:
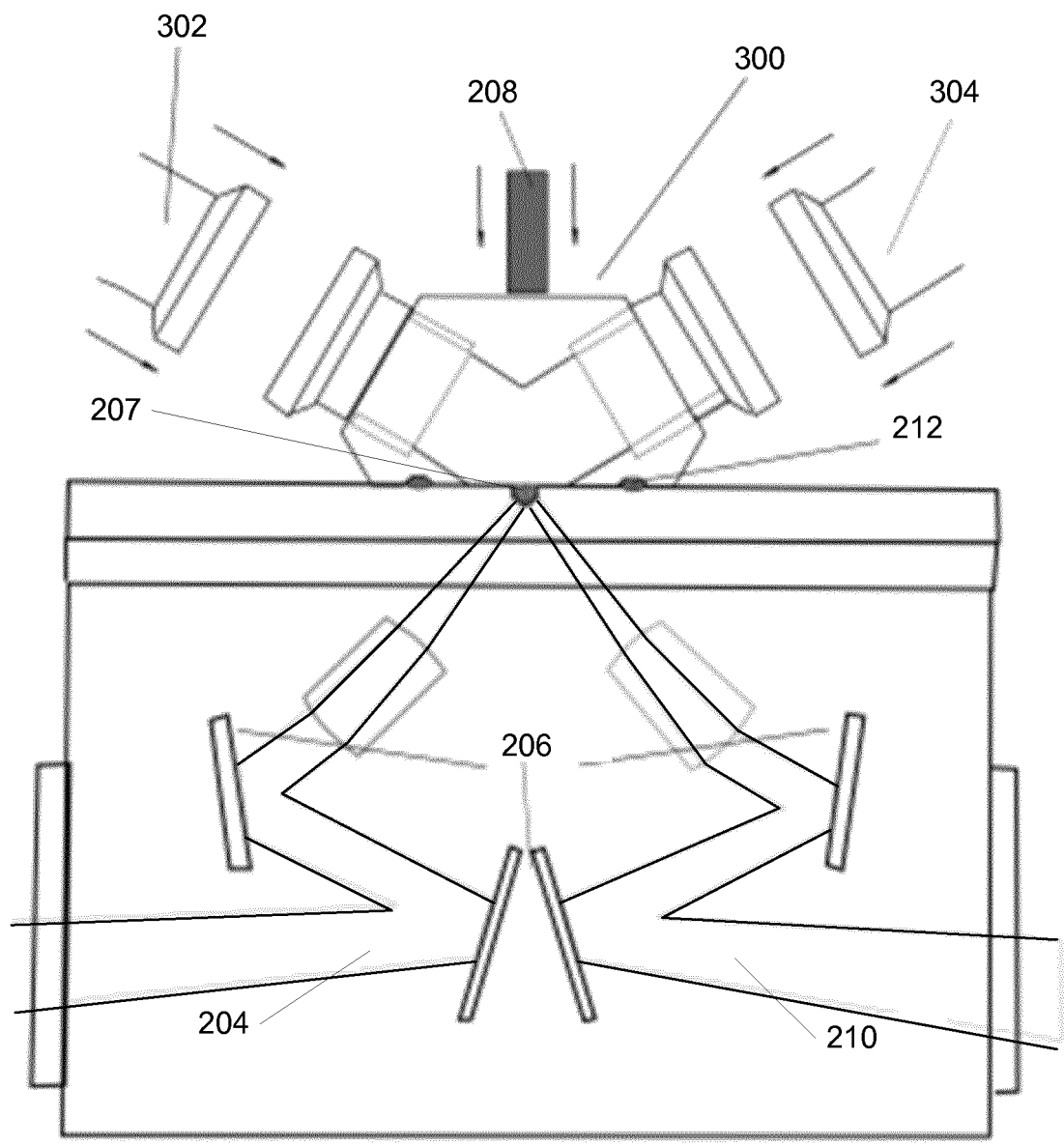

FIG. 4 shows the IR spectrometer 200 seen from 'outside' and FIG. 5 shows a view 'inside' part of the spectrometer 200 and an analyzing chamber 300 where the sample is lead to. The IR spectrometer comprises a box 202 where the IR light is produced and an ART-IR unit 203. The incoming IR light 204 is guided via a set of optical components 206, e.g. mirrors, to a crystal 207 for obtaining intimate contact with the sample inside the analyzing chamber 300. The reflected IR light 210 is likewise guided away from the crystal 207 to a unit inside the spectrometer 200 for analyzing the spectra.

The analyzing chamber 300 may e.g. be an ATR-IR cell possibly being an add-on device and is normally secured to the spectrometer 200 by a clamp 208 normally being an integrated part of the spectrometer 200. A tight sealing between the analyzing chamber 300 and the spectrometer 200 is normally obtained by using an O-ring 210, which ensures that the liquid sample stays inside the analyzing chamber 300. The sample is guided into the analyzing chamber 300 by a connector inlet 302 and guided away again by a connector outlet 304. The connector inlet and outlets 302, 304 may be releasable connected to the analyzing chamber 300.

In one or more embodiments, an analyzing chamber 300 is built permanently together with the ATR-unit 203 by the manufacturer. In other embodiments, the ATR-unit 203, analyzing chamber 300 and spectrometer 200 are all fully integrated into one combined unit.

After each IR spectrum measured by the spectrometer 200, the sample in the analyzing chamber 300 is discarded as waste or returned into the mashing tank 100.

The IR spectra are analyzed by customized software that extracts band areas from the collected spectra and converts them to relevant values, such as sugar contents, average length of sugar polymers, dissolved protein content and its degree of hydrolysis, concentration of flavoring compounds such as diacetyl, ester compounds or bitter compounds etc.

An advantage of the spectrometer 200 combined with the analyzing chamber 300 described above is that it may be calibrated independently of the operation of the mashing tank 100.

Figure 6A:
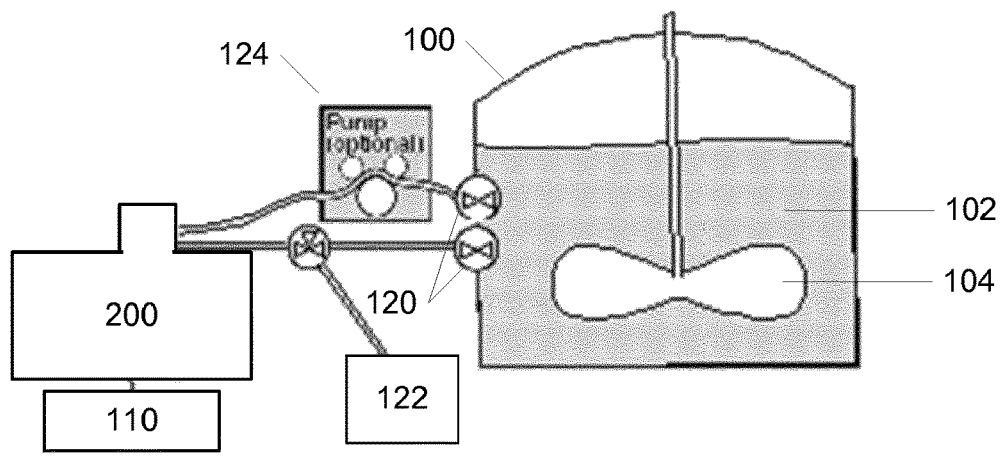

In FIG. 6a it is illustrated that the tank 100 may have extraction and recirculation valves 120 at the inner wall of the mashing tank 100 and a waste tank 122 for through a valve disposing samples after the IR spectrum of the sample has been measured. The setup may also be equipped with a pump unit 124 for recycling the sample 102.

Figure 6B:
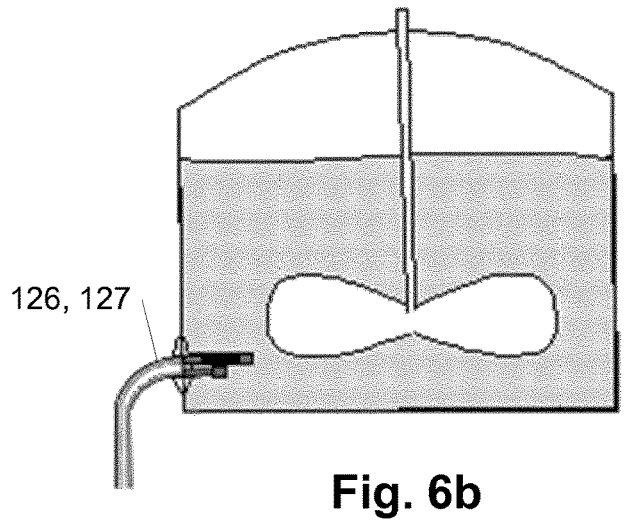
FIGS. 6b-d show embodiments of the mashing unit.
Figure 6C:
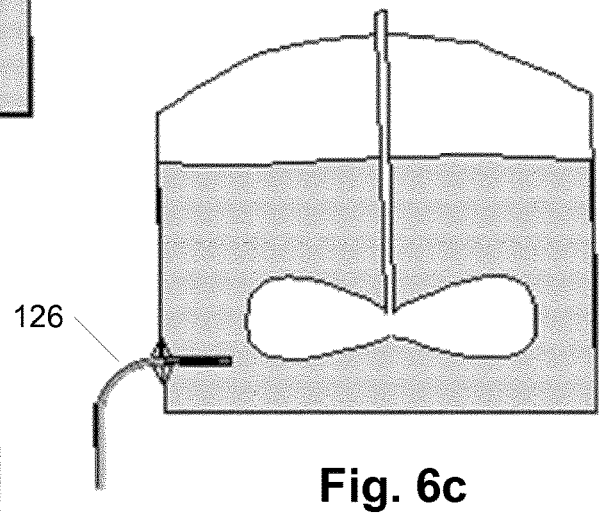
Figure 6D:
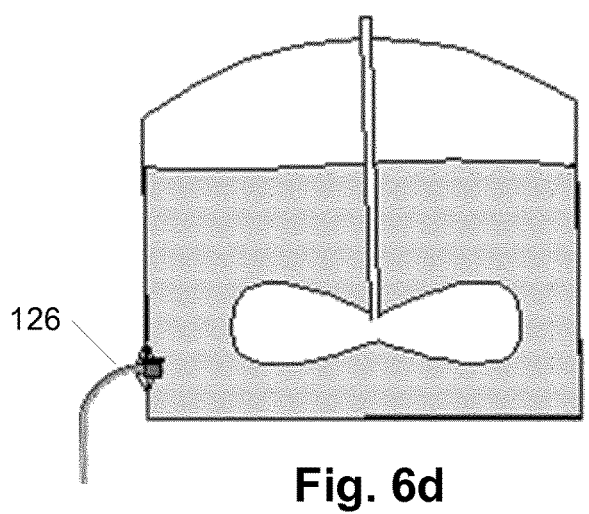

In one or more embodiments, extraction 126 and/or recirculation probes 127 may be positioned close to or in connection with the valves 120 as is illustrated in FIGS. 6b-6d. Some none limiting examples of extraction probes 126 are shown in FIGS. 7a-d.

In one or more embodiments, an automatic cleaning system may be used to clean the analyzing chamber 300 when the mashing tank 200 is not operating. The automatic cleaning system may function by pumping a flow of cleaning agents or chemical such as bases, acids or organic solvents trough the analyzing chamber 300, and rinsing with water. Calibration standards may further automatically be pumped into the analyzing chamber 300 when the mashing tank 200 is not operating to run a calibration program.

Figure 7A:
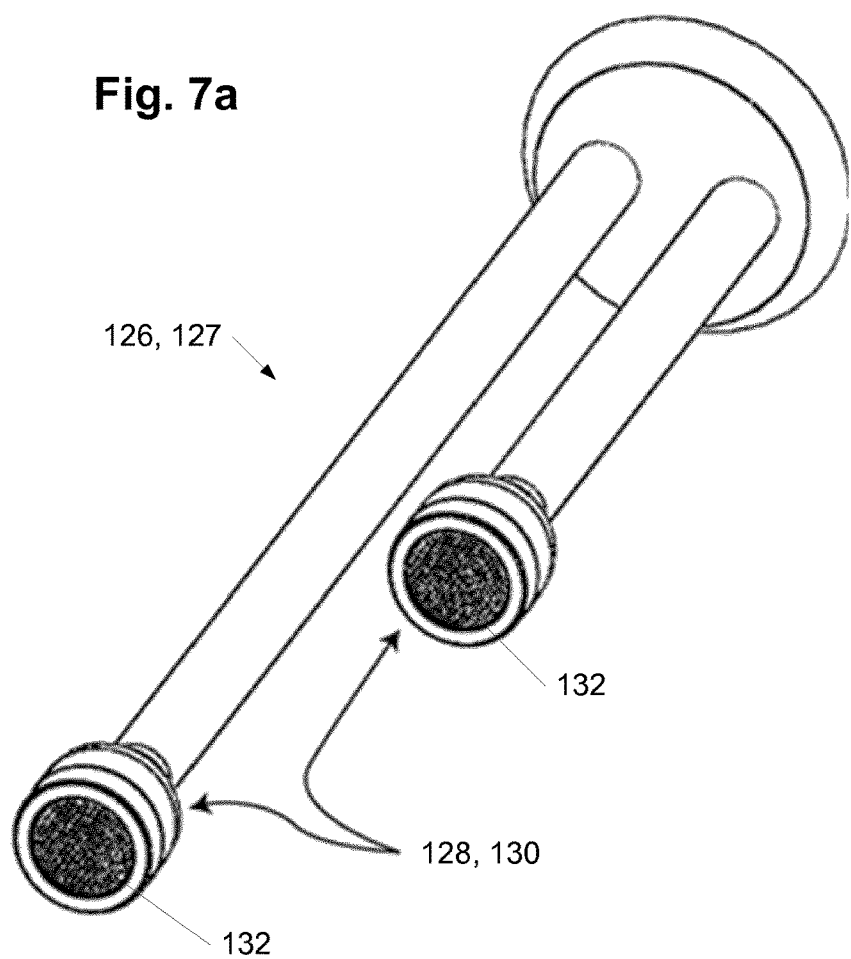
FIGS. 7a-d show embodiments of extraction and/or recycling probes.

The inlet 128 (and possible outlet 130 as shown in FIG. 7a) in the extraction probes 126 is dimensioned to allow large particles to flow freely through the probe 126 without plugging the system. In one or more embodiments the extraction probe 126 is fitted with a filter 132 to constrain particles too large for the rest of the system. In another variation, the probe is designed with a removable filter so the mask size can be changed. A filter may also be omitted as shown in FIG. 7c.

In one or more embodiments, a part 134 of the extraction probe 126 extends into the mashing unit 100 to extract the liquid sample from a desired location in the mashing tank 100. The extraction probe 126 will normally be connected to the tank 100 by a vessel mount 136.

Figure 7B:
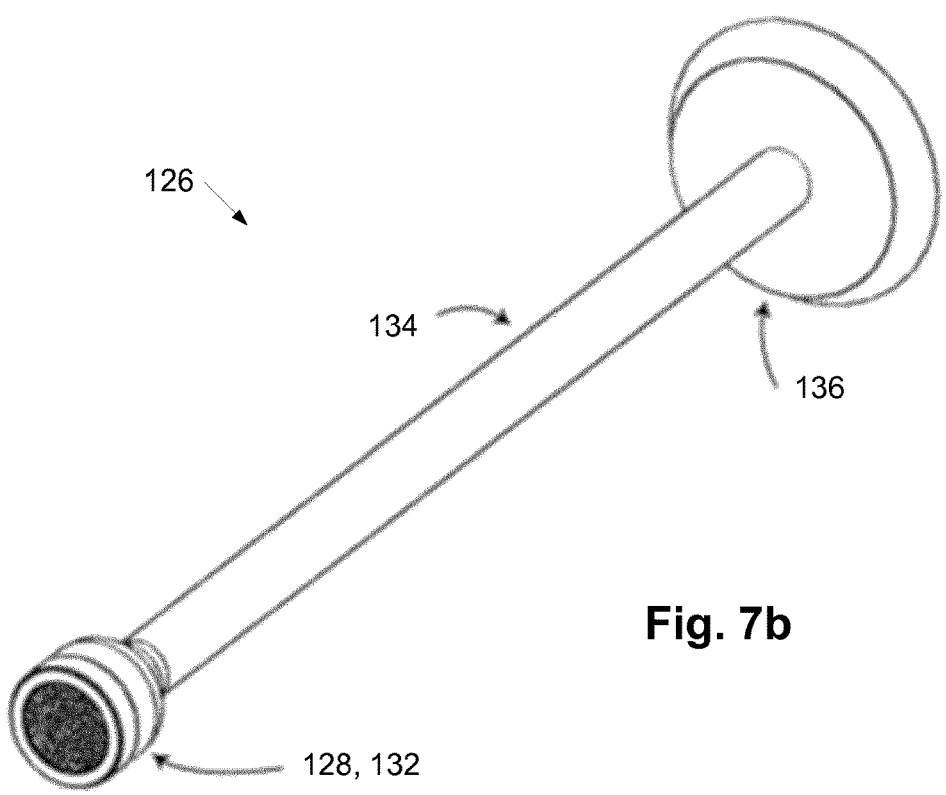
Figure 7C:
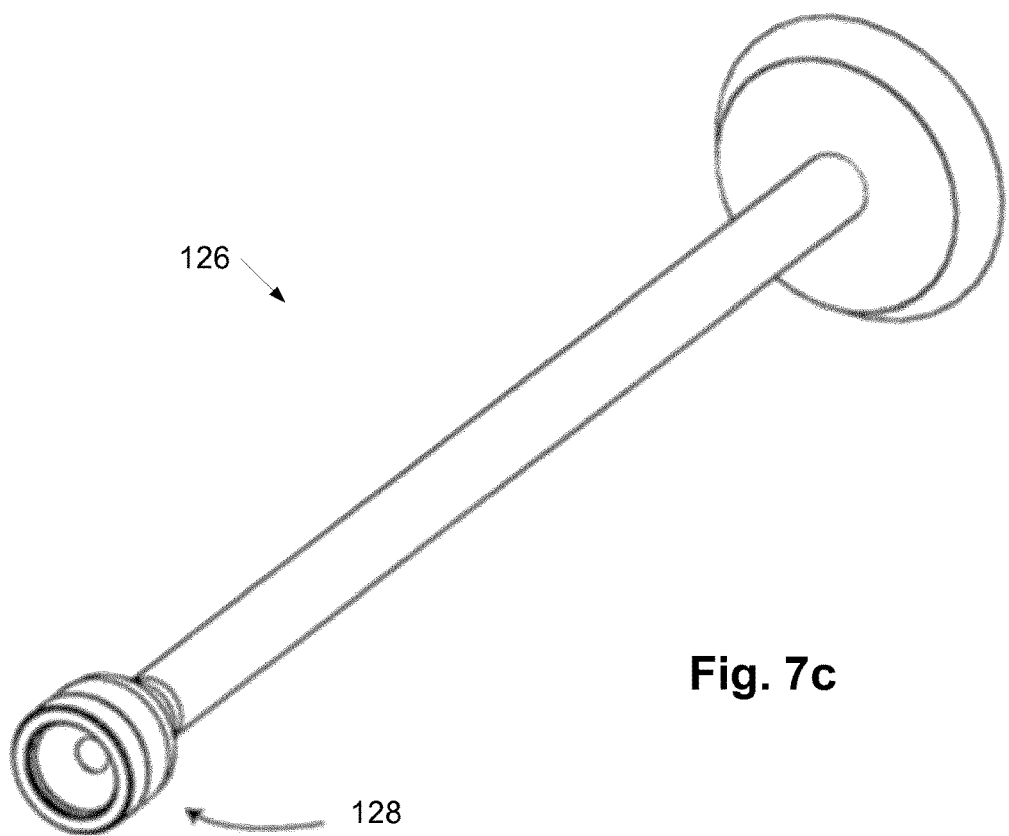
Figure 7D:
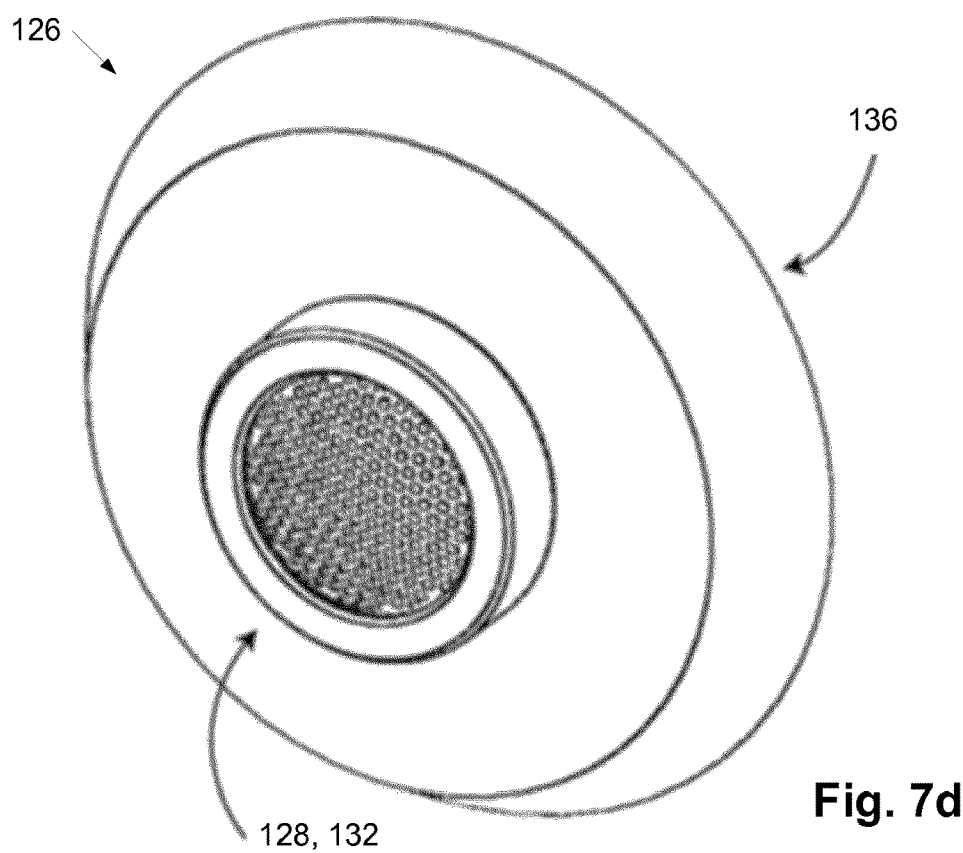

In one or more embodiments, the extraction probe 126 may act as a valve on the inner wall of the mashing tank (a non-limiting example is shown on FIG. 7d).

The extraction probe 126 shown in different versions in FIG. 7a-c may extract samples from different locations in the mashing tank 100. This may be done by using a series of valves connected to a tube inside the mashing tank 100. In yet another variation the extraction probe 126 may use motors to extend and change location inside the mashing tank 100.

As shown in FIG. 7a, the probe may comprise of two individual probes: an extraction probe 126 and a recirculation probe 127, where one is for inlet 128 of the sample and one for outlet 130 to allow flow back into the mashing tank 100. By using a pump applied to the system, the direction of the flow in the system may be changed to prevent clumping in the filters. In this way, the two individual probes (extraction probe and recirculation probe) may be combined to a double probe handling both in- and outlet.

The extraction probe 126 may be inserted into the mashing tank 100 using a mount inside de mashing tank 100. The mashing tank mount allows easy installation and maintenance of the probe 126. The mount may utilize tri-clamp connections to connect a tight seal between the probe 126 and the mashing tank 100.

The mount seals may also be created by using a vacuum between the probe 126 and the mashing tank 100. Alternatively, the mount may be welded onto the wall of the mashing tank 100.

Figure 8A:
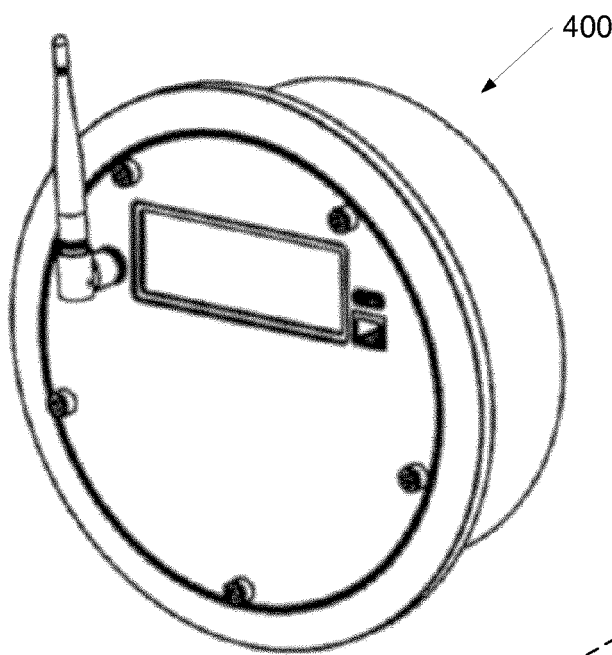
FIGS. 8a-b show a spectroscopic unit, where
Figure 8B:
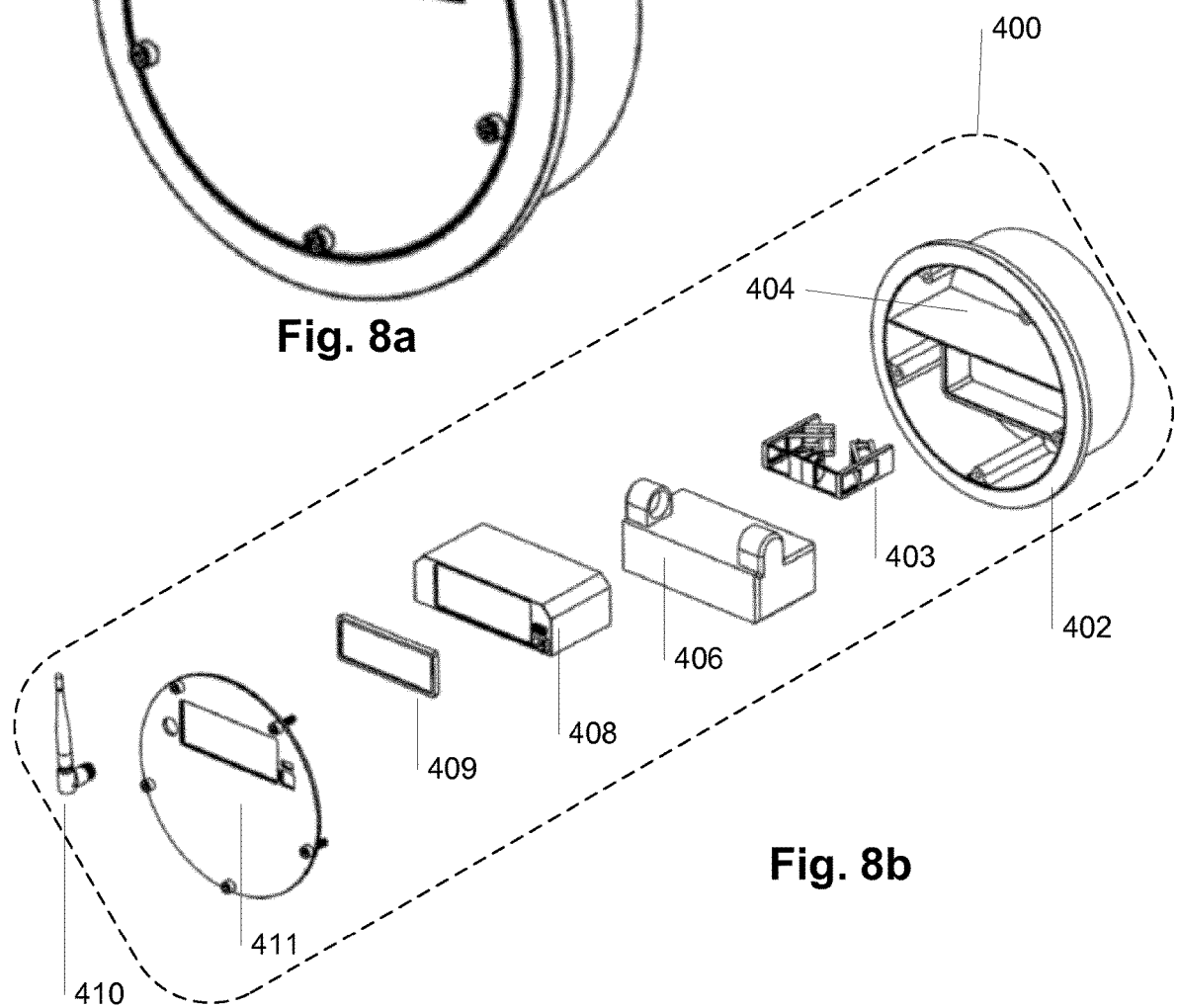

FIG. 8a show an IR spectroscopic unit/analyzing unit 400 according to the invention and FIG. 8b shows the spectroscopic unit 400 in an exploded view. The spectroscopic unit 400 comprises a spectroscopic enclosure 402 with a plate 404 in which a crystal 407 is mounted, The crystal 407 must be in contact with the media in order for the spectroscopic unit 400 to perform IR measurements. An IR spectroscopic constellation is used to direct Infrared light through the crystal 407. In the embodiment shown in FIGS. 8a-b this is done by using a spectroscopic unit 400 with a spectrophotometer 406 and an ATR-IR unit 403 consisting of either mirrors or optics to direct the light from an emitter in the spectrophotometer 406 through the crystal 407 and back into a receiver in the spectrophotometer 406.

The emitter may receive IR light from an external light source by means of guiding optics and/or mirrors or fibers. Alternatively, the spectrophotometer 406 may contain a diode array emitting IR light inside the spectrophotometer 406. The receiver may likewise guide the back reflected light to an external spectrometer or in itself contain diode receivers.

Figure 10A:
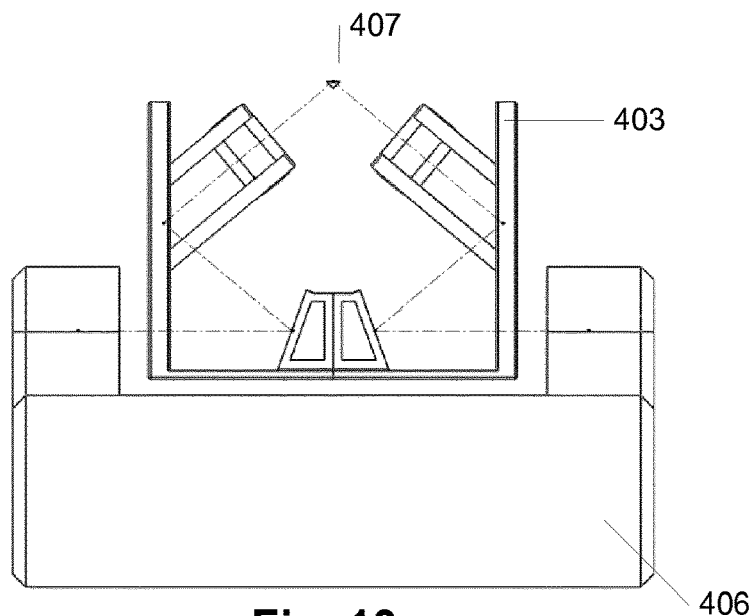
FIGS. 10a-b show a close-up of a spectrophotometer and an ATR unit and FIG. 10c shows a close-up of a spectrophotometer combined with only a crystal.
Figure 10B:
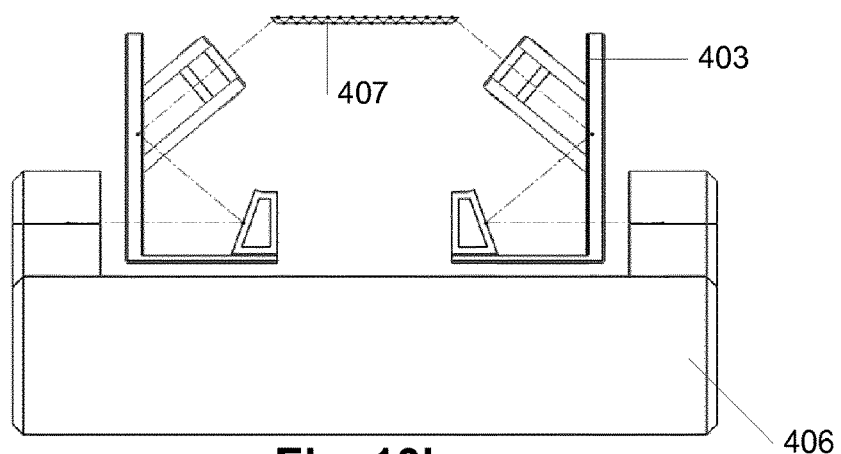

In an embodiment, the crystal 407 will only cause the light to bounce through the media once (single bounce) as shown in FIG. 10a, while in another embodiment the crystal 407 will cause several bounces through the media (multi bounce) as shown in FIG. 10b.

Figure 10C:
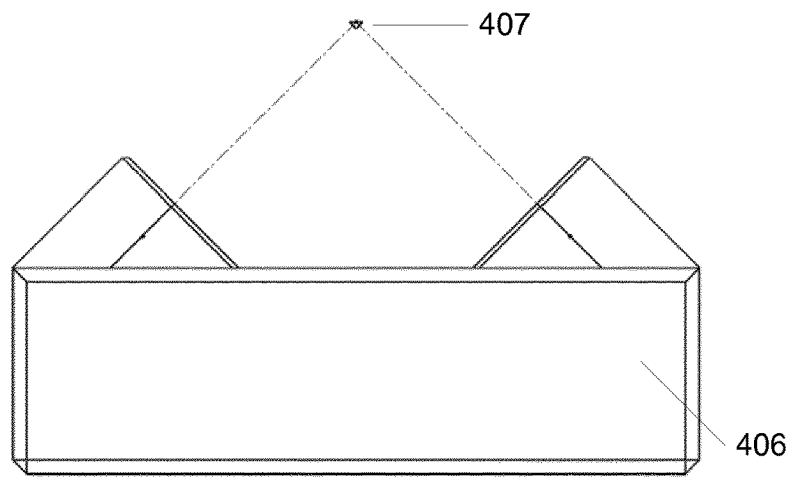

In another embodiment the ATR unit 406 is neglected and the emitter and receiver are angled towards the crystal 407 creating a direct path to and from the crystal 407 as shown in FIG. 10c.

In another embodiment the receiver is replaced by a photo sensor and filter.

The spectroscopic unit 400 further comprises a computer 408 connected to the spectrophotometer 406 for performing the necessary data treatment before the data is sent back to the user or to a central control system, e.g. a tank control system connected to the tank. The computer 408 may be connected to an antenna 410 for wireless communication. Alternatively or as a supplement, the computer 408 may be connected to a display 409 for direct interface with the user. The spectroscopic unit 400 also comprises a lid 411.

In order to perform spectroscopic measurements on a media, the spectroscopic crystal 407 must be in contact with the media. This can be done e.g. as in-line measurement, where the spectroscopic unit 400 is mounted directly on a tank, vessel or pipe.

Figure 11A:
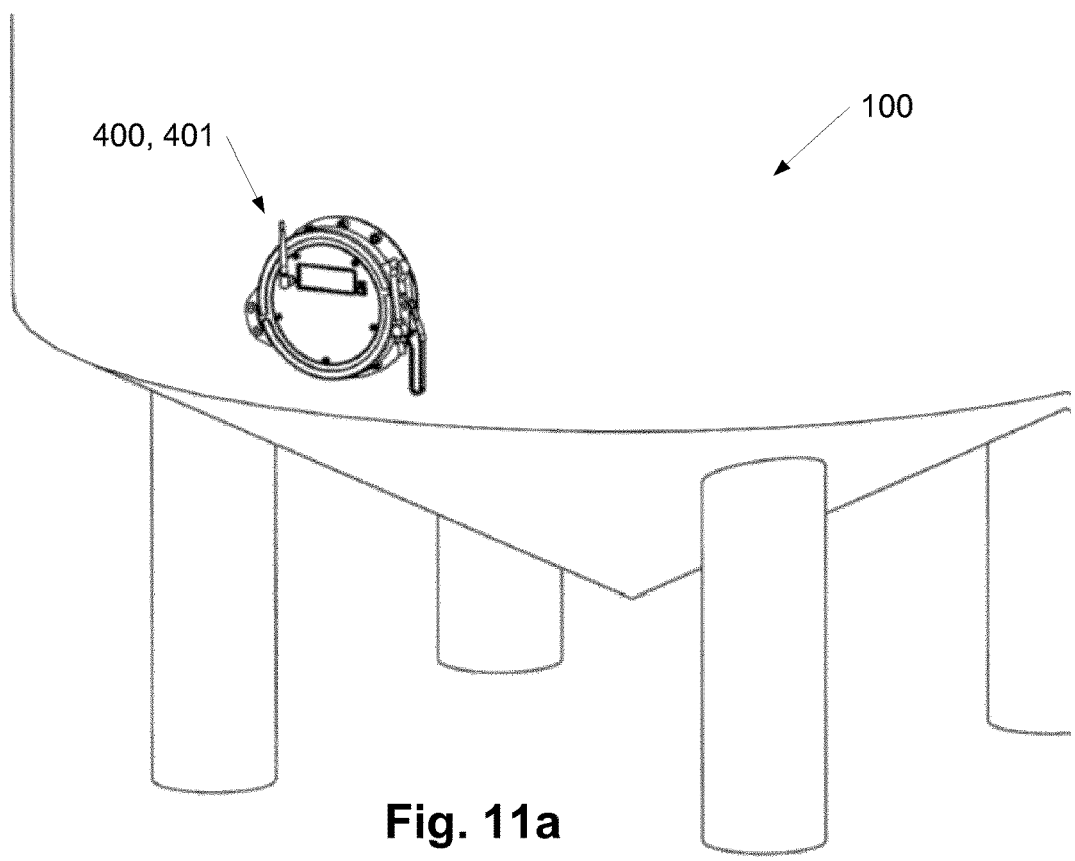
FIGS. 11a-b show a first embodiment where the spectroscopic unit of FIGS. 8a-b is connected with a tank and FIGS. 11c-d show a second embodiment where the spectroscopic unit of FIGS. 8a-b is connected with a tank.
Figure 11B:
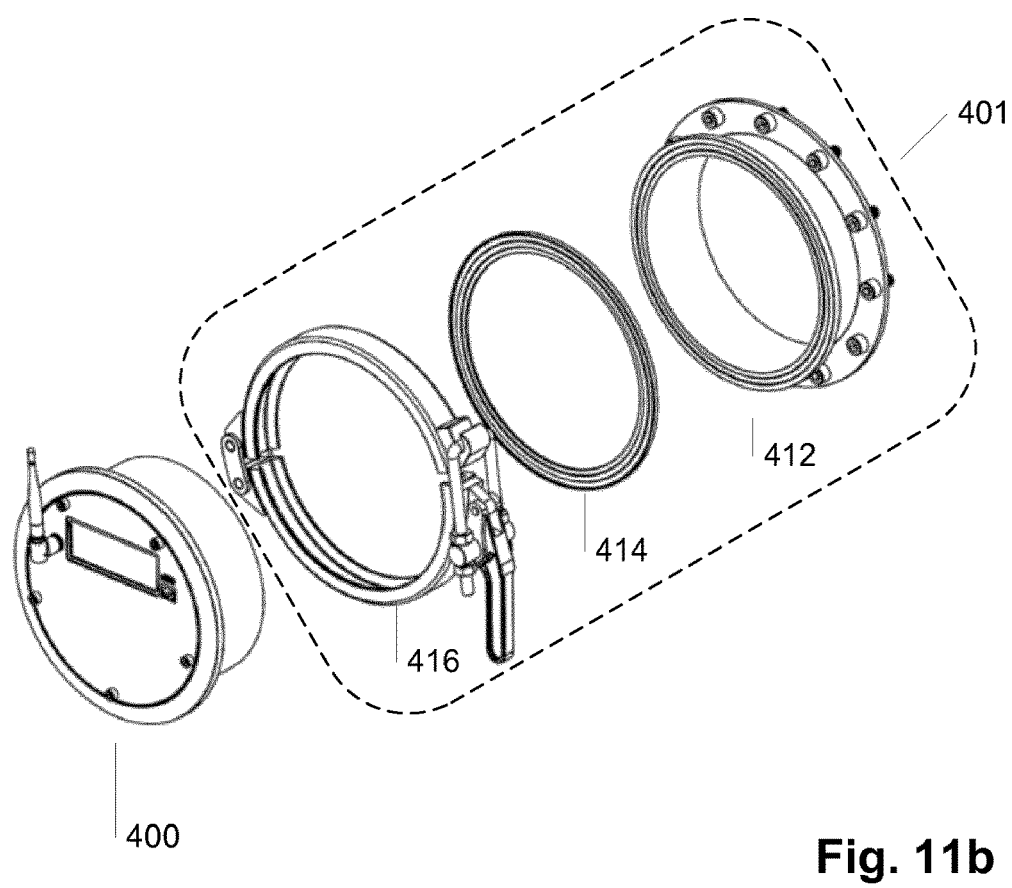

FIGS. 11a-b shows an embodiment of an in-line system comprising a tank, e.g. a mashing unit 100 with the IR spectroscopic unit 400 attached directly to the side of the mashing unit 100. The spectroscopic unit 400 is mounted to the mashing tank 100 using a sealed mount unit 401 to keep the crystal 407 in contact with media while preventing any leakage. The sealed mount unit 401 comprises a tank mount 412, a clamp 416 to tightening the connection between the spectroscopic unit 400 and tank mount 412 and a seal 414 for sealing the connection between the spectroscopic unit 400 and the tank mount 412.

The mount 412 may be placed on the side of a vessel/tank 100 as shown in FIG. 11a, on the bottom or top of the vessel/tank 100.

Figure 9A:
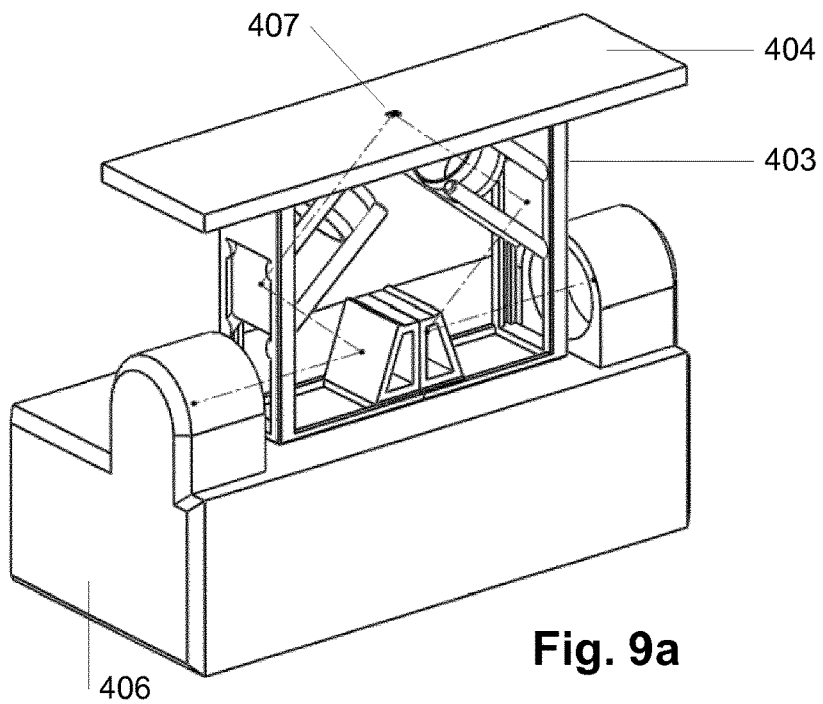
FIGS. 9a-c show a close-up of a spectrophotometer and an ATR (Attenuated Total Reflectance) unit.
Figure 9B:
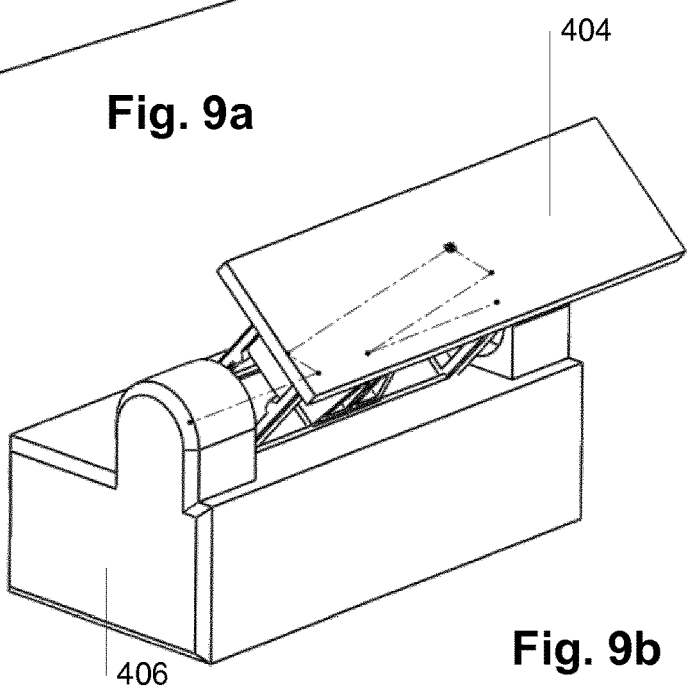
Figure 9C:
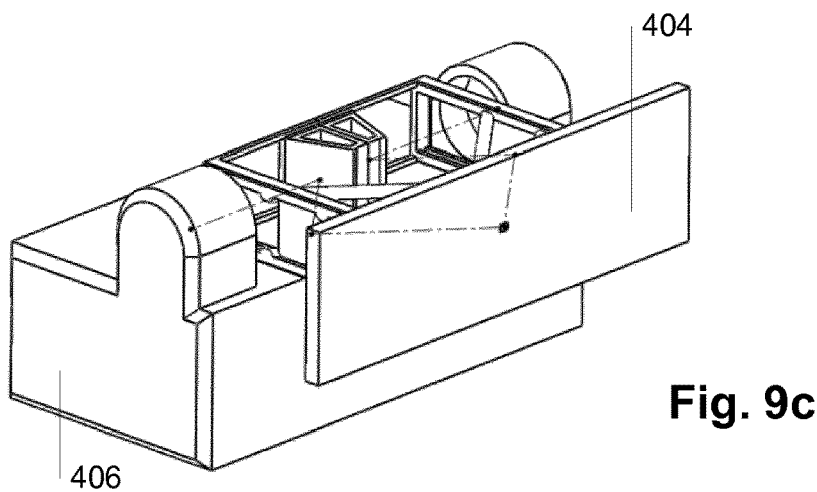

When sample residue is left on the crystal 407 when the spectroscopic unit 400 is not in use, the residue solidifies and the ATR unit 403 must be cleaned prior to new measurements. In an embodiment shown in FIGS. 9a-c, the surface, in which the crystal 407 is embedded, is tilted to allow the sample to drain off the crystal 407. In FIGS. 9a-c, a 45 degree tilt is shown in FIG. 9b compared to FIG. 9a and a 90 degree tilt is shown in FIG. 9c.

In one embodiment, the entire spectroscopic unit is drained to allow drainage. In another embodiment, a tilting base is implemented between the spectrometer and the ATR unit allowing the ATR unit to tilt along the axis of the IR beam. In an embodiment, the tilting base is adjustable to tilt to a desired degree. In an embodiment the tilting base is motorized allowing it to tilt additionally between measurements.

Figure 11C:
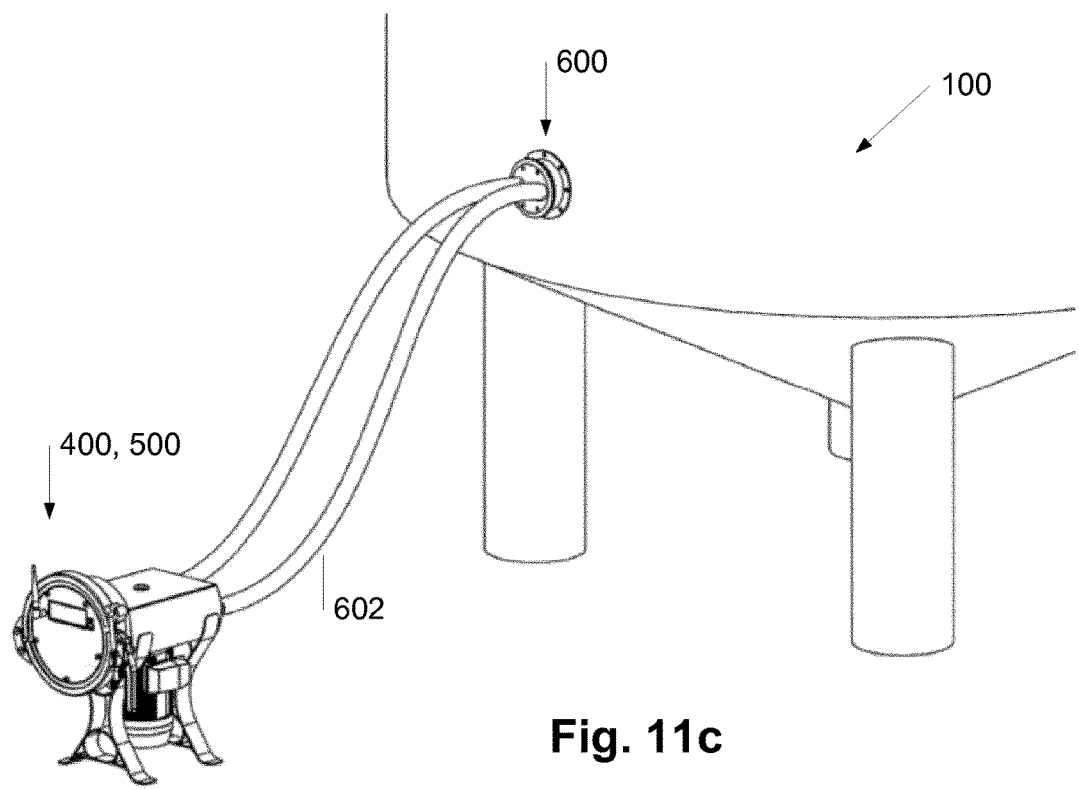
Figure 11D:
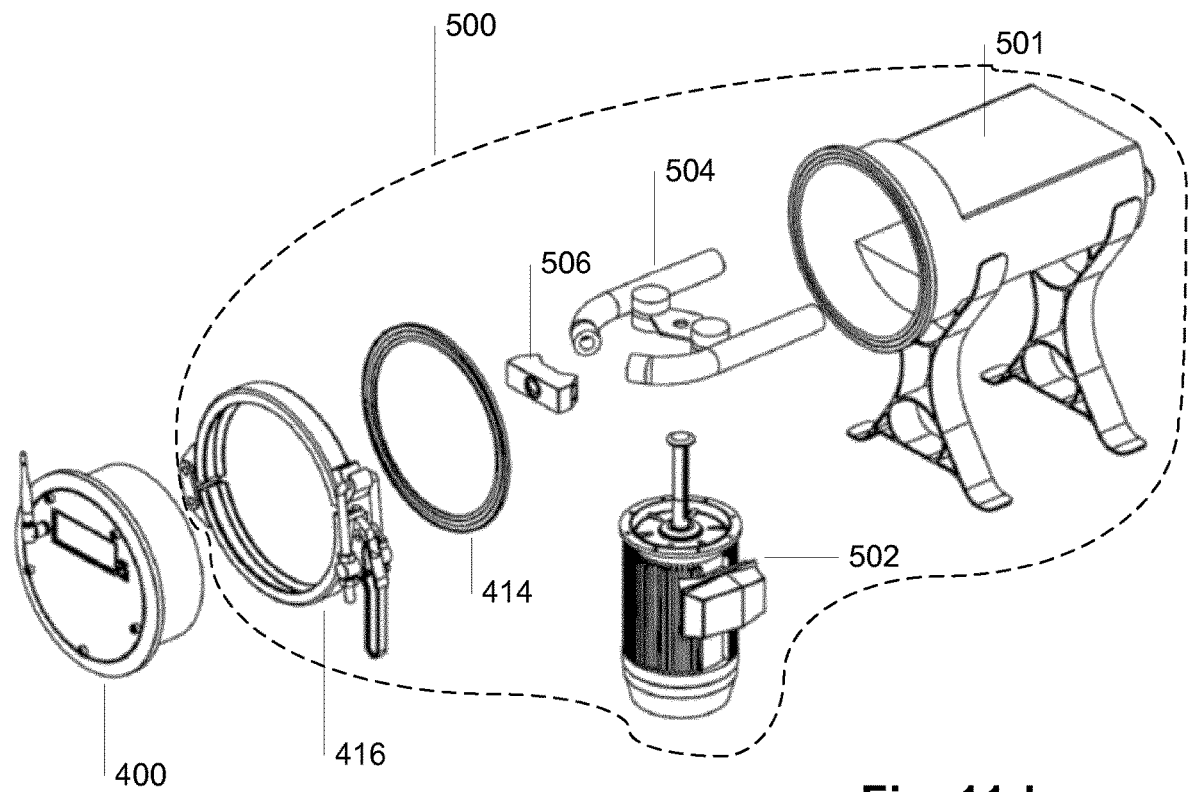

Another method for keeping the crystal 407 in contact with the media is using an at-line setup as shown in FIGS. 11c-d. In this embodiment, the spectroscopic unit 400 is mounted to a pumping unit 500 and connected to a filtration unit mounted on the tank 100 via hoses 602. The two hoses 602 may be replaced by pipes.

The filtration unit 600 may be a simple filter screen. Alternatively, the filtration unit 600 may be replaced by a tank mount 412 as shown in FIGS. 11a-b. Yet alternatively, the filtration unit 600 may consists of probes reaching into the tank or vessel 100.

The pumping unit 500 comprises a peristaltic pump system with a housing 501, a motor 502, a pump head 504 utilizing media displacement to move the media to and from the vessel 100, and a flow cell 506 for directing media across the crystal 407. The flow cell 506 is connected to the pump 504 to ensure proper flow across the surface of the crystal 407. The pumping unit 500 also comprises a seal 414 and a clamp 416 for obtaining a tight seal between the spectroscopic unit 400 and the pumping unit 500.

In an embodiment, the pumping unit 500 is placed on the floor. In another embodiment the pumping unit 500 is mounted to a wall or the vessel itself.

The invention may be explained through the following non-limiting examples:

Example 1

Figure 23:
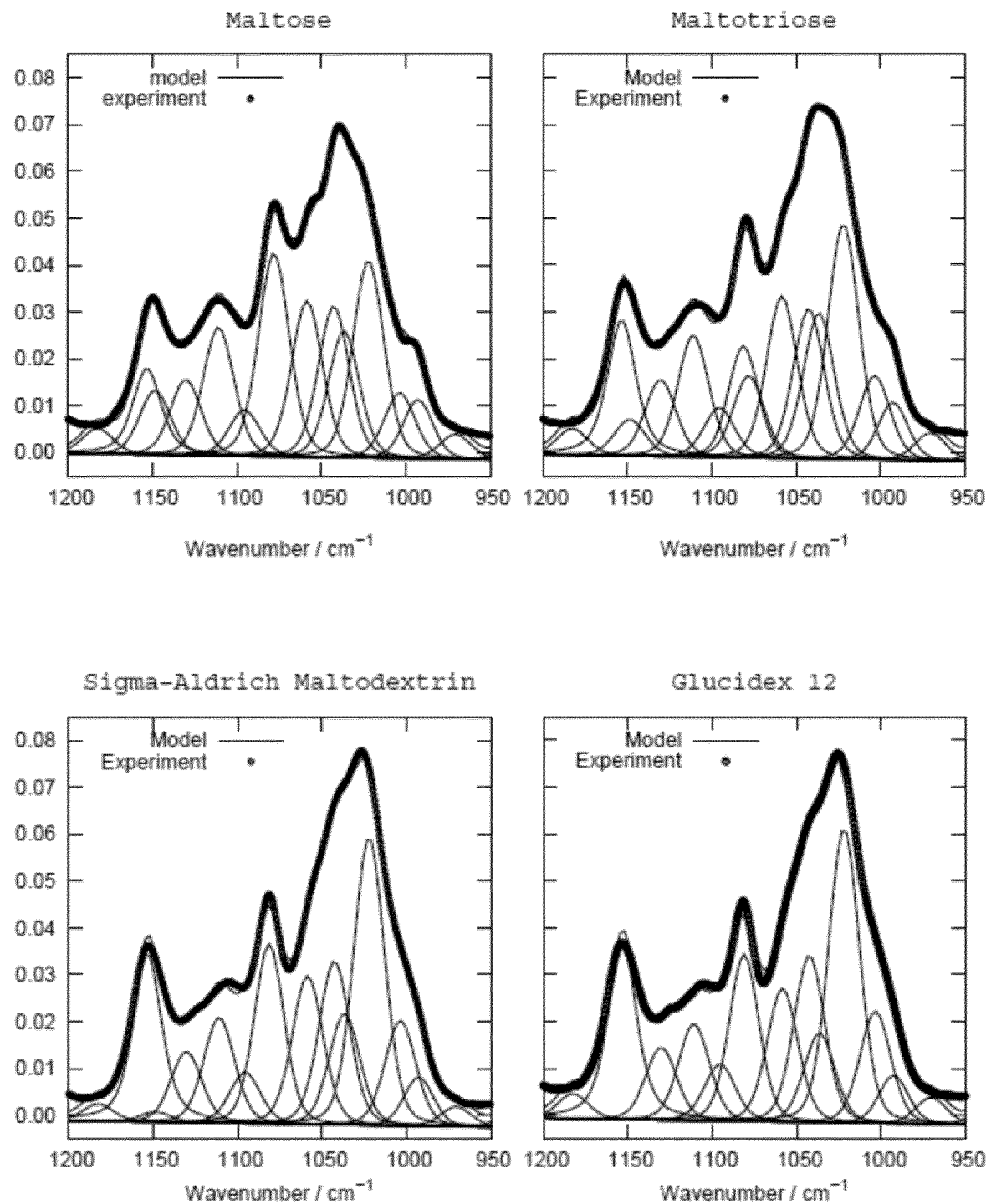
FIG. 23 shows the spectra of four different carbohydrates and the deconvolution of each spectrum.
Figure 25:
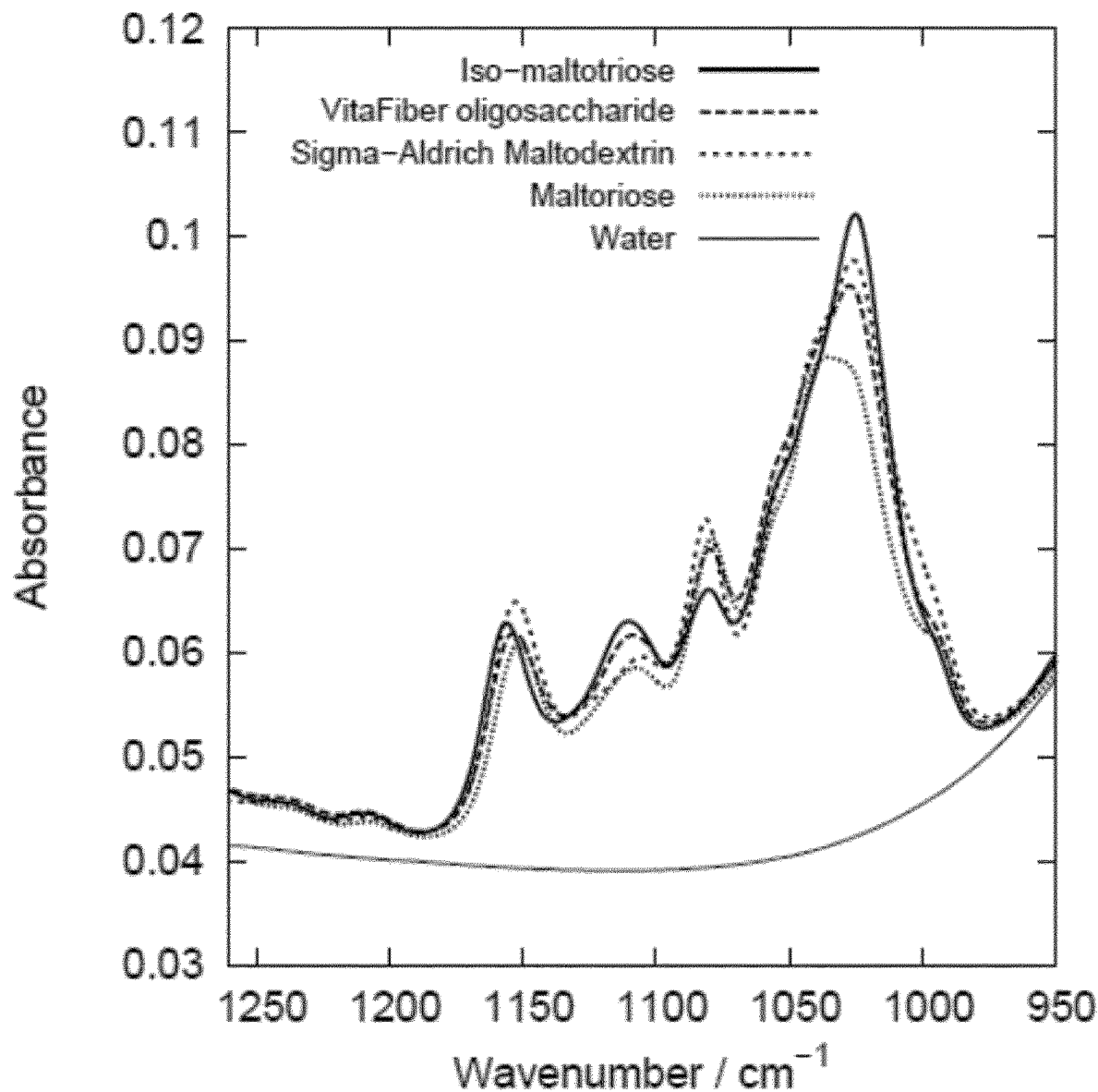
FIG. 25 shows the spectra of different α-(1,4) glycoside bond containing compounds.

Aqueous solutions of respectively 5% w/w of glucose, maltose, maltotriose and maltodextrin are prepared and IR spectra of all the solutions are recorded. These spectra can be found on FIG. 12. The bottom line in FIG. 12 shows the spectrum of pure water for comparison. The IR spectra are originating from vibrational modes in each compound. The relatively large change in the infrared spectra of the four compounds that are almost chemical identical, shows that the changes mostly originates from the polymeric 1,4-glycoside bond. FIGS. 23 and 25 further shows measurements of the same species as shown in FIG. 12.

The glycoside bond itself has a characteristic antisymmetric C—O—C stretching mode that gives a band at around 1160 cm$^{-1}$. However due to the overlap of the C4-O stretching in glucose and the terminal C4-OH groups on the polymers, it is not suitable to distinguish between monomeric and polymeric species.

Figure 13:
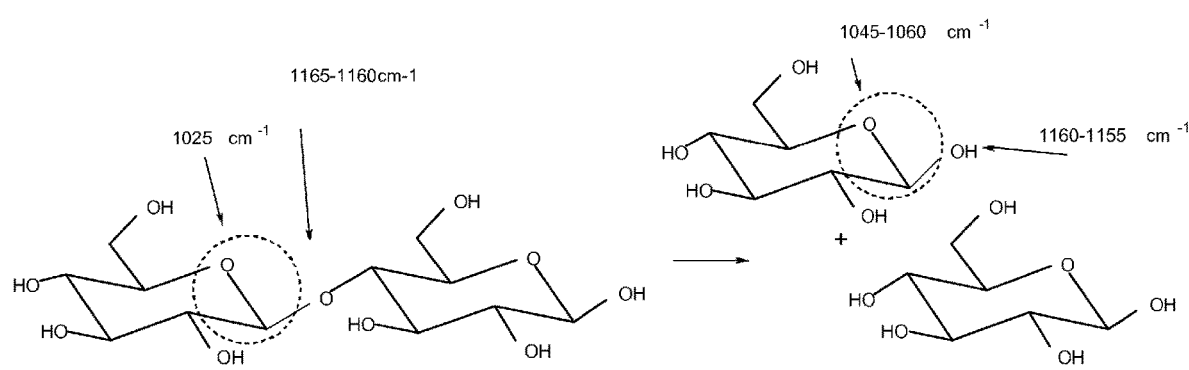
FIG. 13 shows the characteristic vibrations of the glycoside bond and the acetal group in the starch related di- and polymers- of glucose, as well as the related modes in the monomeric glucose analog.

However the acetal group, which is a consequence of the glycoside bond, induces more significant difference in the spectra seen by the pronounced decrease of intensity of the band at 1026 cm$^{-1}$ upon depolymerizing—see illustration of this process in FIG. 13. Hence the disappearance of the 1026 cm$^{-1}$ band is a good indicator for depolymerization.

Like other forms of transmission spectroscopy Lambert Beers Law applies to ATR-FTIR spectra, the law reading:

$$A = \varepsilon * I_{penetration} * c \qquad [1]$$

where A is the absorption, $\varepsilon$ is the extinction coefficient, $I_{penetration}$ is the penetration depth of the infrared beam, and c is the concentration of the compound causing the absorption.

The penetration depth is constant when using ATR-FTIR for samples with similar refractive index, which means that the height or the area of each band is proportional with the concentration of the compound that causes the band.

The characteristic vibrations of the acetal group is so characteristic for the polymeric band, that it can be used for accurate quantification of the total glycosides bands per glucose unit in the mixture of different sugar lengths. One way of measuring the abortion could be just subtracting the spectrum of pure water from each spectrum and reading the peak height at around 1020-1030 cm$^{-1}$, where vibrations from the acetal group is observable. However due to overlap with neighboring bands a multivariate data analysis will improve the accuracy of the method significantly.

Figure 14:
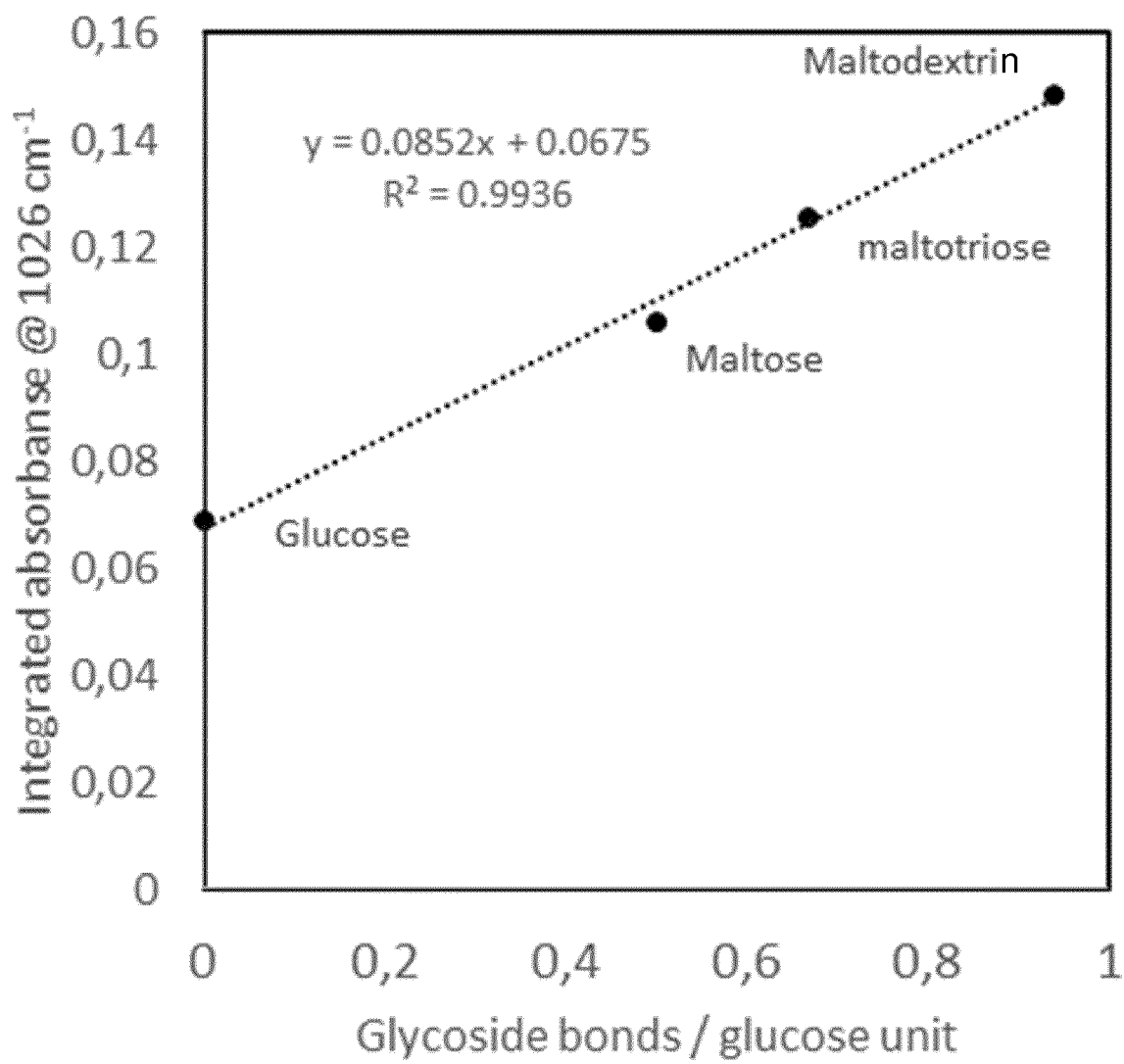
FIG. 14 shows the integrated absorbance of the band at 1026 $cm^{-1}$ as a function of glycoside bonds per glucose unit for the IR spectra of glucose, maltose, maltotriose and maltodextrin.

The area of the 1026 cm$^{-1}$ band is therefore extracted using Gaussian deconvolution. As an alternative, variations of multivariate data analysis could also have been used. The results showing the integrated absorbance at 1026 cm$^{-1}$ as a function of glycoside bonds per glucose unit are plotted at FIG. 14 for the four spectra shown at FIG. 12. FIG. 14 clearly demonstrates how accurate the method is to discriminate and identify the glycoside bonds, even at low concentrations.

Example 2

A slurry of 3.5% w/w powdered starch in water is prepared and heated to 90° C. for 5 minutes resulting in a homogenous gel like solution. The solution is then injected into a 5 mL vessel that is attached directly on top of the ATR-plate, the vessel is designed in such a way that the ATR crystal and the solution have intimate contact. Then the solution was stirred by an external stirring device at room temperature, while spectra were continuously recorded. To simulate a mashing process, a solution of a-amylase was added to the solution. Hereafter the total absorption from sugar compounds increased, due to better solubility of the shorter-chain starch molecules, but the intensity stabilized within few minutes. The spectra in the 1200-900 cm$^{-1}$ region started to change significantly, and the bands intensity of the 1030-1020 bands decreased significantly over time, indicating depolymerization of the starch, see spectra at FIG.

Figure 15:
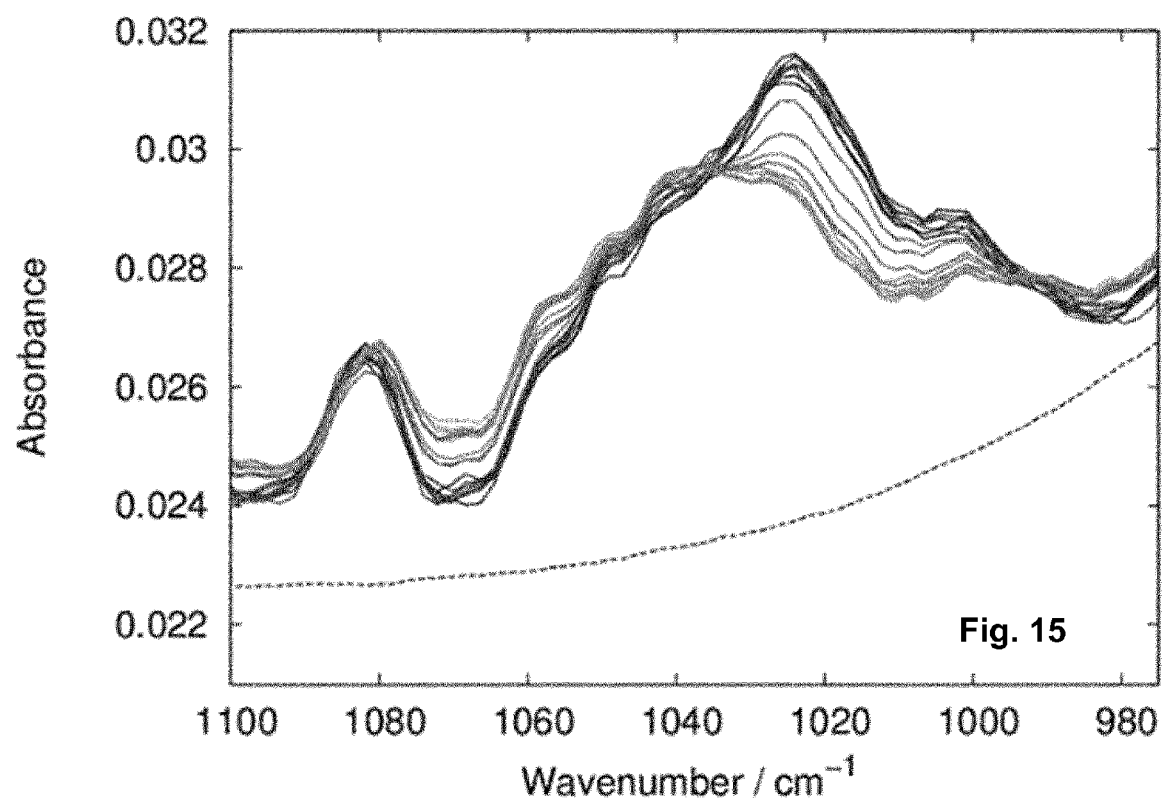
FIG. 15 shows IR spectra measured during the mashing process of starch.

15, where the dark lines represent early time and the grey lines represents the spectra after longer and longer time as the lines becomes more and more grey. The bottom dotted line in FIG. 15 shows the spectrum of pure water for comparison.

After around 30 minutes, there were no further changes in the spectra indicating that the enzymatic process had almost stopped. Comparing the spectrum (light grey) with that of maltose and maltotriose in FIG. 12, it is clear that the solution now consist of a mixture of maltose and maltotriose.

Example 3

0.1 g of protein extracted from barley is mixed with one gram of water and heated gently at 60° C. for 15 min. The resulting slurry is stirred in a small vessel on top of an ATR-FTIR unit. This allows intimate contact between the slurry and the diamond of the ATR unit, while IR spectra are recorded continuously. The spectra shows a characteristic absorption (slightly overlapping) from the amide groups of 1690 $cm^{-1}$ and 1550 $cm^{-1}$, respectively, the C=O stretching band and the N—H bending band. After some time a 0.1 mL solution containing protease enzyme is injected into the vessel. After the enzyme injection, the band at 1690 $cm^{-1}$ shifts upwards to around 1705 $cm^{-1}$. While the band at 1690 $cm^{-1}$ is characteristic for the carbonyl stretching at the peptide bond in the protein group, the 1705 $cm^{-1}$ band is characteristic for free amino acid dimers or a corresponding terminating amino acid group in a short protein fragment. The individual area of the 1690 and the 1705 $cm^{-1}$ bands can clearly be resolved using deconvolution of the spectra and is used to calculate the dynamic a ratio of (dissolved protein)/ (free amino acids) throughout the protease treatment.

Example 4

60 kg of coarsely ground malted barley and 200 L water is loaded into a 250 L stainless steel container supplied with a boiler unit for heating and a mechanical stirring device. At the bottom of the tank, an electronic controlled valve is connected for sample extraction. Before the valve is a coarse filter preventing the larger particles to pass through the valve. During operation, the valve is opened so a peristaltic pump may extract samples from the tank though the valve.

The sample liquid is pumped into a chamber attached on top of a golden gate diamond ATR unit (see drawing at FIG. 4-5). IR spectra are constantly recorded with 30 second intervals. Initially the barley is heated to 37° C. and maintained at this temperature for 20 minutes. Afterwards the mash is taken to 60° C. for 20 minutes, and then to 65° C. for 40 minutes.

At first, the total signal from sugars increases due to dissolution from the malt into the mash, but at elevated temperatures the areas of the intensity of the bands in the 1030-1020 $cm^{-1}$ region start to decrease significantly. The spectra are deconvoluted simultaneously with the real time recording of the spectra and on the basis of the areas of characteristic bands in the deconvoluted spectra and pre-obtained calibration curves, a ratio between fermentable sugars and maltodextrins is obtained. When the mash contains the preferred ratio between fermentable sugars, the temperature is quickly raised to 75° C. denaturing the amylases and thereby stopping the mashing at the optimal composition.

Example 5

A reactor is loaded with 1000 kg of peels from potatoes and 2000 L of water. Then the resulting mixture is heated to 100° C. for 10 minutes and cooled to 50° C. At this temperature, valves are opened in the bottom and the top of the tank and the mixture is allowed to circulate through a side channel 108 in the reactor creating a loop similar to that shown in FIG. 2.

Among other probes, a fiber based ATR-FTIR diamond probe is located in this side channel. The probe is connected to an adjacent FTIR unit, which at this time starts to record spectra of the liquid passing through the side channel. The temperature is maintained at 50° C. and commercial grade amylose powder is added to the reactor/mashing tank 100.

Initially the spectra shows characteristic features of starch and long chain maltodextrins. But over the course of an hour, the intensity of the 1020-1030 $cm^{-1}$ region increases while a general signal increase over the remaining part of the 1200-900 $cm^{-1}$ region is observed.

The spectroscopic change indicates that the potato starch is hydrolyzed while the sugar compounds in solution is increased due to the higher solubility of short chain starch derived compounds versus long chain starch compounds. Simultaneously with the real-time recording of the spectra, each spectrum is deconvoluted. The intensity of all the bands in the 1160-900 $cm^{-1}$ region is used to calculate to total concentration of starch-derived compound in solution. The band at 1030-1020 $cm^{-1}$ is used to calculate the average degree of depolymerization. As soon as the optimal composition is reached, the content of the reactor is pumped further onto a fermentation unit.

Example 6

On a plant producing second-generation bio-ethanol fuel additives, the feedstock containing pulverized straw and corn stover is initially pretreated at elevated temperatures and pressures with a dilute sulfuric acid solution. During this treatment, the slurry is cooled, and the crystalline cellulose fibers are all converted into amorphous cellulose. The amorphous lignocellulose is extracted, washed and water with buffering agent is added. Then powdered commercial grade cellulase is added and the temperature adjusted and maintained at around 50° C.

The process is monitored by analyzing the liquid part of the slurry that is sent to a customized ATR-FTIR instrument 200, 300 adjacent to the mashing unit 100. The sample is extracted continuously by filtering of the largest particles to prevent plugging. The filtered slurry is transferred to a special designed chamber on the ATR-unit of the FTIR instrument.

For the first period of operation of the mashing, the signal increases significantly in 1200-900 $cm^{-1}$ region indicating the dissolution of cellulose oligomers from the amorphous lignocellulose particles in the slurry. Later, the signal in the region starts to stabilize while a marked decrease in the 1020-1030 $cm^{-1}$ region is observed due to the hydrolysis of the oligomers into glucose. When the change/per minute in the 1020-1030 $cm^{-1}$ region is below a certain threshold limit value, a feedback trigger message is automatically sent from the ATR-FTIR analyzer to a process control system. At this threshold enzyme activity is decreased, and the slurry mostly consists of lignin particles and glucose and a minor part of cellobi- and tri-ose and higher chain length oligomers. The trigger message sent to the process control system activates a pump with filtration unit, and the filtrate is pumped into a fermentation unit.

Example 7

A microscale mash is performed by mixing 225 g of ground, malted barley with 1 L water at 54° C. in a conical flask during magnetic stirring. pH is adjusted by adding 0.25 g citric acid. The temperature is maintained at 54° C. for 15 minutes. Then the temperature is raised to 65° C. for 1 hr, and finally to 75° C. for 25 minutes. During all three temperature steps, aliquots of a few mL is extracted using a pipette during the mashing, and transferred to a test-tube on a boiling water bath for 5 min to ensure denaturation of enzymes. Then the precipitate is removed by centrifugation, and an ATR-IR spectra is obtained of the remaining clear liquid phase, and the refractive index in Brix % is determined using a refractometer. The Brix scale is often used in the food and brewing industry, and is a convenient way to describe refractive indices so they relate directly to the total amount of dissolved carbohydrates in solution.

Figure 16:
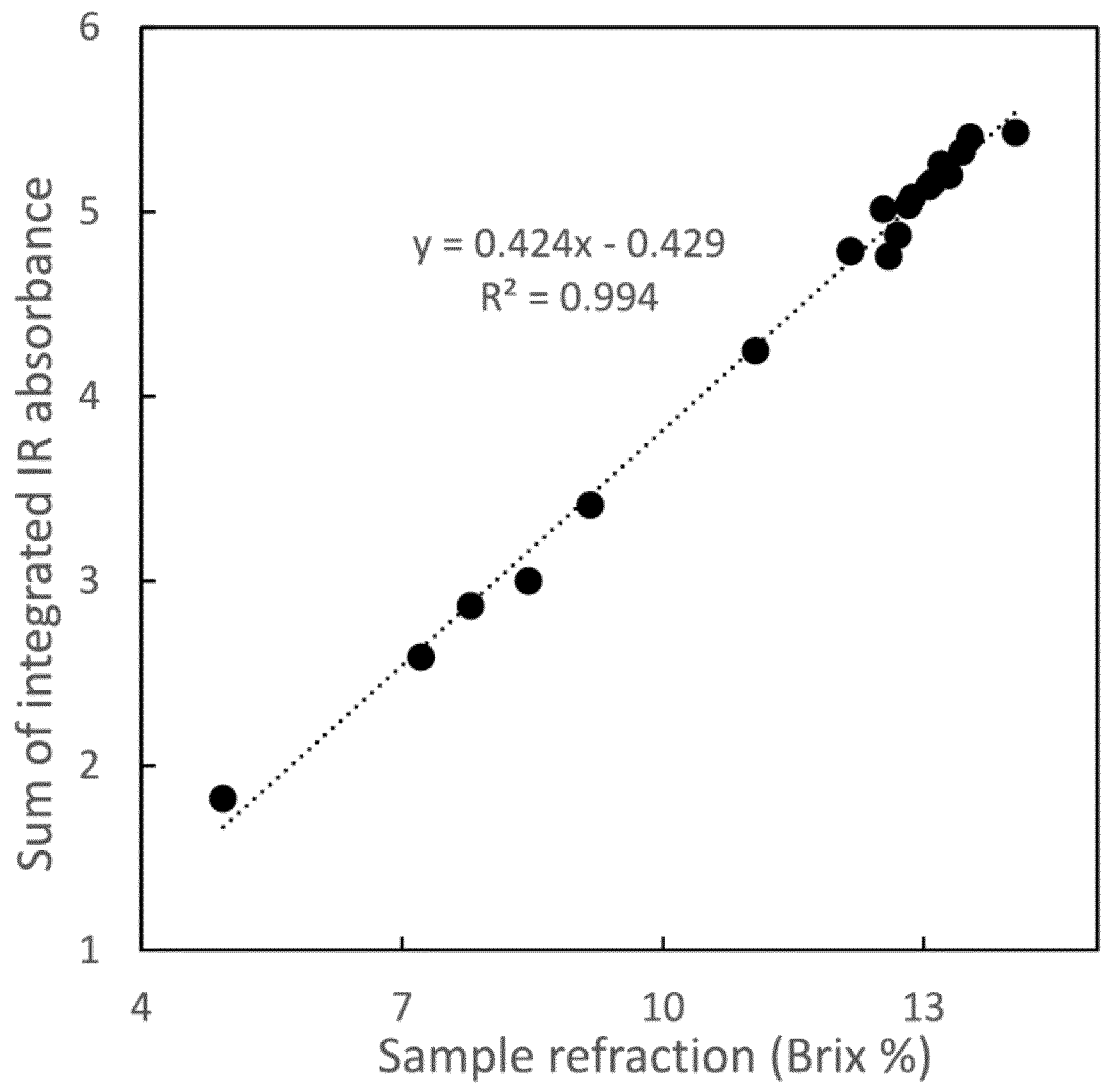
FIG. 16 shows the relationship of integrated IR absorption from 1260-950 $cm^{-1}$ and the Brix % during mashing of malted barley.

All spectra are ATR corrected assuming a refractive index of 1.36 using Thermofisher OMNIC software and a spectrum of pure water was subtracted from each spectrum of the mash. Then the integrated absorbance from 950 $cm^{-1}$ to 1260 cm-1 is determined and plotted as a function of the Brix % value of the same sample. The plot is shown in FIG. 16.

The relationship between the two shows that the summed integrated IR absorption in the difference shows a very accurate relationship with the total amount of dissolved carbohydrates during mashing. Hence, the total amount of dissolved carbohydrates during mashing can be monitored accurately in real time using ATR-IR spectroscopy.

Example 8

In the literature, it has been described that the particulates of the mashing would cause problems in the application of ATR-IR spectroscopy, as the starch granules and husk particles would affect the spectra of the solution phase. This seem to be a common perception among skilled scientist in the field.

Although it is observed to be partly true for very early times of the experiment where some of the ultra-small starch granules indeed seems to contribute slightly to the spectra, this has very little technical influence on this invention. As the solid-state particles are only found to influence the monitoring at very early times of the experiment; i.e. the granules has no effect during the interesting stages of mashing (after the first few minutes).

In the laboratory a mashing according to the procedure in the previous example 7 is performed. Around 20 minutes into the mashing a sample of approximately 2 mL is transferred to a test tube in an ice bath to quench the enzymatic hydrolysis reaction.

The sample is at this point very slurry and appear milky and opaque due to the fine starch granules and fine husk particles. Then some of the yellowish slurry is transferred with a pipette to a FTIR-spectrometer with a diamond ATR device, and an IR spectrum is recorded while the sample is constantly kept in motion using a pipette, i.e. stirred with a pipette. Spectra are taken of the static sample without keeping it in motion. Finally the crystal is thoroughly cleaned with a moist tissue and some more of the same sample is transferred to the ATR crystal.

Figure 17:
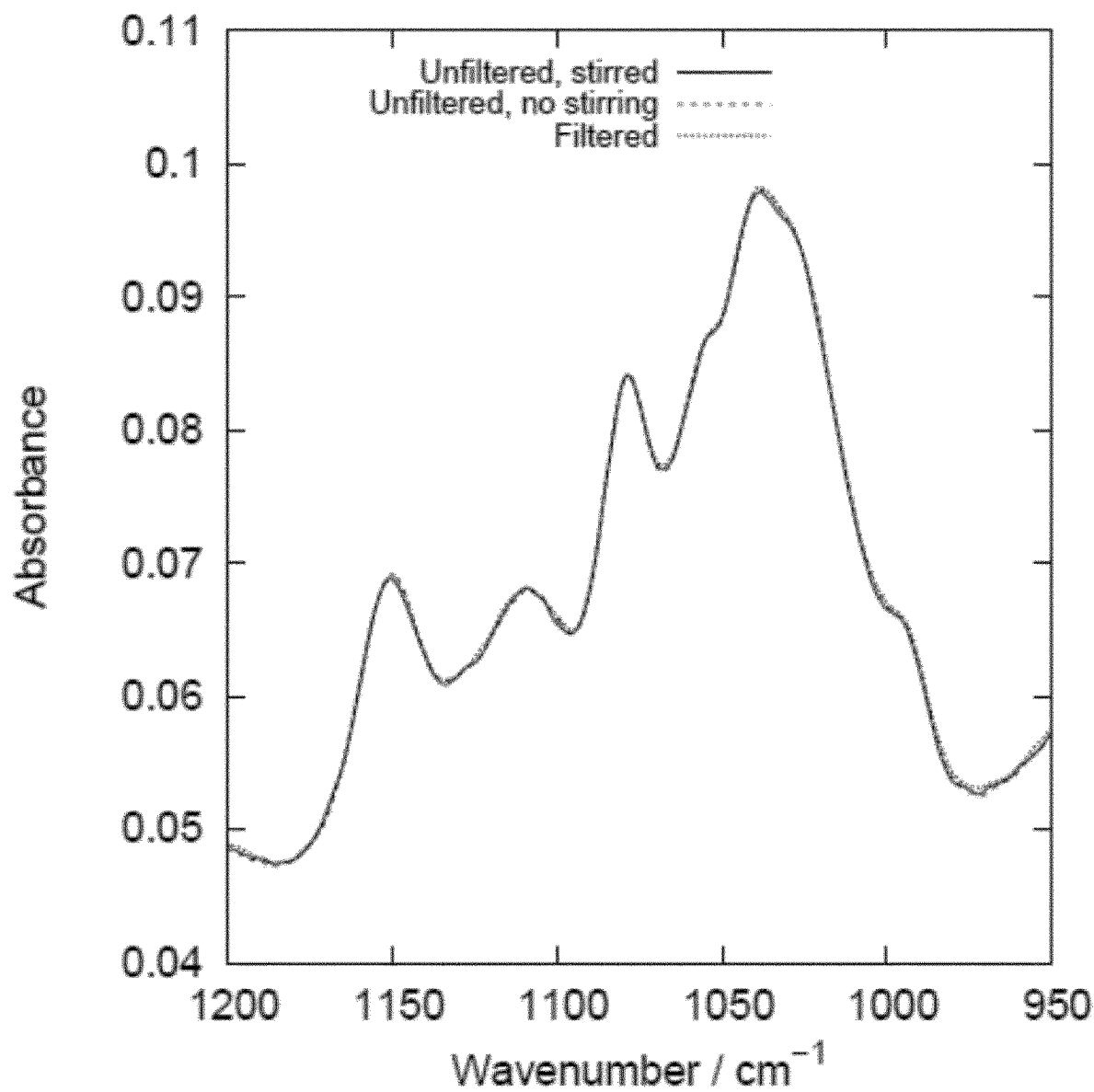
FIG. 17 shows the IR spectra of the same sample aliquot during mashing, with and without filtration.

The last time the sample is transferred to the ATR crystal using a syringe equipped with a 0.22 μm syringe filter. The spectrum of this clear liquid is identical to the previous spectrum of the slurry sample, demonstrating that the particulates in the mash does not influence the recorded spectra. The three spectra are compared at FIG. 17 showing the same sample aliquot during mashing, with and without filtration. In the case of the unfiltered sample, the effect of stirring the sample while recording is investigated.

Figure 18:
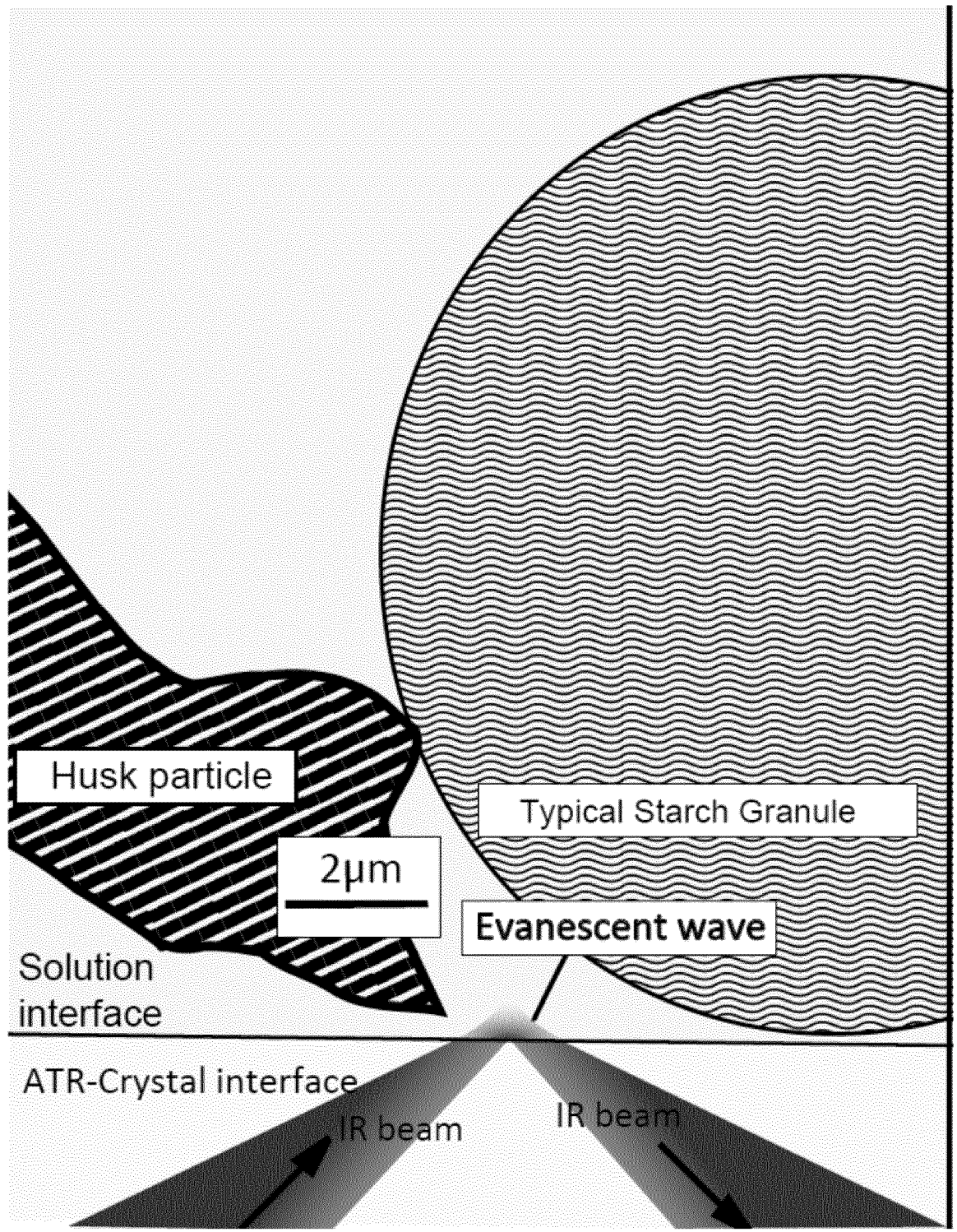
FIG. 18 shows the mechanism behind this phenomenon observed in FIG. 17.

The illustration in FIG. 18 shows the mechanism behind the phenomenon observed in FIG. 17. As long as the particles in the slurry are significantly larger than the penetration, depth of the evanescent wave, their contribution is negligible to the recorded spectrum. I.e. the recorded spectrum is in practice independent of the particulates and only the solvated part of the slurry is ever recorded. The focused evanescent wave will only penetrate a very thin film of the liquid. The penetration depth of the evanescent wave is magnitudes smaller than the typical starch granules and husk particles in the slurry, in practice excluding the granules from the spectra, and obtains a spectrum of the pure liquid.

Example 9

A chemometric model based on IR spectra in the fingerprint region model must rely on all possible details to discriminate between very similar compounds with reasonable accuracy, especially with the respect to the present invention where small changes in structure of bio-molecules have to be quantified using ATR-FTIR. First of all it is naturally worth to consider the spectroscopic changes due to primary structure changes. In an enzymatic hydrolysis of a biopolymer, this would be the changes directly related to the breakage of polymeric bonds. Here the direct spectroscopic change would be related to the disappearance of the primary group frequency bands of either peptidic bond in proteins or glycosidic bonds in carbohydrate respectively.

However new spectral features due to secondary structure may be crucial to consider. The secondary structure changes should here be understood as changes that occurs or becomes possible as indirect consequence of the primary structure change e.g. breakage of a glycosidic or peptide bond during the mashing.

This example shows how the present invention rely on a more sophisticated method, than is normally used in spectroscopy based chemometrics that often rely solely on blind statistical analysis. In this method it is important to: 1) identify, 2) understand and then 3) rationally quantify and exploit secondary structure changes suddenly becoming possible or indirectly induced by the primary enzymatic process. The breakage of e.g. a peptide bond would not only result in the loss of the characteristic vibrational modes of the peptide bond but also result in the creation of both an amine group as well as a carboxylic acid.

Figure 19:
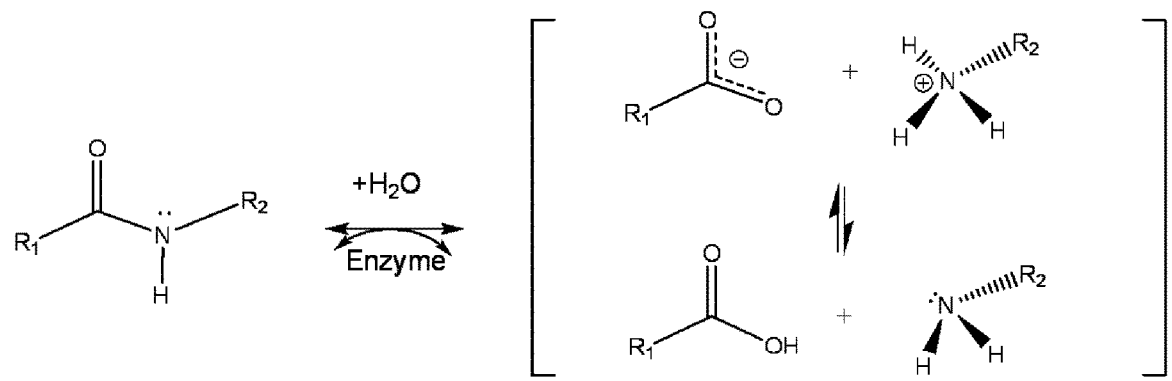
FIG. 19 illustrates the hydrolysis of the peptide bond.

In such cases the most important discriminators are most likely these secondary changes. In this example especially, the appearance of significantly different modes due to the dramatic changes in the symmetry, especially if the product is ionic, is at least as useful as the primary structure change. This is illustrated in FIG. 19 showing hydrolysis of the peptide bond allowing several new species to develop, with very different symmetric and spectroscopic properties. However, unilateral statistical use of the new illustrated spectroscopic signatures would require a very large calibration set. But what would further make this approach very limited in a technical sense, is that it would only be valid in a very narrow pH range. The approach presented hereunder applies a qualitative interpretation along with a quantification and result in a model that is much more rich and versatile in its predictions.

Figure 20:
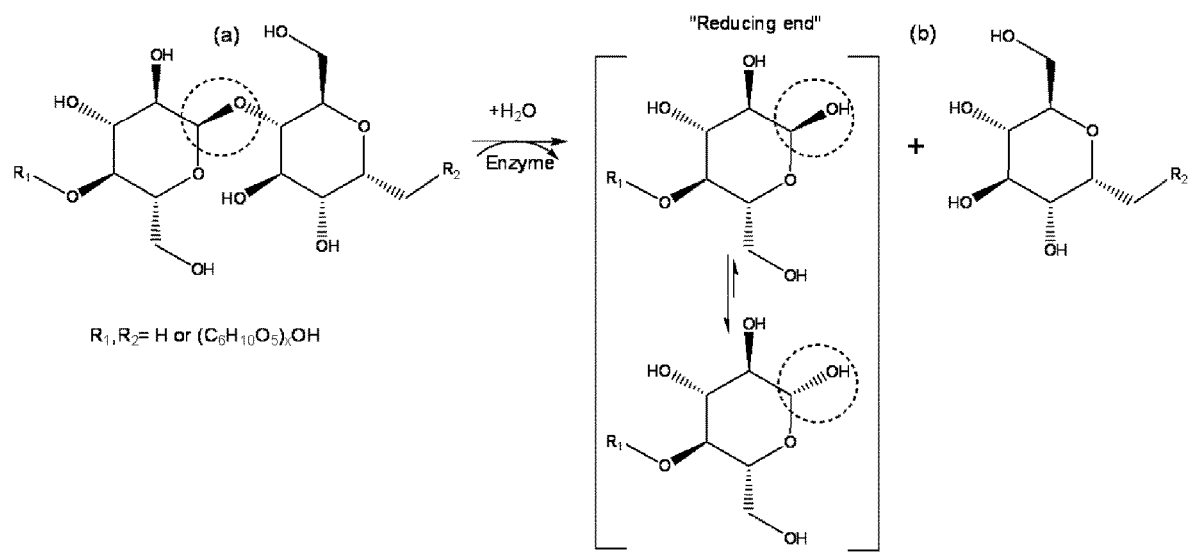
FIG. 20 shows the hydrolysis of amylo-starch.

As shown in FIG. 20, the hydrolysis of amylo-starch facilitates a secondary structure change, as the reducing end will not remain in the α-pyranose form but engage in an equilibrium with the beta form. In aqueous solution, D-glucose exists as an equilibrium between the α- and β- of glucopyranose forms, in a ratio approximately 34%:66% respectively. This equilibrium is very dynamic and the two forms are interchangeable through mutarotation.

In the original amylose fragment form all anomeric C—O groups are in the α-configuration (see the dotted circle at (a)). During the hydrolysis a "reducing end" is made. At the reducing end the carbohydrate can transform into the beta anomer, which is slightly more stable than the α-anomer. The same is true for the reducing end of di-, tri-, oligio- and polysaccharides which can also undergo mutarotation.

Figure 21A:
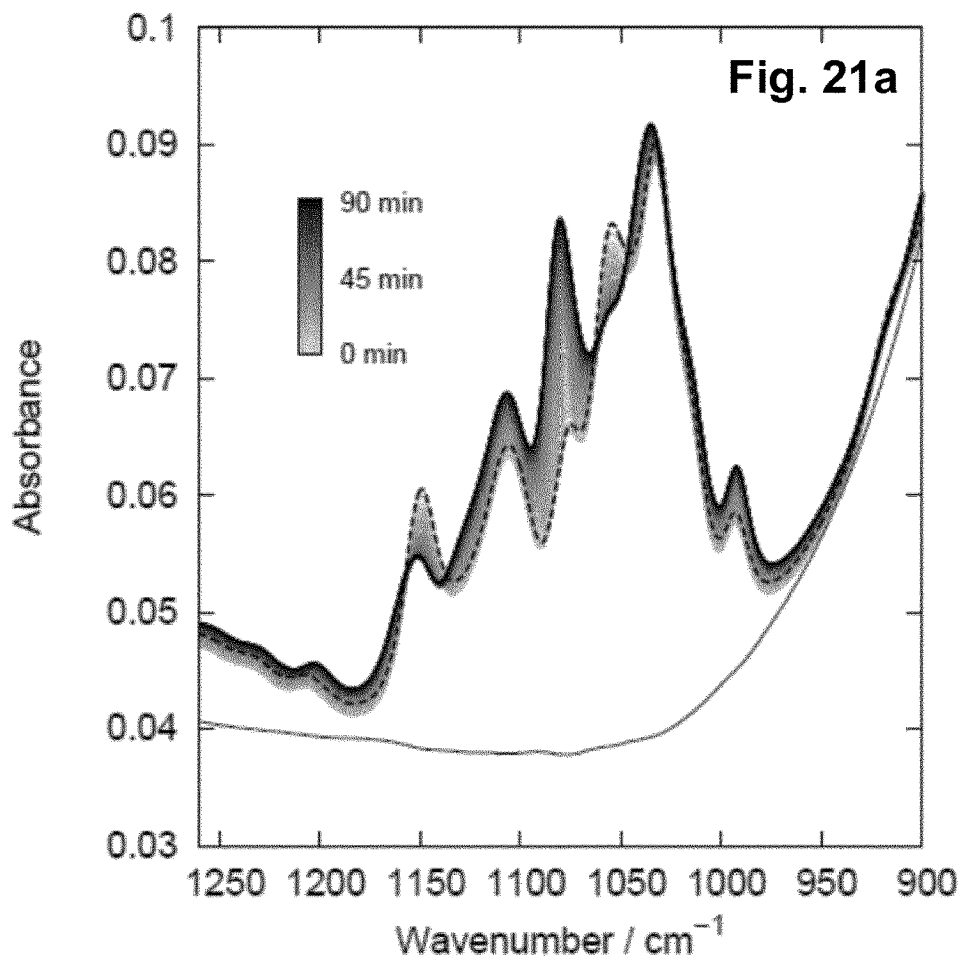
FIG. 21a shows the conversion of the pure anomeric α-glycosyranose form the racemic mixture at Room temperature.
Figure 21B:
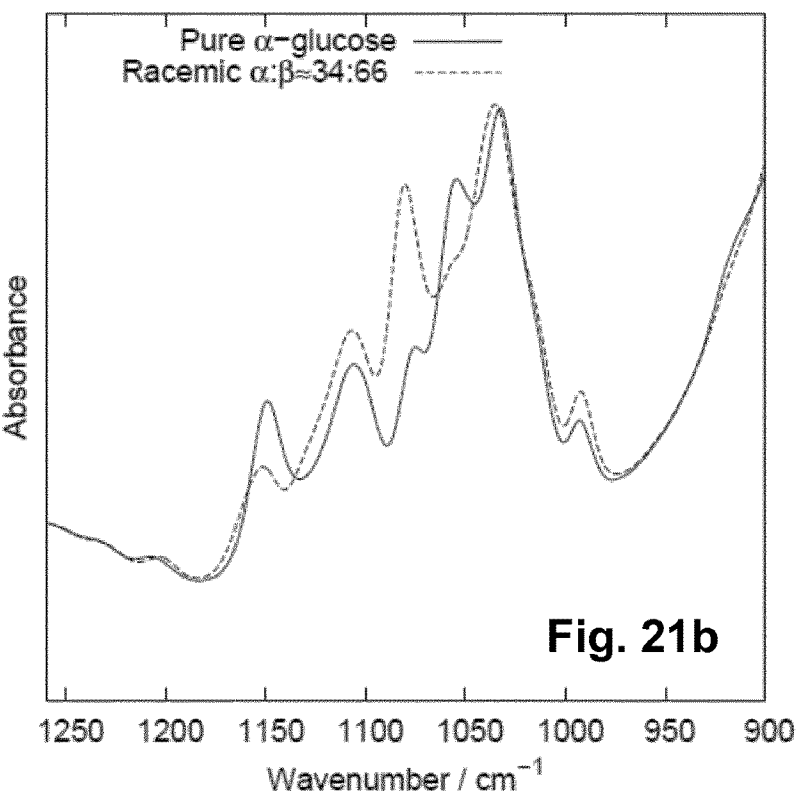
FIG. 21b shows the comparison of the pure dissolved α-D-glucopyranose with racemic mixture of α and β-forms D-glucopyranose at equilibrium.

There is a significant difference between the spectroscopic signature of the α- and β-glycopyranose as is demonstrated in FIG. 21a and FIG. 21b.

FIG. 21a shows the conversion of the pure anomeric α-glycosyranose form the racemic mixture at room temperature. The dotted line shows the pure α-form.

Lighter tones in the spectra corresponds to earlier timestamps in the experiment whereas darker corresponds to later timestamps.

FIG. 21b shows the comparison of the pure dissolved α-D-glucopyranose with racemic mixture of α and β-forms D-glucopyranose at equilibrium.

The spectra are obtained by rapidly dissolving 12.5 w/v pure crystalline α-D-glycopyranose (Sigma-Aldrich) in water and continuously recording spectra of the solution using a germanium ATR cell at room temperature for 90 minutes (first spectra recorded in less than 1 minute from the start of mixing). Then the sample is covered to avoid evaporation. During the experiment, the change of the pure α-D-glycopyranose form of glucose to the mixture of both α and β forms can be observed in situ. After 90 minutes no changes in spectral features is observed, hence the α and β forms has reached equilibrium.

The spectra is identical to samples stored for more than 24 hr. Two significant spectroscopic handles are that the intensity of the 1080 $cm^{-1}$ band is much strong in the β form, whereas the 1055 $cm^{-1}$ and 1150 $cm^{-1}$ bands are much more intense in the α-form. As the IR active modes in the fingerprint area in the most cases has a very complex and mixed origin each comprising several OH and CH bending mode combined with various C—O stretching mode the re-orientation of a single C—O group can get several spectroscopic modes to change.

This is, on top of the measurement of the group vibrations of the glycoside bond itself, also a good measure of the hydrolysis, as it allows the concentration of "reducing ends" to be quantified.

However, real-time use of the spectral features of the beta form as a measure of hydrolysis, would require that the rate of the mutarotation is significantly faster than the rate of starch hydrolysis. If the kinetics in the anomeric equilibrium was slower than the rate of hydrolysis, this would make real time chemometric modelling of the process very challenging.

The kinetics at the equilibrium is, as shown in FIG. 20, relatively slow at room temperature. It is indeed not possible for a person skilled in the art in general to make a final judgement on how the kinetics of the equilibrium vs. the hydrolysis is at elevated and more realistic process temperatures.

Therefore, the in situ mutarotation is performed at 60° C. which is more typical for most enzymatic hydrolysis processes, e.g. mashing of malted cereals, as this temperature is close to the gelation temperature of starch. The heating is introduced by a homemade electrical heating device placed on top of the Germanium ATR device that can maintain isothermal conditions. The temperature is further monitored, by a thermocouple very dose to the germanium crystal. Then α-D-glucopyranose is mixed with water at room temperature and then quickly transferred to the 60° C. hot germanium crystal covered by the heating block while IR spectra are recorded continuously. The IR spectra are shown in FIG. 22 showing in situ conversion of α-Glycopyranose, i.e. the racemic mixture of the α and β forms at 60° C. The dotted line is the spectrum of the pure α form at t=0. Lighter tones in the spectra correspond to earlier timestamps in the experiment whereas darker corresponds to later timestamps.

The experiment clearly demonstrates that the kinetics are very fast at typical mashing conditions, and bands associated with the increased amount of β-glycopyranose form in shorter oligosaccharide chains is a good alternative measure of the overall hydrolysis of starch.

The experiment is performed both with and without 0.25 w/v % citric acid added to the water prior to dissolution of the α-glycopyranose, and the mutarotation rate is observed to be independent of the presence of the small amount of citric acid. The example clearly demonstrated the importance of this unexpected and indirect spectroscopic handle during hydrolysis. Analogous this would apply for related systems. An example is in the case of cellulose (β-(poly-(1, 4)-glycopyranose) hydrolysis, where the hydrolysis form would result in a higher amount of the α-glycopyranose due the mechanism described above.

Example 10

Various types of maltodextrins are available commercially, all characterized by their reducing power in dextrose equivalent (DE). The DE number is measured by the sugars capability of reducing Cu(II) to Cu(I), and has been the industry-standard way to measure DE values for carbohydrates. Where pure glucose is defined as DE=100 while maltose and maltotriose e.g. has DE values of 50 and 33 respectively, a maltodextrin of an average degree of polymerization (ADP) 8 would have a DE number of:

$$DE = 1/8 = 12.5 \quad [2]$$

For starch-derived oligosaccharides, the average degree of polymerization is the reciprocal DE value.

$$DE = 1/(ADP) \quad [3]$$

The reduction is performed in large surplus of Cu(II). As Cu(II) is much more colored than the pale slightly bluish-green Cu(I), the traditional method of determining the Cu(II) concentration after reduction has been the Lane-Eynon titration, or by gravimetric methods, which are both rather laborious methods. Further, these methods are inherently impossible to do in real time.

In here is adapted a newer and well established method, which allows the Cu(I) concentration to be determined colorimetric as a strong purple complex when 2,2-bquino-line-carboxylate anions are added. Further the moisture content of all maltodextrins are determined graviometrically by heating all sugars at 105° C. for 1 to 2 hours, and the DE and ADP values are calculated with respect to the dry fraction of the maltodextrins.

The use of this well-established orthogonal technique is found to be a good way to validate accuracy the method applied by the current invention. Reagents are prepared according to (Zhang, Y.-H. P.; Lynd, L. R. Biomacromolecules 2005, 6, 1510-1515.). The reaction time at 75° C. is increased from 30 minutes to exactly 60 minutes. 5 different dilutions is used for each carbohydrate and the concentration of the 2,2-bquinoline-carboxylate-Cu(I) complex is measured via the absorbance at 560 nm. The DE value is determined from slope by linear regression, all with $R^2$ values greater than 0.999, by comparison with a glucose standard. The DE values are given in Table 1.

TABLE 1

ADP values for commercial starch hydrolysis products, obtained by using coloriometric determination of the sugars reducing power of Cu(II) with respect to a glucose standard.

| | Carbohydrate | | | |
|---|---|---|---|---|
| | Maltose monohydrate (sigma-aldrich) | Maltotriose hydrate (sigma-aldric) | "Maltodextrin DE = 16.5-19.5" (sigma-aldrich) | Glucidex12 |
| ADP (from Cu(II) reduction) | 2.01 | 3.02 | 5.54 | 10.5 |
| Corresponding RDP | 0.502 | 0.669 | 0.819 | 0.905 |

As ATR-IR spectroscopy is a way to do transmission IR spectroscopy, and as the penetration depth at a certain wave length will always be constant for samples with similar refractive indices, Lambert Beers law as presented in equation 1 is directly applicable.

To further make the analysis of ADP values generic for all concentrations substrate concentrations during mashing a term denoted the Relative Degree of Polymerisation (RDP) is introduced. In the general case of a synthetic or biopolymer the RDP would be:

$$RDP = n_{polymeric\_bonds} / n_{total\_monomeric\_units} \quad [4]$$

In the special cases hydrolysis products from either starch or cellulose RDP is defined:

$$RDP = n_{glucosidebonds} / n_{total\_glucose\_units} = (n_{total\_glucose\_units} - 1) / n_{total\_glucose\_units} \quad [5]$$

E.g. the monomer will have a RDP value equals zero, the dimer will have a value of 0.5, while the heptamer of 6/7 and so forth. With this introduced concept of the RDP, it became possible to create universal calibrations to determine the average degree of polymerization regardless of the absolute carbohydrate concentration.

Solutions of 15 wt. % carbohydrates are prepared, of each of the carbohydrates presented in Table 1. Spectra of all samples shown in FIG. 23 were recorded using a 45° Diamond ATR device. The model used to deconvolute the spectra are indicated in the spectra.

All spectra in FIG. 23 are analysed the following way: The spectra are ATR corrected to approximate the corresponding true transmission spectra, then a background of water is subtracted from each spectra. Finally each of the ATR-corrected difference spectra are deconvoluted using a model comprising pseudo-voigt functions. During deconvolution, position and bandwidth of the distribution curves are constrained and only the amplitude is optimized, to ensure that the bands do not migrate randomly during deconvolution. To accommodate some flexibility due to slight shifting of the bands, in some cases some bands are split into two bands with positions very close to each other. E.g. the bands at around 1080 and 1152 cm$^{-1}$ is respectively represented by the sum of bands at 1078+1081 cm$^{-1}$ and 1148+1154 cm$^{-1}$. Each of the obtained band areas are normalized by dividing by the sum of all bands from the deconvolution. Dividing by the total area is equivalent to normalizing with the total dissolved carbohydrate concentration. This is clearly a very good approximation as demonstrated in example 8 clearly showing that the total dissolved carbohydrate concentration is proportional with the integrated area of all of these bands.

Figure 24:
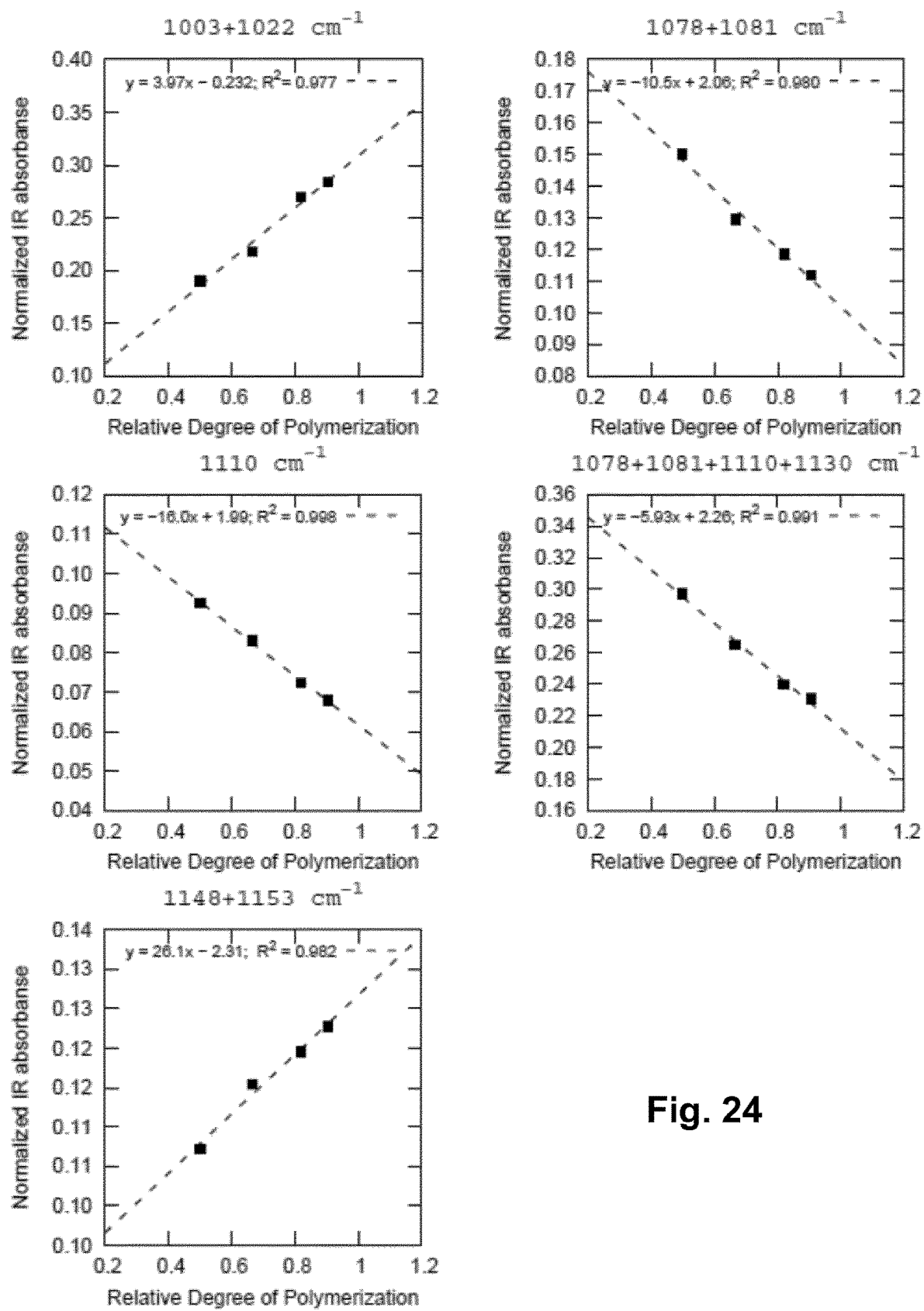
FIG. 24 shows the plot of several of the deconvoluted band areas of FIG. 23 against the RDP values obtained from the DE values from the Vis spectroscopic Cu(II)-Cu(I)-2,2-bquinoline-carboxylate.

By plotting several of the deconvoluted band areas against the RDP values obtained from the DE values from the Vis spectroscopic Cu(II)-Cu(I)-2,2-bquinoline-carboxylate, as shown in FIG. 24, it is shown that by applying the new method, the same values can be obtained from IR in real-time, without having to ad reagents. This is a huge advantages both in terms of simplicity of the method and the ease with which it can be conducted but also in terms of costs.

FIG. 24 shows the integrated band areas from the deconvolutions of the four spectra shown in FIG. 23, showing very good statistical correlations with the RDP values of the carbohydrates.

Example 8 shows that the IR spectra can be used to establish good values for the total amount of dissolved carbohydrate during mashing. On top of this the present example 10 shows that the present invention can be used to accurately determine the average degree of polymerization of the total dissolved sugars, which is a value that cannot be rapidly obtained by any other means.

Example 11

As discussed above in example 10, maltodextrins are often characterized through their DE values. However, the DE number alone does not describe maltodextrin completely, as the ratio of α-(1-4) and α-(1-6) glycoside bonds can vary independently of the DE number. The maltodextrin used in e.g. calibrations studies must have a realistic distribution of both α-(1-4) and α-(1-8) glycoside bond. Starch is primarily composed of glycose linked with α-(1-4) glycoside bonds, which makes the majority of the glucoside bonds the α-(1-4) type. However especially the amylopectin part of starch is branched due to a smaller amount of α-(1-6) glycoside bonds. Due to this branching roughly around 5% of the glycoside bond in typical starch is α-(1-6) while the rest is α-(1-4). As the most of the amylases can only hydrolyse the α-(1-4) glycoside, the majority of the native α-(1-6)-glycoside bonds in the starch stays intact during the hydrolysis process, as they are much more resistant to most amylase attacks. Therefore the amount of α-(1-6) glycoside bond residue in the final hydrolysis of most starches, contributes significantly to the glycoside bonds of the unhydrolyzed oligosaccharides, and cannot be ignored from a spectroscopic point of view.

Thus a solution of iso-maltotriose (α-D-glycopyranose-(1,6)-α-D-glycopyranose-(1,6)-D-glucose, Sigma-Aldrich) is used as a reference for the pure spectral features of the α-1,6-glycoside linkage. Further, the commercial and food approved α-(1,6)-glucose-oligosaccharide VitaFiber is purchased from different distributors. Although Vitafiber is mainly composed of α-(1,6)-glucose-oligosaccharide with a smaller fraction of mixed α-(1,6)/α-(1,4) glucose-oligosaccharides. These two α-(1,6) glycosidic compounds is then compared to a commercial maltodextrin (ADP=5,54, sigma) and pure maltotriose.

FIG. 25 shows spectra of 12.5 w/v % solution of iso-maltotriose, VitaFiber oligosaccharide, SigmaAldrich maltodextrin, Maltotriose and water. The difference in the absorption at around 1000-1030 $cm^{-1}$ shows a surprising difference between the spectroscopic features of the α-(1,4) and α-(1,6) glycoside bonds.

It is quite apparent that the isolated α-(1,6) bonds are quite different, and α-(1,4)-maltotriose and iso-maltotriose showed significant differences. Especially at around 1025 $cm^{-1}$ the absorption of the acetal vibration modes are significantly stronger in the α-(1,6) isomers. Further, the 1155 $cm^{-1}$ mode of the antisymmetric glycoside C—O—C stretching mode is shifted slightly up to around 1160 $cm^{-1}$.

The Vitafiber and the short commercial maltodextrin are both found in between the two pure samples (iso-maltotriose and maltotriose), showing that they both contained a significant amount of both types of glycosidic bonds. Especially since the maltodextrin is manufactured through partial hydrolysis of natural starch, it is a very realistic model for the maltodextrin development during real mashing processes. Therefore it is concluded the low ADP maltodextrin purchased from Sigma-Aldrich would serve as a realistic model with a realistic ratio of α-(1,6)/α-(1,4) glycosidic bonds. Further this example shows that the present invention, under the right circumstances, is able to discriminate and quantify different types of glycosides in mixtures. Especially taking the example 9 into account, the above results, in combination with a deconvolution and/or statistical analysis, can be used to build a multivariate model that can discriminate and quantify the types of glycoside bond in addition to the ADP value in real time during a mashing process.

Example 12

During the last 50 years the exact location of the glycosidic vibration in polymeric carbohydrates have been discussed greatly. Several controversies have been presented throughout the years based on arguments and indices, without any solid proof from experiments alone, on where to locate the characteristic frequencies of the glycoside bond. Therefore, it seems apparently impossible make an in-depth analysis of the fingerprint region of IR spectra of carbohydrates, even for a person simultaneously skilled in the art of spectroscopy and chemistry. This is especially true for features that are related to the degree of polymerization.

Previous examples in the literature has failed to use statistical analysis such as partial least square (PLS)analysis, to discriminate similar di- and trisaccharides like maltose and maltotriose based on experimental IR Data. When otherwise well-proven statistical techniques for previous studies, to discriminate very simple mixtures of carbohydrates, has failed, it has led to the assumption that it is not possible to use IR to discriminate the sugar types and their degree of polymerization.

From the electronic structure, the quantum mechanical normal modes of the molecule can be calculated, as well as a good estimate of the oscillating dipole as a function of the normal mode. This means that a very realistic infrared spectrum can be generated from the electronic structure. This allows for much more qualified interpretation of the experimental spectra, as each band in the experimental spectra can be assigned with a quantum mechanically well described normal mode.

The normal modes of amylose are studied quantum mechanically using density functional theory on glucose, maltose and maltotetraose. First the energy of the electronic structure of each carbohydrate was minimized by using the B3LYP functional and the 6-31G(d) basis set using a commercially available software package. Then the IR spectra is calculated, and the calculated spectra is corrected for anharmony with a scaling factor of 0.98 in accordance with common practice in literature.

The theoretical spectrum is in good agreement with the experimental bands, and reveals that the glycosidic linkage is involved in several characteristic vibrational modes. The medium intense band at 1155 $cm^{-1}$ is assigned to the antisymmetric C—O—C vibration of the glycoside band. Although glucose and the non-reducing ends also have absorptions in the same region, due to the C4-O stretching, these vibrations occur at slightly lower wavenumbers and at significant lover intensities. Strong bands at around 1035-1000 $cm^{-1}$ can be related to modes comprising strong vibrations of the O—C—O stretching modes around the acetal groups of the glycopyranose rings. The α-(1,4) glycoside bonds gave rise to a medium strong absorption while the similar mode in the case of α-(1,6) glycoside bonds has even stronger absorption, which again explains of the difference of the presented spectra for maltotriose and iso-maltotriose shown in FIG. 25.

Example 13

Three stem solutions were prepared: 15% w/v glucose (anhydrous, water content <1%), maltose (15% w/v with respect to mass of maltose monohydrate, Sigma Aldrich) and maltodextrin (ADP=5.54, purchased from Sigma-Aldrich). Then mixtures of these, according to table 2 are produced, by mixing with a high precision auto pipette. An FTIR spectrum of each of the 21 calibration standards is recorded using a horizontal 10 reflection germanium 45° ATR cell and a Nicolet iS5 spectrometer. All spectra are ATR corrected using a refractive index of 1.36, for all samples. A deconvolution analysis of all 21 samples is performed analogous to the method described in example 10, but with slightly adjusted parameters. Further the water background used to generate the difference spectra is an analytical approximation by a higher degree polynomial. Further an algorithm is applied that corrected the spectra from drift, by analysing several absorptions at higher and lower wave lengths where the overall absorption from the carbohydrate features is lower.

TABLE 2

| entry | Glucose | maltose | maltodextrin | RDP |
|---|---|---|---|---|
| 21 | 30% | 70% | 0% | 0.350 |
| 20 | 25% | 70% | 5% | 0.391 |
| 19 | 20% | 70% | 10% | 0.432 |
| 18 | 15% | 70% | 15% | 0.473 |
| 17 | 10% | 70% | 20% | 0.514 |

TABLE 2-continued

| entry | Glucose | maltose | maltodextrin | RDP |
|---|---|---|---|---|
| 16 | 5% | 70% | 25% | 0.555 |
| 15 | 0% | 70% | 30% | 0.596 |
| 14 | 0% | 65% | 35% | 0.613 |
| 13 | 0% | 70% | 30% | 0.596 |
| 12 | 0% | 75% | 25% | 0.580 |
| 11 | 0% | 90% | 10% | 0.532 |
| 10 | 0% | 95% | 5% | 0.516 |
| 9 | 0% | 98% | 2% | 0.506 |
| 8 | 0% | 100% | 0% | 0.500 |
| 7 | 15% | 50% | 35% | 0.538 |
| 6 | 15% | 55% | 30% | 0.521 |
| 5 | 15% | 60% | 25% | 0.505 |
| 4 | 15% | 75% | 10% | 0.457 |
| 3 | 15% | 80% | 5% | 0.441 |
| 2 | 15% | 83% | 2% | 0.431 |
| 1 | 15% | 85% | 0% | 0.425 |

In example 10, it is shown that IR can determine ADP values of pure di- and oligio saccharides. However in most technical cases of mashing the differences in ADP values are far smaller.

Figure 27:
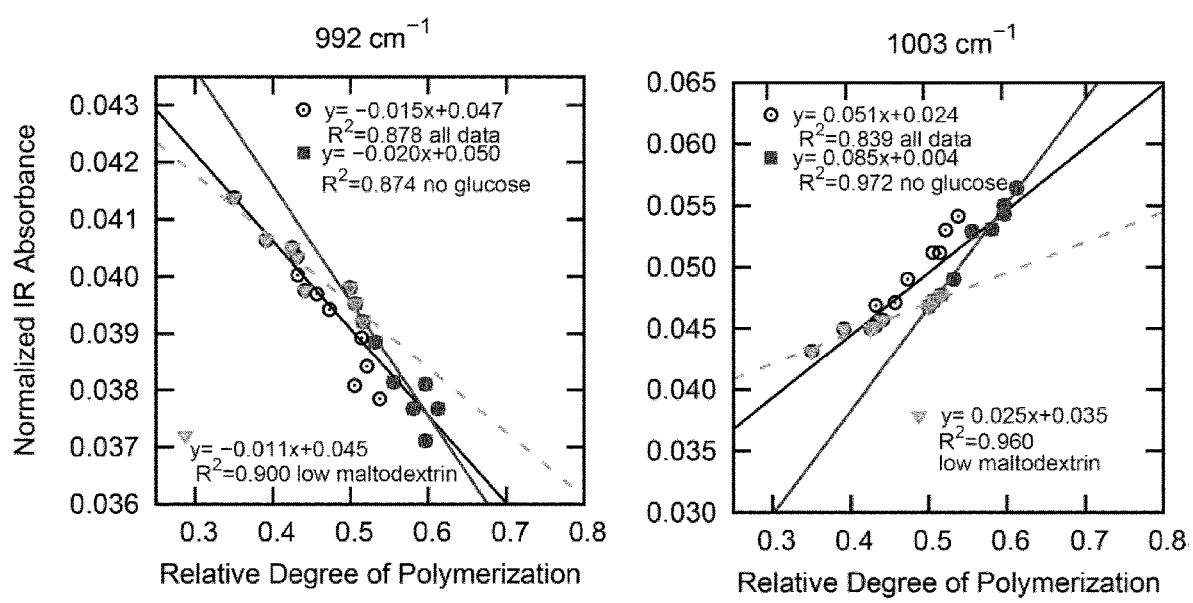
FIGS. 27-28 show correlations between deconvoluted band areas of spectra in FIG. 26 and the relative degree of polymerization at different wavelengths.
Figure 28:
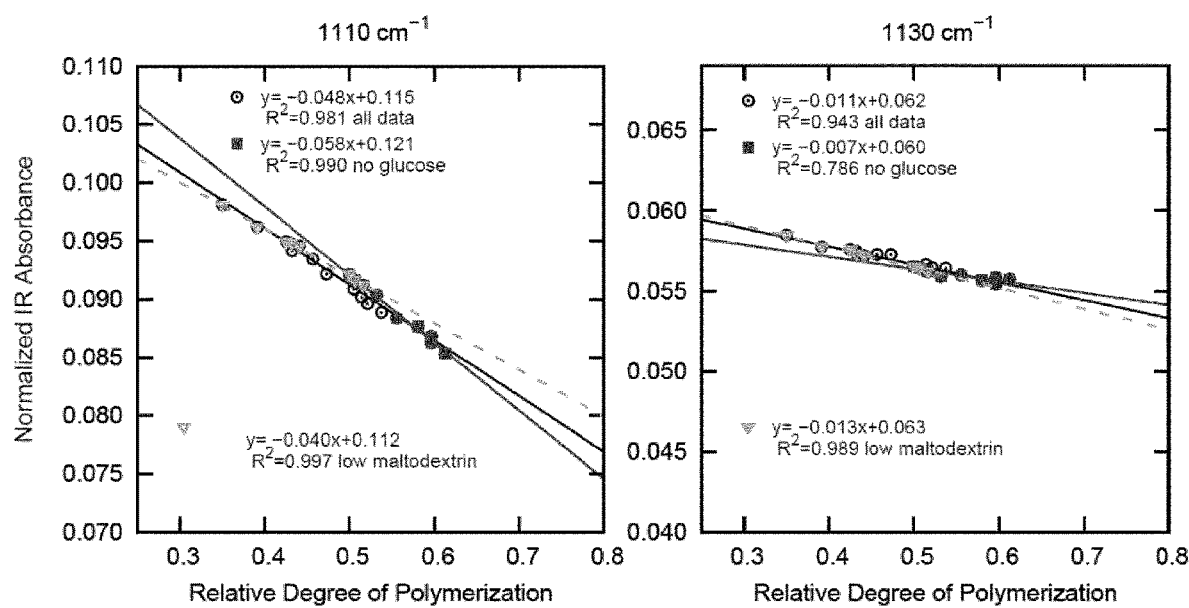
Figure 28:
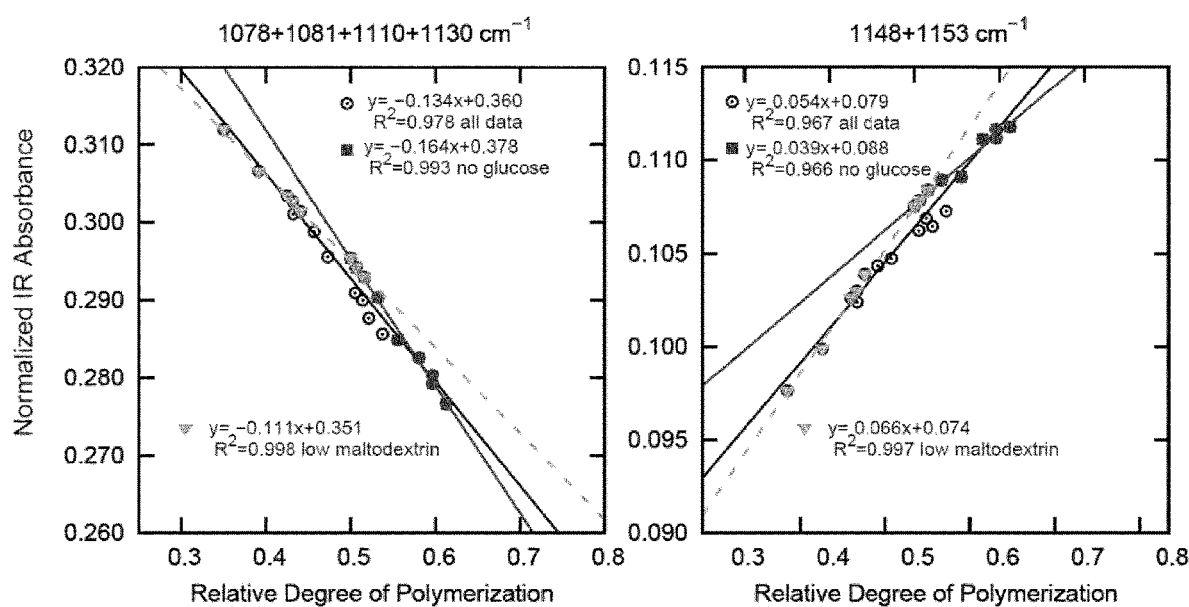

In FIGS. 27 and 28, ten band or combinations of band areas are presented as a function of RDP of the mixtures.

Figure 26:
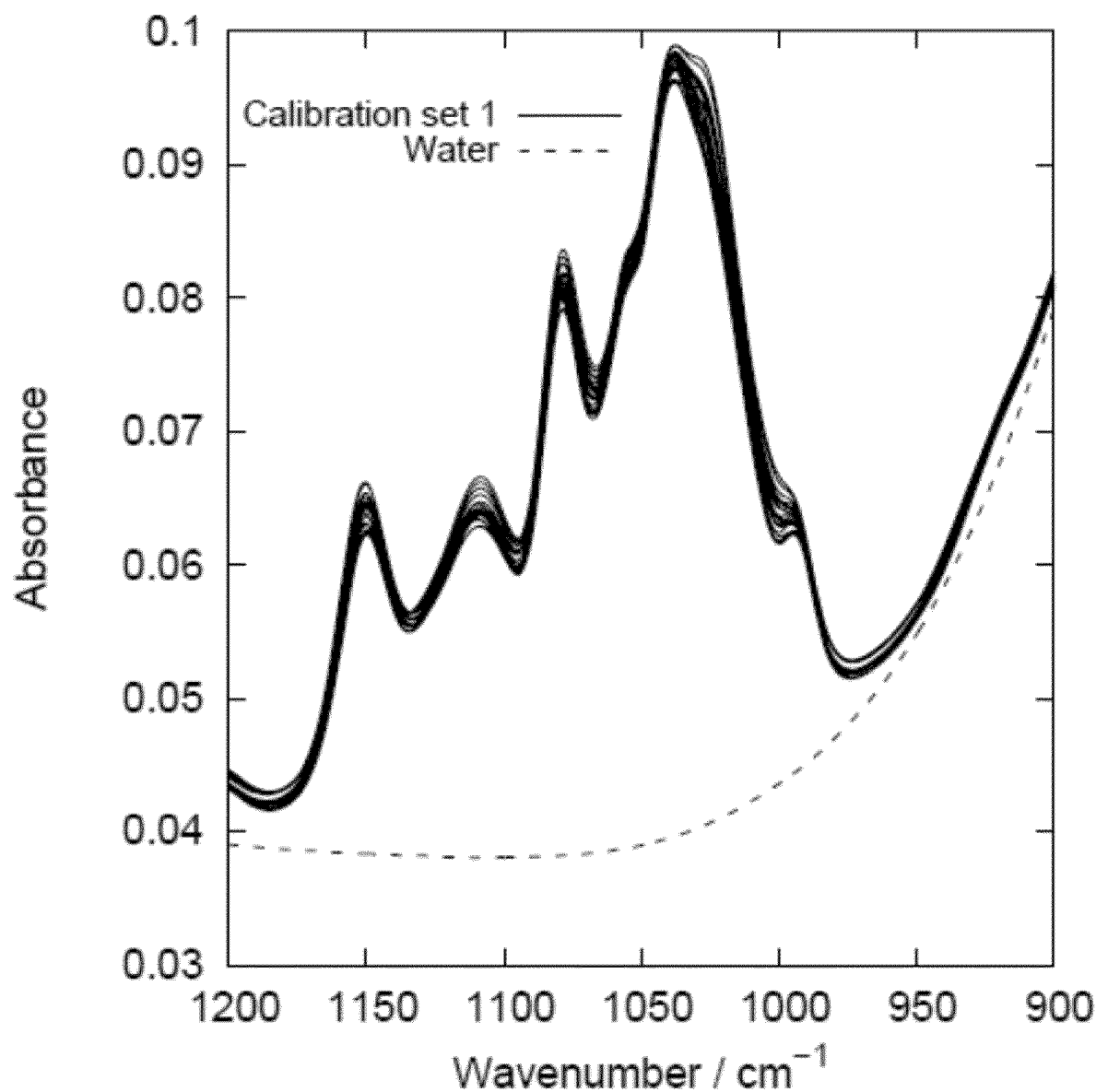
FIG. 26 shows the IR spectra of a calibration set.

FIGS. 27-28 show correlations between deconvoluted band areas of spectra in FIG. 26 and the relative degree of polymerization at different wavelengths. The different regression plots compare the whole dataset where samples containing either glucose or maltodextrin respectively are removed.

The plots presented are chosen as they all show a fair to good correlation with the RDP value, whereas the plots only showing very poor statistical correlation are not shown. Especially for the plots showing the correlation between the RDP and the 1078+1081 cm$^{-1}$, 1110 cm$^{-1}$ and 1078+1081+1110+1130 cm$^{-1}$ summed band areas respectively all show very good correlation; all with R$^2$ values close to or above 0.98. These bands were shown, in example 9, to correlate with the C—O stretching+OH/CH bending specific to either the α or β D-glycopyrano-backbone. These bands seem to be the overall preferred of a universal descriptor in this case to determine the RDP during mashing at a certain time, regardless of the specific carbohydrate composition. The band at 1036 cm$^{-1}$ does in this example also exhibit very good correlation with RDP, but it will be shown later that this is only true in specific cases. Later it will be shown how the 1036 cm$^{-1}$ band can be exploited to supply additional compound specific information on the sample composition.

Different parts of the dataset were used for statistical analysis to make a comparison with specific compound correlations with the RPD values. The correlation between RDP and the above-mentioned bands (1078+1081 cm$^{-1}$, 1110 cm$^{-1}$, 1078+1081+1110+1130 cm$^{-1}$ and 1036 cm$^{-1}$) showed no significant changes upon variation of samples that were included in the dataset. This further shows that they, in the case of mixtures of glucose, maltose and maltodextrin, are good universal descriptors for the RDP regardless of the specific sample composition.

However, it largely increases the usefulness of the present invention that the above universal trend does not apply to all integrated bands and RDP correlations. For the cases of correlation of RDP and band areas for the 1003 cm$^{-1}$, 1022 cm$^{-1}$ bands as well as the sum of the two, the overall correlation at first seemed poor and noisy compared to the above described bands (1078+1081 cm-1, 1110 cm-1, 1078+1081+1110+1130 cm-1 and 1036 cm-1).

However, when only parts of the dataset were taken into account the picture was very different. Especially in the cases where all samples containing glucose was removed before the regression, the correlation became significantly better (R$^2$ increased from 0.85 to around 0.975) and the equation describing the correlation changed with a markedly different slope. Similar, the correlation improved when removing all samples containing maltodextrin. This clearly shows that the apparent scattering of data for these bands, are not noise. These bands are, on top of correlating somewhat to the overall RDP, very dependent on the specific carbohydrate composition of the sample. From this represented analysis it is obvious that these bands play a special role in multivariate calibration during mashing of starch containing feedstock, where it seems especially powerful in the estimation of the glucose concentration, on top of the bare average degree of polymerization.

An example of exploiting the compound specific information embedded in the 1003 cm$^{-1}$ and 1022 cm$^{-1}$ bands in a multivariate calibration, could be to compare the divergence of the RDP values obtained with 1003-1022 cm$^{-1}$ bands and the above used 1078-1130 cm$^{-1}$ bands: The 1078-1130 cm$^{-1}$ bands seems to be much more universal in their predictability of the RDP values in starch mashing.

While both glucose and maltose is fermentable sugars, glucose is present in the final mash in large concentrations (10-30% of total carbohydrates), and is typically the 2$^{nd}$ most abundant carbohydrate in the mash, after maltose. A low glucose to maltose ratio will result in relatively high RDP value, without the presence of a lot of maltodextrin and vice versa. The above-demonstrated principles for multivariate modelling that would make it possible to estimate the glucose concentration in the mixture, is therefore of great technical importance in mashing processes, especially in the brewing industry. An accurate value of the RDP as well as a good estimate of the glucose concentration will facilitate real-time calculation of real degree of fermentability during mashing, which is of great technical value for the brewer.

At last, all samples are diluted down to 11% w/v and 7% w/v respectively, and all samples are recorded in their diluted states. The data are treated the same way as described above, and it is found that the statistics is close to identical to the above presented correlation, which showed that the RDP calibration method indeed provides concentration independent calibrations.

Example 14

The previous example 13 shows how the invention can give estimates for the RDP value as well as the glucose concentration, which can be used to estimate the degree of fermentability. A related challenge arise from the occurrence maltotriose, which, from a spectroscopic point of view, is similar to maltose. In most mashing processes of starch based feedstock, a significant amount of maltotriose is produces as a by-product (up to 5-20% of total carbohydrate). Especially in the case of mashing processes for the brewing industry, it would be of great technical importance to estimate concentrations of maltotriose. This is especially relevant since it is non-fermentable by most types of yeast, and hence contributes with taste in the final product, and is often in the brewing industry just referred to as a general maltodextrin.

Figure 29:
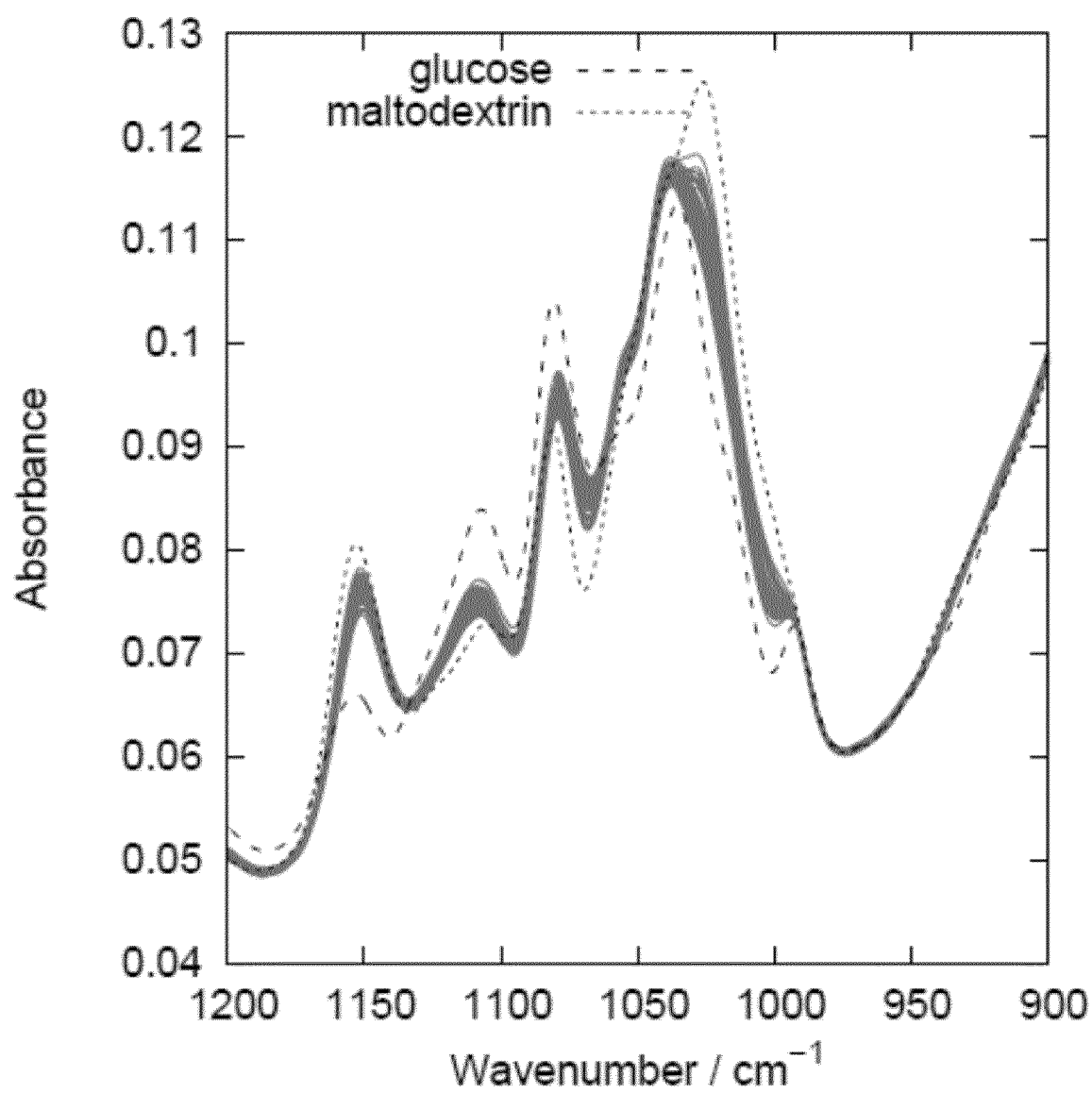
FIG. 29 shows the IR spectra of glucose and maltodextrin.

Hence another calibration set is made according to the procedure described in example 13, this time including maltotriose in various concentrations, making the four mixed carbohydrates a very realistic model system for actual starch mashing. The sample composition can be seen in table 3 and the recorded spectra are shown in FIG. 29.

TABLE 3

| ENTRY | glucose | maltose | maltotriose | maltodextrin |
|---|---|---|---|---|
| 1 | 0% | 95% | 0% | 5% |
| 2 | 0% | 85% | 10% | 5% |
| 3 | 5% | 85% | 5% | 5% |
| 4 | 10% | 85% | 0% | 5% |
| 5 | 5% | 75% | 15% | 5% |
| 6 | 10% | 75% | 10% | 5% |
| 7 | 15% | 75% | 5% | 5% |
| 8 | 20% | 75% | 0% | 5% |
| 9 | 5% | 65% | 25% | 5% |
| 10 | 10% | 65% | 20% | 5% |
| 11 | 15% | 65% | 15% | 5% |
| 12 | 20% | 65% | 10% | 5% |
| 13 | 5% | 55% | 35% | 5% |
| 14 | 10% | 55% | 30% | 5% |
| 15 | 15% | 55% | 25% | 5% |
| 16 | 20% | 55% | 20% | 5% |
| 17 | 0% | 75% | 10% | 15% |
| 18 | 10% | 75% | 0% | 15% |
| 19 | 0% | 65% | 20% | 15% |
| 20 | 15% | 65% | 5% | 15% |
| 21 | 20% | 65% | 0% | 15% |
| 22 | 0% | 55% | 30% | 15% |
| 23 | 5% | 55% | 25% | 15% |
| 24 | 10% | 55% | 20% | 15% |
| 25 | 15% | 55% | 15% | 15% |
| 26 | 10% | 55% | 20% | 15% |
| 27 | 5% | 55% | 25% | 15% |
| 28 | 0% | 75% | 0% | 25% |
| 29 | 5% | 65% | 5% | 25% |
| 30 | 10% | 65% | 0% | 25% |
| 31 | 0% | 65% | 10% | 25% |
| 32 | 20% | 55% | 0% | 25% |
| 33 | 15% | 55% | 5% | 25% |
| 34 | 10% | 55% | 10% | 25% |
| 35 | 5% | 55% | 15% | 25% |
| 36 | 0% | 55% | 20% | 25% |
| 37 | 0% | 45% | 30% | 25% |
| 38 | 10% | 45% | 20% | 25% |
| 39 | 20% | 45% | 10% | 25% |
| 40 | 30% | 45% | 0% | 25% |
| 41 | 0% | 60% | 0% | 40% |
| 42 | 5% | 50% | 5% | 40% |
| 43 | 10% | 50% | 0% | 40% |
| 44 | 0% | 50% | 10% | 40% |
| 45 | 10% | 40% | 10% | 40% |
| 46 | 0% | 30% | 30% | 40% |
| 47 | 10% | 30% | 20% | 40% |
| 48 | 5% | 30% | 25% | 40% |
| 49 | 0% | 0% | 0% | 100% |

Figure 30:
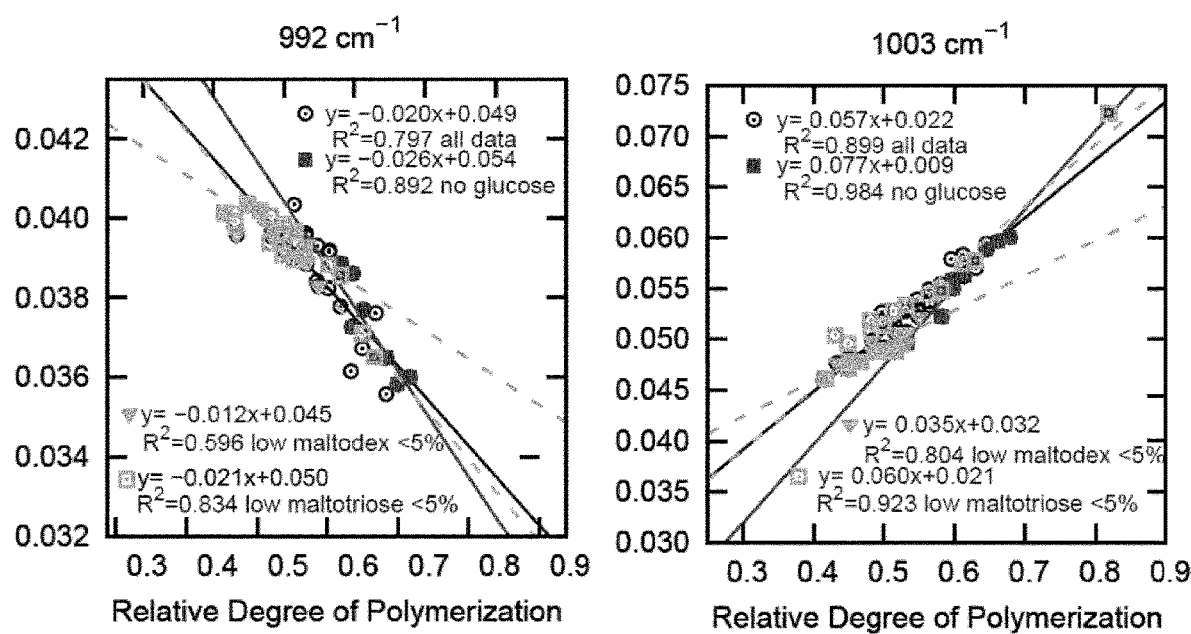
FIGS. 30-33 show correlations between deconvoluted band areas of spectra in FIG. 29 and the relative degree of polymerization at different wavelengths.
Figure 31:
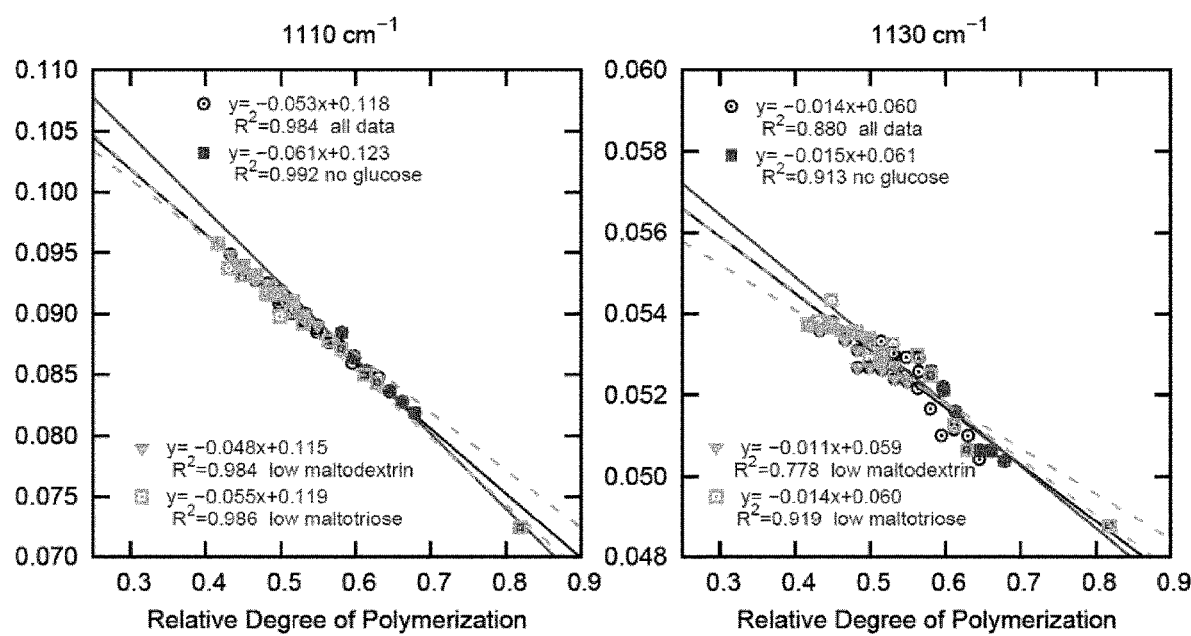
Figure 31:
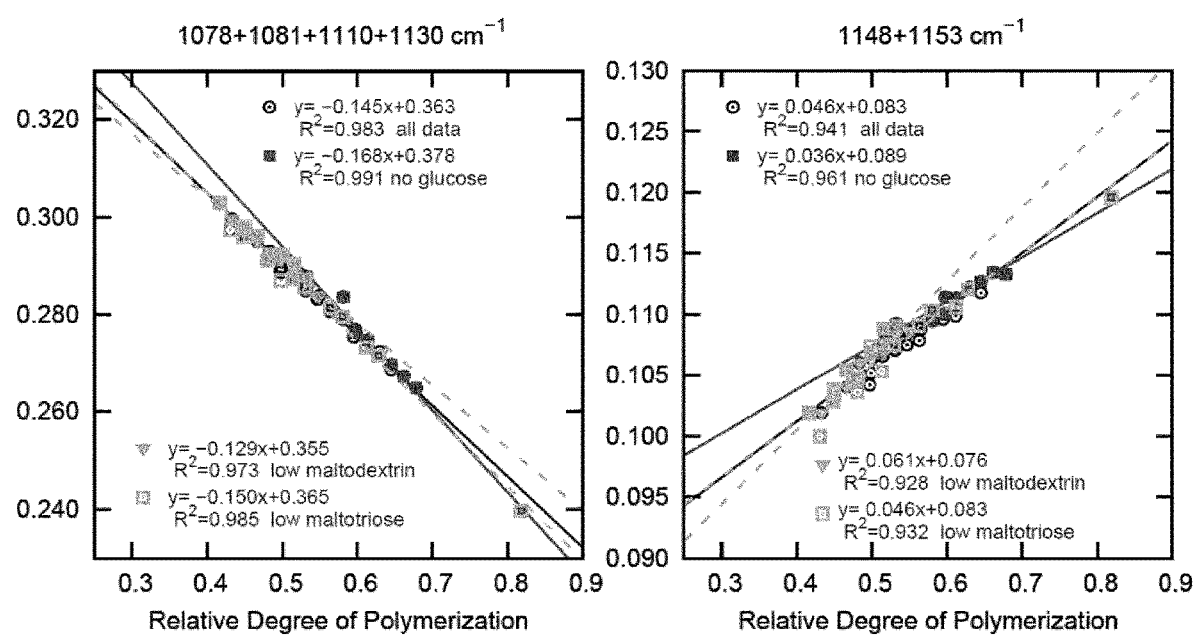

The same statistical analysis is performed on all deconvoluted and normalized band areas as in example 13. The result of the regression analysis can be seen in FIGS. 30-33. FIGS. 30-31 are similar to the presented data in FIGS. 27-28 and shows the different band areas correlation with RDP, with the exclusion of glucose, maltodextrin and maltotriose containing samples respectively. The deconvolution model parameters has been tuned slightly with respect to the ones presented previously. This is also the case for the drift correcting algorithm as well as the water subtraction procedure, which now used an experimental background instead of the analytical approximation.

The statistical trends presented in the previous example are reproduced very well with the new dataset. The trend can be seen at FIGS. 30-31, regarding correlation between the 1078+1081 cm$^{-1}$, 1110 cm$^{-1}$ and 1078+1081+1110+1130 cm$^{-1}$ bands, this time with very good statistic evidence due to the larger size of the data set. All these correlations are very good, and the resulting equations are almost identical when comparing the whole dataset with cases where parts of the dataset where excluded. The 1148+1153 cm$^{-1}$ band also behaves as in the previous example, and still seems as a good descriptor for RDP although it is slightly noisier. It also seems like the dataset reveals that this band may include some more compound specific details, with some variation in the resulting equation, however the number of analysed samples is too small for the analysis to be conclusive regarding the 1148+1153 cm$^{-1}$ band.

The analysis of the 1003 cm$^{-1}$, 1022 cm$^{-1}$ and 1003+1022 cm$^{-1}$ band area correlation with RDP shows a very accurate reproduction of the results presented in Example 13, and confirms that these bands are very useful in the discrimination of glucose in the samples. However, it is interesting to notice that the exclusion of maltotriose, result in almost identical equations as the whole data set for the 1003 cm$^{-1}$, 1022 cm$^{-1}$ and 1003+1022 cm$^{-1}$ band areas correlation with RDP.

The 1036 cm$^{-1}$ band area correlation with RDP is very different from the maltotriose free study presented in the previous example. In the previous example the 1036 cm$^{-1}$ band area is correlated very well with RDP, for the whole dataset, as well as in the two cases of exclusion of glucose and maltodextrin. Here the correlation for the whole dataset seems overall poor and noisy at first, with $R^2=0.82$. However, by exclusion of maltotriose rich samples (set point 5%) the trend changes significantly; the apparent noise is reduced, and the rest of the data now correlate well with RDP with a $R^2=0.943$.

To investigate the maltotriose influence on the dataset in details, the maltotriose rich samples are investigated in further detail by also investigating the band area correlation with RDP, by excluding maltotriose poor samples. These plots are shown in FIGS. 32-33.

The band areas 992 cm$^{-1}$, 1003 cm$^{-1}$, 1022 cm$^{-1}$, 1003+1022 cm$^{-1}$, 1078+1081 cm$^{-1}$, 1110 cm$^{-1}$, 1130 cm$^{-1}$, (1078+1081+1110+1130 cm$^{-1}$), 1148+1153 cm$^{-1}$ correlation was constant, regardless if the dataset comprised all samples, maltotriose poor samples, or maltotriose rich samples. However the 1036 cm$^{-1}$ band area correlation with RDP shows to be very sensitive to the concentration of maltotriose. Even including all samples containing down to 10 and 15% maltotriose, of the total amount of carbohydrates, showed to improve the statistics of the correlation as well as changing the slope of the resulting equation.

Figure 32:
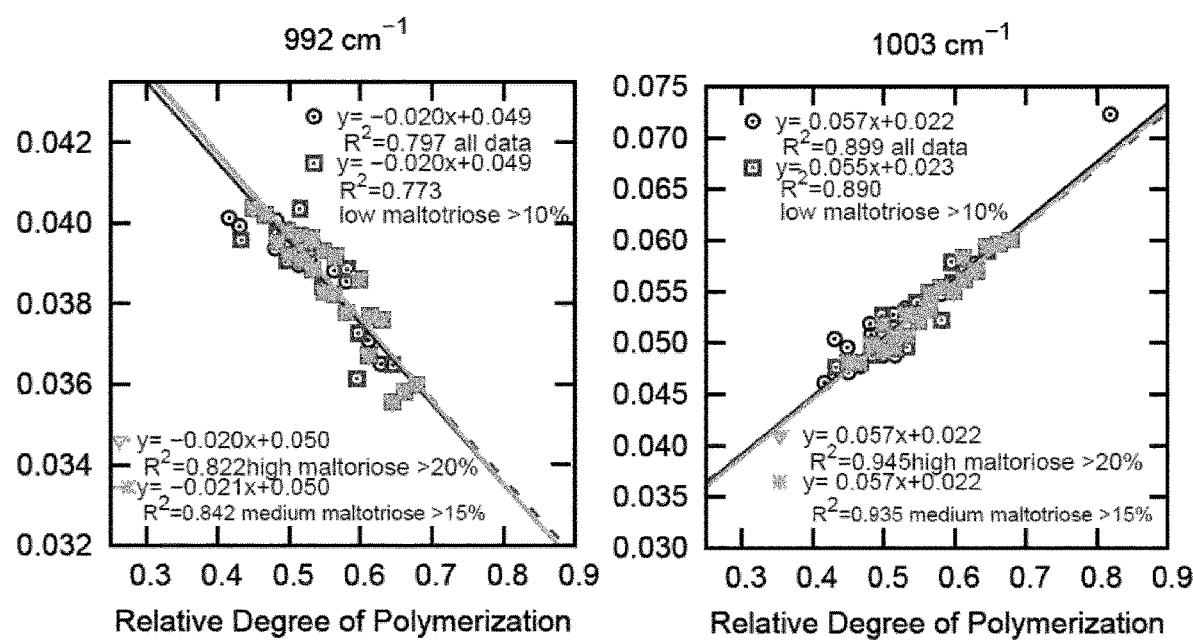
Figure 33:
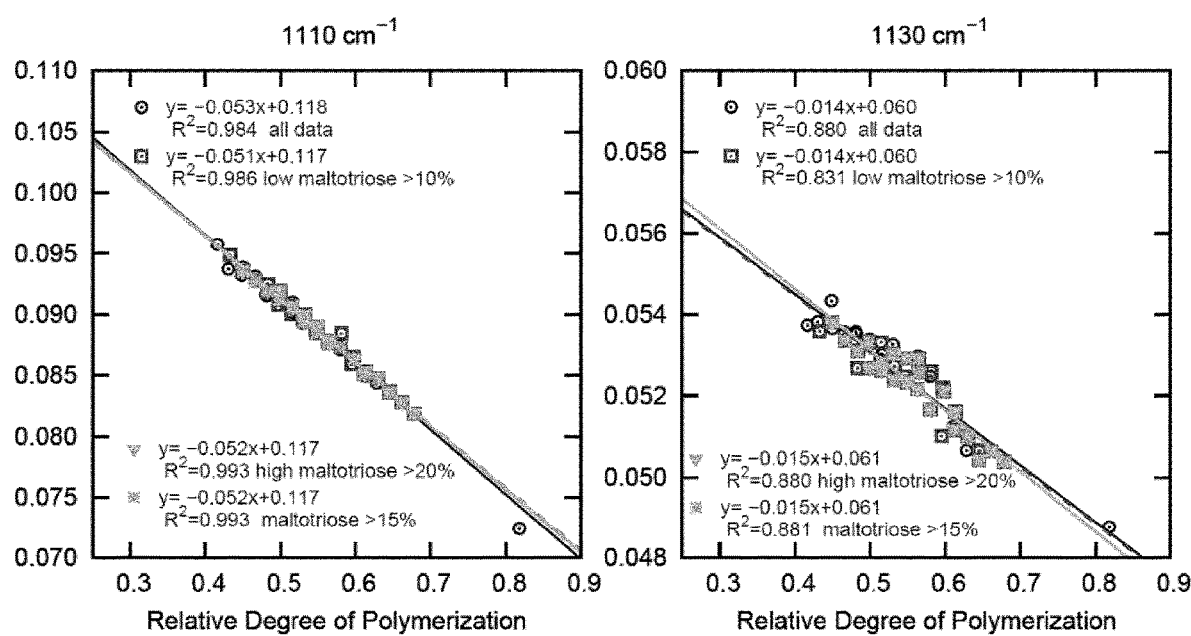
Figure 33:
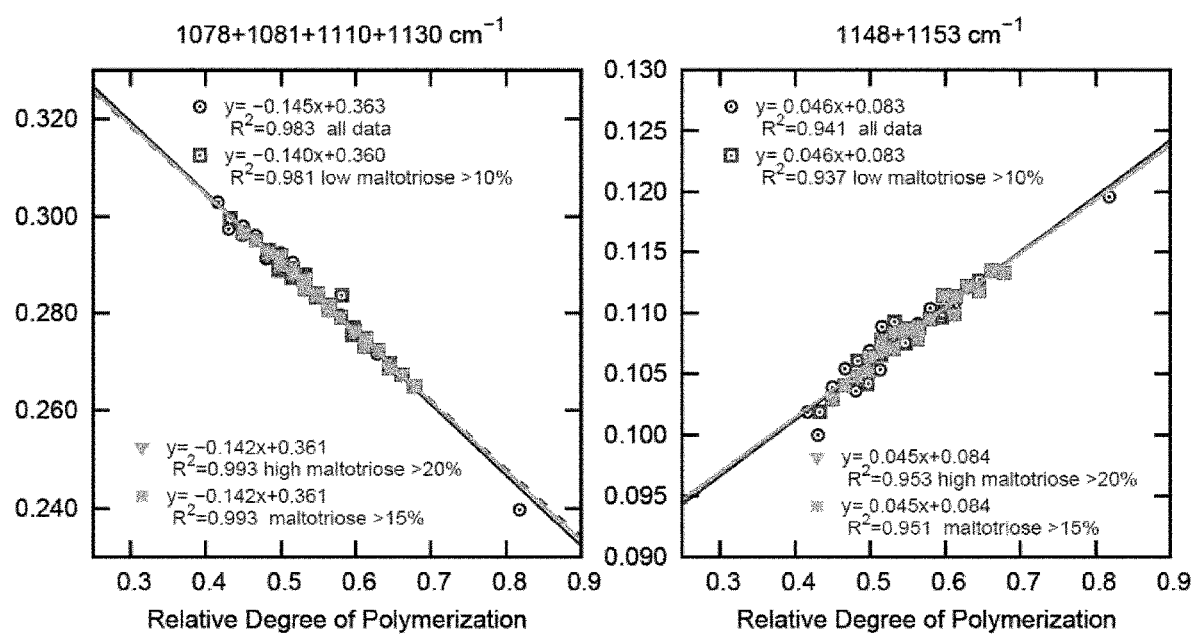

FIGS. 32-33 shows correlations between deconvoluted band areas of spectra in table 3 and the relative degree of polymerization. The different regression plots compare the whole datasets bands areas vs. RDP, bandareas where only including maltotriose rich samples.

Example 15

In this example, 150 samples are used by mixing aqueous 12% v/w solutions glucose, maltose, maltotriose and maltodextrin. The purpose of the experiments is to enhance the accuracy of multivariate calibration that allows better estimation of each specific carbohydrate compound. The samples are mixed in a way that allowed a range of different RDP values. The calibration set comprised 5 subsets of each 30 samples; the first subset containing all of the four carbohydrate components (glucose, maltose, maltotriose and maltodextrin). In the subsequent four subsets, only three compounds in each subset is included, excluding the last carbohydrate component. i.e. the 5 subset included 30 samples with a range of different combinations of the individual compounds leading to a range of RDP values: 1) Glucose, maltose, maltotriose and maltodextrin 2) maltose, maltotriose and maltodextrin
3) Glucose, maltotriose and maltodextrin
4) Glucose, maltose and maltodextrin
5) Glucose, maltose and maltotriose An ATR-IR spectra is obtained for each sample, and their ATR corrected difference spectra is treated and deconvoluted accordingly to example 14. However, in contrast to example 13 and 14 Partial Least Squares Regression (PLS) is performed instead of the manual comparative linear regression analysis. With the improved statistics of PLS it is possible to establish a multivariate model that can be applied to on-line/in-line monitoring during mashing of various starches. The multivariate model is applied on the mashing liquid in real time to supply accurate estimates of the total dissolved carbohydrate and RDP as well as estimates of the four individual carbohydrates from above (glucose, maltose, maltotriose and maltodextrin). These values are further used to calculate an accurate real time estimate of the degree of fermentability of the mash.

Example 16

Another calibration comprising 280 sample solutions is produced accordingly to the procedure in examples 13-15. However, maltotetraose is added as a fifth component, as well as a long chain maltodextrin (Low DE value) as the sixth component. Maltotetraose is obtained from a commercial high-maltotetraose corn syrup which is very high in the content of maltotetraose, with minor fractions of maltotriose and maltopentatose and almost no glucose and maltose. Using the HPLC certificate supplied by the manufacturer the exact amount of maltotetraose and maltotriose in each sample can be calculated. The calibration set is split up into seven subsets, each comprising 40 individual samples with different mixtures of the six components:

1) Glucose, maltose, maltotriose, high maltotriose syrup, maltodextrin (DE≈18) and maltodextrin (DE≈5)
2) maltose, maltotriose, high maltotriose syrup, maltodextrin (DE≈18) and maltodextrin (DE≈5)
3) Glucose, maltotriose, high maltotriose syrup, maltodextrin (DE≈18) and maltodextrin (DE≈5)
4) Glucose, maltose, high maltotriose syrup, maltodextrin (DE≈18) and maltodextrin (DE≈5)
5) Glucose, maltose, maltotriose, maltodextrin (DE≈18) and maltodextrin (DE≈5)
6) Glucose, maltose, maltotriose, high maltotriose syrup, and maltodextrin (DE≈5)
7) Glucose, maltose, maltotriose, high maltotriose syrup, maltodextrin (DE≈18)

Again, the spectra data are deconvoluted and PLS analysis was performed, to build a multivariate model. The multivariate model can again be applied in real time to supply accurate estimates of the total dissolved carbohydrate and RDP as well as estimates of the four individual carbohydrates from above (glucose, maltose, maltotriose and maltodextrin). These values are further used to calculate an accurate real time estimate of the degree of fermentability of the mash. Further this multivariate model can make some justified estimates of the fractions of the maltodextrins. The length of the maltodextrin is often important in the brewing industry as short maltodextrins like maltotriose and maltotetraose are significantly sweeter than the ones with higher degree of polymerization.

Example 17

Figure 34:
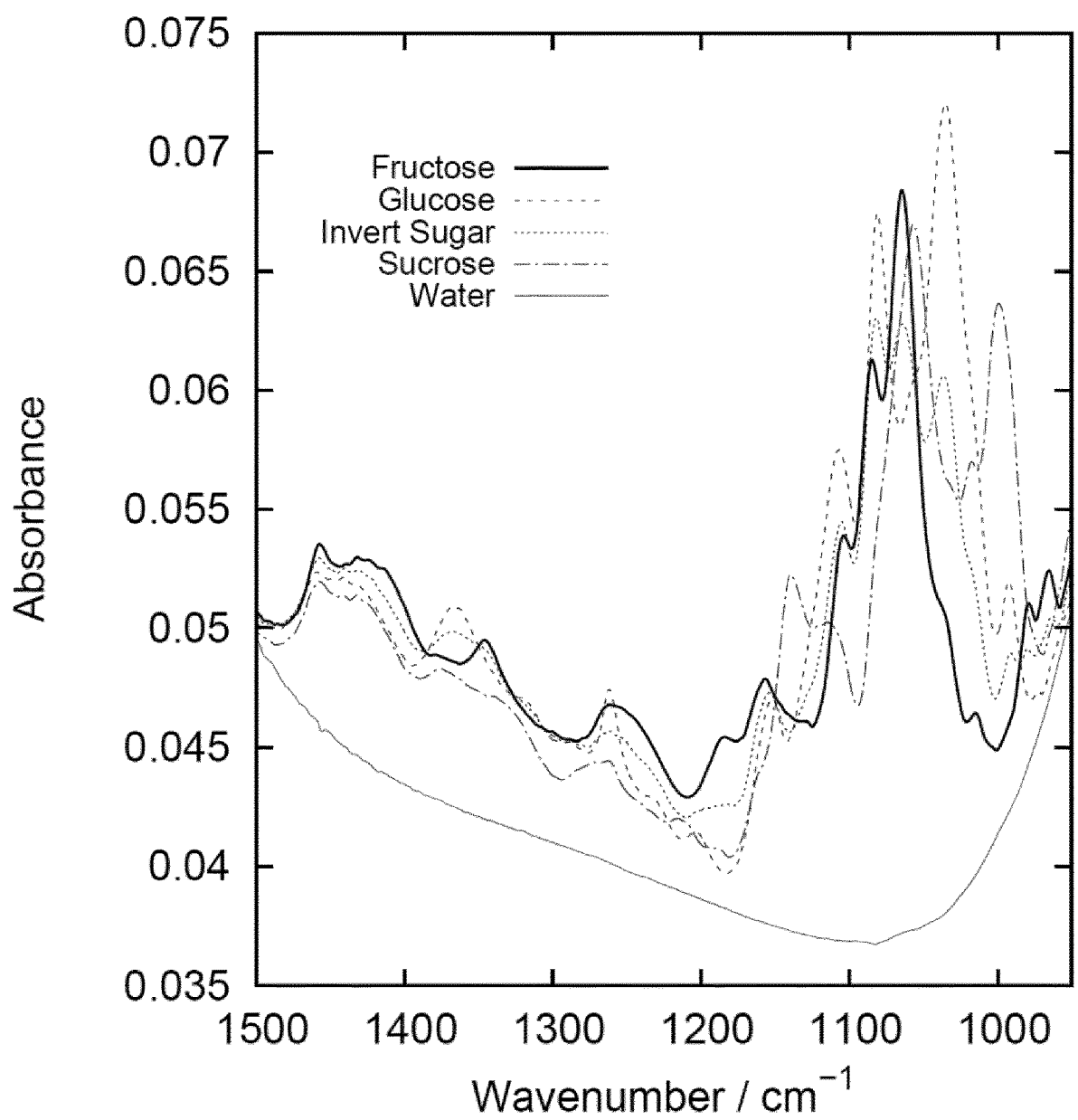
FIG. 34 shows ATR-IR spectra of the different samples.

10.0% w/v solutions of fructose, glucose, sucrose and 1:1 mixture of glucose-fructose is prepared and allowed to equilibrate. ATR-IR spectra of the samples, using golden gate ATR device, are recorded and shown in FIG. 34. The spectra of the 3 sugars shows very different spectroscopic features. It is interesting that the 1:1 mixture of glucose-fructose is markedly different from sucrose. This example, in combination with the examples mentioned above, clearly demonstrates how the present invention clearly can be applied to monitor sucrose hydrolysis in the production of invert syrups, or in the enzymatic production of fructose syrups from glucose syrups.

Example 18

Figure 35:
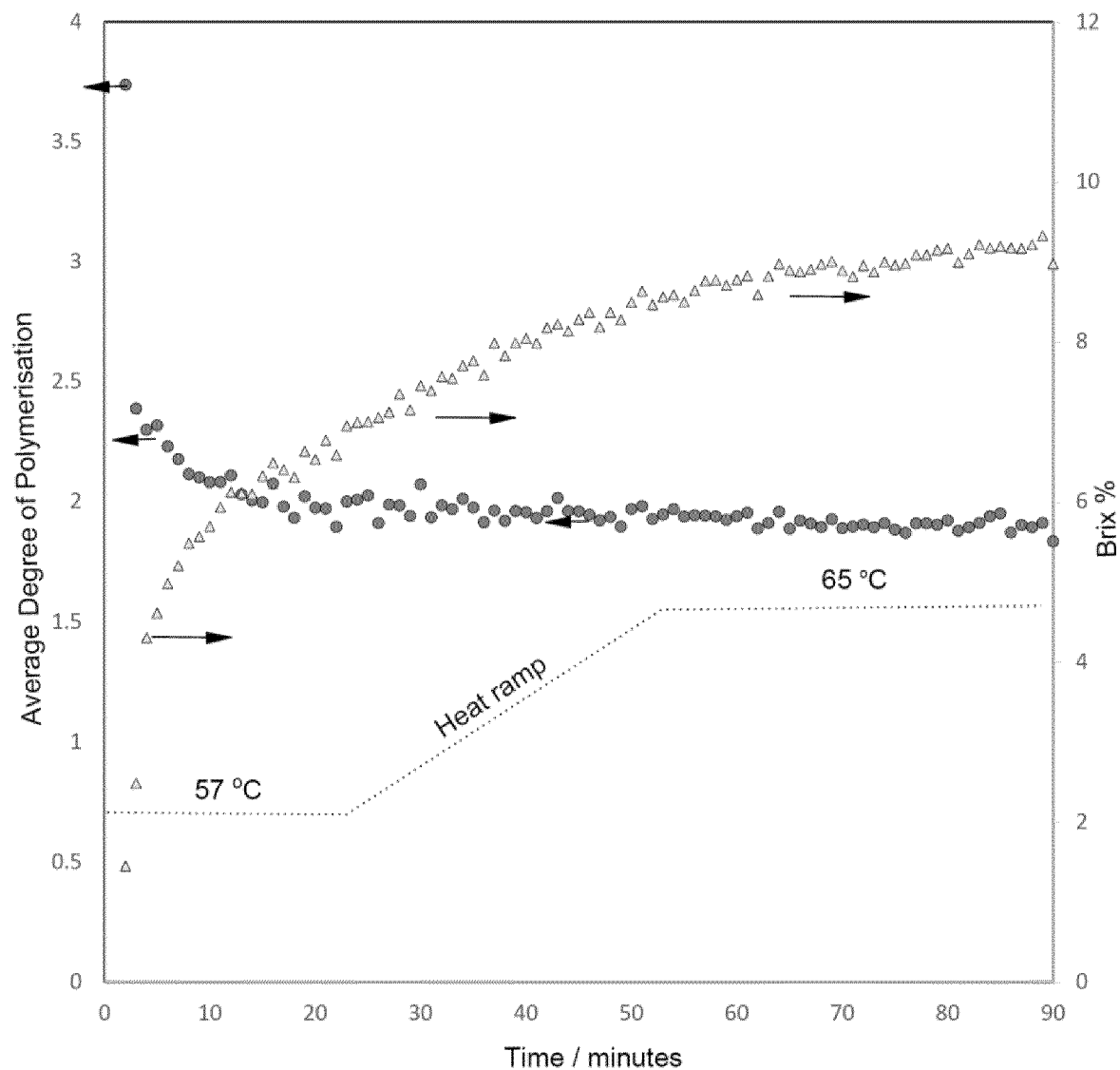
FIG. 35 shows the analysis of IR spectra measured in real time during a mashing process.

A version of the mashing analyzer similar to the one shown on FIG. 11 C is constructed. The mashing analyzer is connected to a realistic size mashing tank. Through a loop, the slurry liquid in the mashing unit is continuously pumped over the embedded ATR-IR spectroscopic unit in the analyzer recording a spectra every minute. The ATR cell in the ATR-IR unit is tilted to an angle large enough to allow the sampling area to be drained automatically by gravity during non-operation. The mashing tank is filled with water, the pH is adjusted by adding around 0.25 wt. % citric acid and the water is then heated to 57° C. The malted barley is added to the heated water in the mashing tank under mechanical stirring. The IR spectra are analyzed in real time according to the methodology and calibrations described in previous examples. From the analysis ADP and total sugar in Brix are given in real time as shown on FIG. 35, where the triangles show the total carbohydrates developed during mashing obtained from the IR spectra (scale on the right-hand side) and the circles show the ADP value based on analysis of the IR bands (scale on the left-hand side). The dotted line illustrates the temperature profile used in the mashing.

REFERENCES

100 mashing unit
102 solution/mash
104 stirring unit
106 waveguide/optical connection path
108 side channel in the mashing tank
110 computer
112 display
114 optical probe
116 fiber connected to the optical probe
118 hole in the tank
120 extraction and/or recirculation valve
122 waste tank
124 pump unit (optional)
126 extraction probe
127 recirculation probe
128 inlet
130 outlet
132 filter
134 part of the extraction probe
136 vessel mount
200 IR spectrometer
202 box
203 ATR-IR unit
204 incoming IR light
206 optical component/mirror
207 crystal in a ATR-IR plate
208 clamp
210 back reflected IR light
212 O-ring
300 analyzing chamber/ATR-IR cell 302 connector inlet
304 connector outlet
400 spectroscopic unit
401 sealed mount unit
402 spectroscopic enclosure
403 ATR-IR unit
404 plate
406 spectrophotometer
407 crystal
409 display
408 computer
410 antenna
411 lid
412 tank mount
414 seal
416 clamp
500 pumping unit
501 housing
502 motor
504 pump head
506 flow cell
600 filtration unit
602 hose

The invention claimed is:

1. A method for controlling an enzymatic pre-treatment process, the method comprising:
 a) providing a sample slurry to a system with a tank;
 b) obtaining a sample slurry mixture by:
  adding one or more enzymes to the sample slurry if the sample slurry does not contain one or more enzymes already, or
  possibly adding one or more enzymes to the sample slurry already containing one or more enzymes;
 c) continuously exposing a part of the sample slurry mixture to an infrared (IR) spectrometer on-line and/or in-line;
 d) continuously measuring attenuated total reflectance (ATR) IR spectra of the liquid part (solutes and solvents) of the sample slurry mixture with the IR spectrometer in real time at wavenumbers between 400-3500 $cm^{-1}$ during the enzymatic pre-treatment process, and
 e) feeding the measured IR spectra to a calculating unit which:
  calculates information relating to specific species present in the sample slurry mixture during the enzymatic pre-treatment process based on the IR spectra, wherein the information relating to the specific species present in the samples slurry mixture is:
   a ratio between the different specific species, or
   a concentration of one or more of the specific species, or
   a degree of polymerization of one or more of the specific species; and
  feeds the information relating to the specific species in the sample slurry mixture back to the user or to a tank control system connected to the tank.

2. The method according to claim 1, further comprising the step of:
 f) stopping the enzymatic pre-treatment process when:
  a predetermined ratio between the specific species of the liquid part in the sample slurry mixture is obtained, or
  the concentration of one or more of the specific species reached a predetermined level, or
  the degree of polymerization of one or more of the specific species reached a predetermined level,
 wherein the enzymatic pre-treatment process is either stopped manually by the user or automatically by the system on basis of the information provided from the calculation unit.

3. The method according to claim 2, wherein the enzymatic pre-treatment process is stopped by:
 the system opening the tank automatically;
 removing the sample slurry mixture from the tank, or
 increasing a temperature in the tank.

4. The method according to claim 2, wherein the IR spectra are measured at wavenumbers between 400-3000 $cm^{-1}$.

5. The method according to claim 1, further comprising stirring the sample slurry mixture during at least part of the enzymatic pre-treatment process.

6. The method according to claim 1, wherein water is added to the sample slurry mixture during the enzymatic pre-treatment process.

7. The method according to claim 6, wherein the water is added together with the possible addition of the one or more enzymes in step b).

8. The method according to claim 1, further comprising increasing or decreasing a temperature in the sample slurry or sample slurry mixture either:
 prior to starting the enzymatic pre-treatment process, or
 during the enzymatic pre-treatment process, or
 in order to stop the enzymatic pre-treatment process.

9. The method according to claim 1, wherein the sample slurry includes material selected from natural occurring carbohydrates and starch, di- and polysaccharide containing crops.

10. The method according to claim 9, wherein the sample slurry includes material selected from the group consisting of cereals, barley, wheat, rye, oat, corn, rice, potatoes, straw, wood, starch and corn stover.

11. The method according to claim 1, wherein the enzymatic pre-treatment process is a mashing process conducted prior to a fermentation process.

12. The method according to claim 1, wherein multiple enzymes are added to the sample slurry mixture either at the same time or at different times and wherein a temperature of the sample slurry mixture is adjusted during the pre-treatment process to account for differences in temperature at which each of the multiple of enzymes are most active.

13. The method according to claim 1, wherein the sample slurry comprises solid particles in a concentration of at least 1% w/w of the sample slurry.

14. The method according to claim 1, wherein the sample slurry comprises solid particles in a concentration of at least 3% w/w of the sample slurry.

15. The method according to claim 1, wherein the part of the sample slurry mixture exposed to the IR spectrometer in step c) flows over a crystal surface on the IR spectrometer.

* * * * *